(12) United States Patent
Babu et al.

(10) Patent No.: US 7,994,139 B2
(45) Date of Patent: Aug. 9, 2011

(54) ANTIVIRAL THERAPEUTIC AGENTS

(75) Inventors: Yarlagadda S. Babu, Birmingham, AL (US); Pooran Chand, Birmingham, AL (US); Pravin Kotian, Birmingham, AL (US); Minwan Wu, Birmingham, AL (US); V. Satish Kumar, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 321 days.

(21) Appl. No.: 12/398,866

(22) Filed: Mar. 5, 2009

(65) Prior Publication Data

US 2009/0227524 A1    Sep. 10, 2009

Related U.S. Application Data

(60) Provisional application No. 61/034,053, filed on Mar. 5, 2008, provisional application No. 61/079,370, filed on Jul. 9, 2008.

(51) Int. Cl.
*A01N 43/04* (2006.01)
*A61K 31/70* (2006.01)

(52) U.S. Cl. .................. 514/23; 536/18.7; 536/29.2

(58) Field of Classification Search .................. None
See application file for complete search history.

(56) References Cited

U.S. PATENT DOCUMENTS

| 7,268,119 | B2 * | 9/2007 | Cook et al. ............... 514/43 |
| 2006/0194749 | A1 | 8/2006 | Keicher et al. |
| 2010/0015094 | A1 | 1/2010 | Babu et al. |
| 2011/0002886 | A1 | 1/2011 | Babu et al. |

FOREIGN PATENT DOCUMENTS

| WO | WO 2005/021568 | 3/2005 |
| WO | WO 2008/089105 | 7/2008 |

* cited by examiner

*Primary Examiner* — Patrick Lewis
(74) *Attorney, Agent, or Firm* — Viksnins Harris & Padys PLLP

(57) ABSTRACT

The invention provides compounds of Formula I:

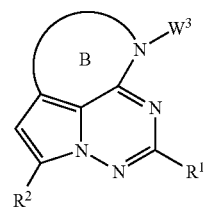

as described herein, as well as pharmaceutical compositions comprising the compounds, and synthetic methods and intermediates that are useful for preparing the compounds. The compounds of Formula (I) are useful as anti-viral agents and/or as anti-cancer agents.

24 Claims, No Drawings

ANTIVIRAL THERAPEUTIC AGENTS

RELATED APPLICATIONS

This patent application claims the benefit of priority of U.S. application Ser. No. 61/034,053 filed Mar. 5, 2008, and of U.S. application Ser. No. 61/079,370, filed Jul. 9, 2008, which applications are herein incorporated by reference.

BACKGROUND OF THE INVENTION

Viral diseases are a major cause of death and economic loss in the world. The Flaviviridae family of viruses consists of three genera: the flaviviruses (including dengue, West Nile, and yellow fever viruses), hepatitis virus (HCV), and the pestiviruses (including bovine viral diarrhea virus, BVDV). The disease states and conditions caused by members of this family include yellow fever, dengue, Japanese encephalitis, St. Louis encephalitis, Hepatitis B and C, West Nile disease, and AIDS. Currently, human immunodeficiency virus (HIV), hepatitis B virus (HBV) and hepatitis C virus (HCV) infections are responsible for the largest number of viral related deaths worldwide. Although there are some drugs useful for treating HIV, there are only a few drugs useful for treating HBV, and no drugs that are broadly useful for treating HCV. Ribavirin (1-β-D-ribofuranosyl-1-1,2,4-triazole-3-carboxamide) is a synthetic, non-interferon-inducing, broad spectrum antiviral nucleoside. Ribavirin is structurally similar to guanosine, and has in vitro activity against several DNA and RNA viruses including Flaviviridae (Davis. Gastroenterology 118:S104-S114, 2000). Ribavirin reduces serum amino transferase levels to normal in 40% of patients, but it does not lower serum levels of HCV-RNA (Davis. Gastroenterology 118:S104-S1114, 2000). Thus, ribavirin alone is not effective in reducing viral RNA levels. Additionally, ribavirin has significant toxicity and is known to induce anemia.

Interferons (IFNs) are compounds which have been commercially available for the treatment of chronic hepatitis for nearly a decade. IFNs are glycoproteins produced by immune cells in response to viral infection. IFNs inhibit viral replication of many viruses, including HCV. When used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Davis. Gastroenterology 118:S104-S114, 2000).

HCV is a positive stranded ss RNA virus with a well characterized RNA-dependent RNA polymerase (RdRp) and a well characterized disease progression. HCV has infected an estimated 170 million people worldwide, leading to a major health crisis as a result of the disease. Indeed, during the next few years the number of deaths from HCV-related liver disease and hepatocellular carcinoma may overtake those caused by AIDS. Egypt is the hardest hit country in the world, with 23% of the population estimated to be carrying the virus; whereas, in the USA the prevalence of chronic infections has recently been determined to be around 1.87% (2.7 million persons). HCV infections become chronic in about 50% of cases. Of these, about 20% develop liver cirrhosis that can lead to liver failure, including hepatocellular carcinoma.

The NS5B region of HCV encodes a 65 KDa RdRp thought to be responsible for viral genome replication. RdRps function as the catalytic subunit of the viral replicase required for the replication of all positive-strand viruses. The NS5B protein has been well characterized, shown to possess the conserved GDD motif of RdRps and in vitro assay systems have been reported. Cellular localization studies revealed that NS5B is membrane-associated in the endoplasmic reticulum like NS5A, suggesting that those two proteins may remain associated with one another after proteolytic processing. Additional evidence suggests that NS3, NS4A and NS5B interact with each other to form a complex that functions as part of the replication machinery of HCV.

The X-ray crystal structure of NS5B apoenzyme has been determined and three very recent publications describe the unusual shape of the molecule. This unique shape for a polymerase, resembling a flat sphere, is attributed to extensive interactions between the fingers and thumb subdomains in such a way that the active site is completely encircled, forming a cavity 15 Å across and 20 Å deep. Modeling studies showed that the NS5B apoenzyme can accommodate the template-primer without large movement of the subdomains, suggesting that the structure is preserved during the polymerization reaction. The RdRp polypeptides from various members of the Flaviviridae family and other viral families have been shown to be conserved (J. A. Bruenn, Nucleic Acids Research, Vol. 19, No. 2 p. 217, 1991).

Currently, there are no safe and effective therapeutic agents on the market that target HCV polymerase. There is currently a need for therapeutic agents and therapeutic methods that are useful for treating viral infections, such as HCV, HIV, and HBV.

In addition, there is also a current need for therapeutic agents and therapeutic methods that are useful for treating cancer. Even though significant advances have occurred in the treatment of cancer, it still remains a major health concern. It has been reported that cancer is the cause of death of up to one of every four Americans. Notwithstanding the advances in treatments for cancer and other diseases there is still a need for novel drugs that are effective to treat cancer.

SUMMARY OF THE INVENTION

The present invention provides compounds that are inhibitors of viral RNA and DNA polymerases (e.g. polymerases from hepatitis B, hepatitis C, human immunodeficiency virus, Polio, Coxsackie A and B, Rhino, Echo, small pox, Ebola, and West Nile virus) and that are useful for treating HCV, as well as other viral infections (e.g. flaviviral infections), and cancer.

Accordingly, the invention provides a novel compound of Formula I as described herebelow, or a pharmaceutically acceptable salt or prodrug thereof.

The invention also provides a pharmaceutical composition comprising a compound of Formula I, or a pharmaceutically acceptable salt or prodrug thereof, and a pharmaceutically acceptable carrier. The composition can optionally comprise one or more additional anti-viral or anti-cancer agents.

The invention also provides a method for treating a viral infection in an animal comprising administering to the animal an effective amount of a compound of Formula I, or a pharmaceutically acceptable salt or prodrug thereof.

The invention also provides a method for inhibiting a viral RNA or DNA polymerase comprising contacting the polymerase (in vitro or in vivo) with an effective inhibitory amount of a compound of Formula I, or a pharmaceutically acceptable salt or prodrug thereof.

The invention also provides a method for treating cancer in an animal comprising administering to the animal an effective amount of a compound of Formula I, or a pharmaceutically acceptable salt or prodrug thereof.

The invention also provides a compound of Formula I, or a pharmaceutically acceptable salt or prodrug thereof, for use in medical therapy (e.g. for use in treating a viral infection or for use in treating cancer).

The invention also provides the use of a compound of Formula I, or a pharmaceutically acceptable salt or prodrug thereof, to prepare a medicament useful for treating a viral infection in an animal (e.g. a human).

The invention also provides the use of a compound of Formula I, or a pharmaceutically acceptable salt or prodrug thereof, to prepare a medicament useful for treating cancer in an animal (e.g. a human).

The invention also provides a compound of Formula I, or a pharmaceutically acceptable salt or prodrug thereof, for the prophylactic or therapeutic treatment of a viral infection.

The invention also provides a compound of Formula I, or a pharmaceutically acceptable salt or prodrug thereof, for the prophylactic or therapeutic treatment of cancer.

The invention also provides novel synthetic intermediates and synthetic methods that are disclosed herein as being useful for preparing compounds of Formula I, or a salt or prodrug thereof. Some compounds of Formula I may be useful as synthetic intermediates for preparing other compounds of Formula I.

DETAILED DESCRIPTION OF THE INVENTION

Definitions

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

The terms "treat", "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

The term "animal" as used herein refers to any animal, including mammals, such as, but not limited to, mice, rats, other rodents, rabbits, dogs, cats, swine, cattle, sheep, horses, and primates. In one specific embodiment of the invention the animal is a human.

The term "therapeutically effective amount", in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The term "alkyl" as used herein refers to alkyl groups having from 1 to 6 carbon atoms. This term is exemplified by groups such as methyl, ethyl, n-propyl, iso-propyl, n-butyl, t-butyl, n-pentyl and the like. In a specific embodiment, the alkyl groups have from 1-4 carbon atoms and are referred to as lower alkyl.

The term "substituted alkyl" as used herein refers to an alkyl group having from 1 to 3 substituents, said substituents being selected from the group consisting of alkoxy, alkoxyalkyl, tri($C_1$-$C_4$alkyl)silyl, substituted alkoxy, acyl, substituted acyl, acylamino, acyloxy, oxyacyl, amino, substituted amino, aminoacyl, aryl, substituted aryl, aryloxy, substituted aryloxy, cyano, halogen, hydroxyl, nitro, $N_3$, carboxyl, carboxyl esters, thiol, thioalkyl, substituted thioalkyl, thioaryl, substituted thioaryl, thioheteroaryl, substituted thioheteroaryl, thiocycloalkyl, substituted thiocycloallcyl, thioheterocyclic, substituted thioheterocyclic, cycloalkyl, substituted cycloalkyl, heteroaryl, substituted heteroaryl, heterocyclic, and substituted heterocyclic. In one specific embodiment of the invention, the term "substituted alkyl" refers to an alkyl group substituted with 1 to 3 substituents, said substituents being selected from the group consisting of alkoxy, alkoxyalkyl, tri($C_1$-$C_4$alkyl)silyl, acyl, acylamino, acyloxy, oxyacyl, amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

The terms "alkenyl" or "alkene" as used herein refers to an alkenyl group having from 2 to 10 carbon atoms and having at least 1 site of alkenyl unsaturation. Such groups are exemplified by vinyl(ethen-1-yl), allyl, but-3-en-1-yl, and the like.

The term "substituted alkenyl" as used herein refers to alkenyl groups having from 1 to 3 substituents, said substituents being selected from those describe above for a substituted alkyl.

The term "alkynyl" or "alkyne" as used herein refers to an alkynyl group having from 2-10 carbon atoms and having at least 1 site of alkynyl unsaturation. Such groups are exemplified by, but not limited to, ethyn-1-yl, propyn-1-yl, propyn-2-yl, 1-methylprop-2-yn-1-yl, butyn-1-yl, butyn-2-yl, butyn-3-yl, and the like.

The term "substituted alkynyl" as used herein refers to alkynyl groups having from 1 to 3 substituents, said substituents being selected those describe above for a substituted alkyl.

The term "alkoxy" refers to the group alkyl-O—.

The term "substituted alkoxy" as used herein refers to the group substituted alkyl-O—.

The term "acyl" as used herein refers to the groups alkyl-C(O)—, alkenyl-C(O)—, alkynyl-C(O)—, cycloalkyl-C(O)—, aryl-C(O)—, heteroaryl-C(O)—, and heterocyclic-C(O).

The term "substituted acyl" as used herein refers to the groups substituted alkyl-C(O)—, substituted alkenyl-C(O)—, substituted alkynyl-C(O)—, substituted cycloalkyl-C(O)—, substituted aryl-C(O)—, substituted heteroaryl-C(O), and substituted heterocyclic-C(O)—.

The term "acylamino" as used herein refers to the group-C(O)N$Z_1Z_2$ where each $Z_1$ and $Z_2$ are independently selected from the group consisting of hydrogen, alkyl, substituted alkyl, alkenyl, substituted alkenyl, alkynyl and substituted alkynyl, and the substituents described above in the definition of substituted alkyl.

The term "acyloxy" as used herein refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

The term "oxyacyl" as used herein refers to the groups alkyl-OC(O)—, substituted alkyl-OC(O)—, alkenyl-OC(O)—, substituted alkenyl-OC(O)—, alkynyl-OC(O)—, substituted alkynyl-OC(O)—, aryl-OC(O)—, substituted aryl- OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

The term "amino" as used herein refers to the group —NH$_2$.

The term "substituted amino" as used herein refers to the group-NZ$_1$Z$_2$ where Z$_1$ and Z$_2$ are as described above in the definition of acylamino, provided that Z$_1$ and Z$_2$ are both not hydrogen.

The term "aminoacyl" as used herein refers to the groups —NZ$_3$C(O)alkyl, —NZ$_3$C(O)substituted alkyl, —NZ$_3$C(O)cycloalkyl, —NZ$_3$C(O)substituted cycloalkyl, —NZ$_3$C(O)alkenyl, —NZ$_3$C(O)substituted alkenyl, —NZ$_3$C(O)alkynyl, —NZ$_3$C(O)substituted alkynyl, —NZ$_3$C(O)aryl, —NZ$_3$C(O)substituted aryl, —NZ$_3$C(O)heteroaryl, —NZ$_3$C(O)substituted heteroaryl, —NZ$_3$C(O)heterocyclic, and —NZ$_3$C(O)substituted heterocyclic, where Z$_3$ is hydrogen or alkyl.

The term "aryl" as used herein refers to a monovalent aromatic cyclic group of from 6 to 14 carbon atoms having a single ring (e.g., phenyl) or multiple condensed rings (e.g., naphthyl or anthryl) which condensed rings may or may not be aromatic. Exemplary aryls include, but are not limited to, phenyl and naphthyl.

The term "substituted aryl" as used herein refers to aryl groups which are substituted with from 1 to 3 substituents selected from alkyl, substituted alkyl, alkenyl, substituted alkenyl, alkynyl and substituted alkynyl, and those substituents described above in the definition of substituted alkyl.

The term "aryloxy" as used herein refers to the group aryl-O— that includes, by way of example but not limitation, phenoxy, naphthoxy, and the like.

The term "substituted aryloxy" as used herein refers to substituted aryl-O-groups.

The term "carboxyl" as used herein refers to —COOH or salts thereof.

The term "carboxyl esters" as used herein refers to the groups-C(O)O-alkyl, —C(O)O-substituted alkyl, —C(O)O-aryl, and —C(O)O-substituted aryl.

The term "cycloalkyl" as used herein refers to a saturated or unsaturated cyclic hydrocarbon ring systems, such as those containing 1 to 3 rings and 3 to 7 carbons per ring. Exemplary groups include but are not limited to cyclopropyl, cyclobutyl, cyclopentyl, cyclohexyl, cycloheptyl, and adamantyl.

The term "substituted cycloalkyl" as used herein refers to a cycloalkyl having from 1 to 5 substituents selected from the group consisting of oxo (=O), thioxo (=S), alkyl, substituted alkyl, and those substituents described in the definition of substituted alkyl.

The term "cycloalkoxy" as used herein refers to —O-cycloalkyl groups.

The term "substituted cycloalkoxy" as used herein refers to —O-substituted cycloalkyl groups.

The term "formyl" as used herein refers to HC(O)—.

The term "halogen" as used herein refers to fluoro, chloro, bromo and iodo.

The term "heteroaryl" as used herein refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms. Such heteroaryl groups can have a single ring (e.g., pyridyl or furyl) or multiple condensed rings (e.g., indolizinyl or benzothienyl) wherein the condensed rings may or may not be aromatic and/or contain a heteroatom. Exemplary heteroaryl groups include, but are not limited to, heteroaryls include pyridyl, pyrrolyl, thienyl, indolyl, thiophenyl, and furyl.

The term "substituted heteroaryl" as used herein refers to heteroaryl groups that are substituted with from 1 to 3 substituents selected from the same group of substituents defined for substituted aryl.

The term "heteroaryloxy" as used herein refers to the group —O-heteroaryl.

The term "substituted heteroaryloxy" as used herein refers to the group —O-substituted heteroaryl.

The term "heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, within the ring wherein, in fused ring systems, one or more the rings can be cycloalkyl, aryl or heteroaryl provided that the point of attachment is through the heterocyclic ring. The sulfur and nitrogen heteroatoms atoms may also be present in their oxidized forms.

The term "substituted heterocycle" or "substituted heterocyclic" or "substituted heterocycloalkyl" refers to heterocycle groups that are substituted with from 1 to 3 of the same substituents as defined for substituted aryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "heterocyclyloxy" as used herein refers to the group —O-heterocyclic.

The term "substituted heterocyclyloxy" as used herein refers to the group-O-substituted heterocyclic.

The term "phosphate" as used herein refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood that the initial oxygen of the mono-, di-, and triphosphate may include the oxygen atom of a sugar.

The term "phosphate esters" as used herein refers to the mono-, di- and tri-phosphate groups described above wherein one or more of the hydroxyl groups is replaced by an alkoxy group.

The term "phosphonate" refers to the groups —OP(O)(Z$_4$)(OH) or —OP(O)(Z$_4$)(OZ$_4$) or salts thereof including partial salts thereof, wherein each Z$_4$ is independently selected from hydrogen, alkyl, substituted alkyl, carboxylic acid, and carboxyl ester. It is understood that the initial oxygen of the phosphonate may include the oxygen of a sugar.

The term "thiol" as used herein refers to the group —SH.

The term "thioalkyl" or "alkylthioether" or "thioalkoxy" refers to the group —S-alkyl.

The term "substituted thioalkyl" or "substituted alkylthioether" or "substituted thioalkoxy" refers to the group —S-substituted alkyl.

The term "thiocycloalkyl" as used herein refers to the group —S-cycloalkyl.

The term "substituted thiocycloalkyl" as used herein refers to the group —S-substituted cycloalkyl.

The term "thioaryl" as used herein refers to the group —S-aryl.

The term "substituted thioaryl" as used herein refers to the group-S-substituted aryl.

The term "thioheteroaryl" as used herein refers to the group —S-heteroaryl.

The term "substituted thioheteroaryl" as used herein refers to the group —S-substituted heteroaryl.

The term "thioheterocyclic" as used herein refers to the group —S-heterocyclic.

The term "substituted thioheterocyclic as used herein refers to the group —S-substituted heterocyclic.

The term "amino acid sidechain" refers to the $Z_7$ substituent of α-amino acids of the formula $Z_6NHCH(Z_7)COOH$ where $Z_7$ is selected from the group consisting of hydrogen, alkyl, substituted alkyl and aryl and $Z_6$ is hydrogen or together with $Z_7$ and the nitrogen and carbon atoms bound thereto respectively form a heterocyclic ring. In one embodiment, the α-amino acid sidechain is the sidechain of one of the twenty naturally occurring L amino acids.

Sugars described herein may either be in D or L configuration.

Compounds of Formula I

Compounds of the invention include compounds of formula I:

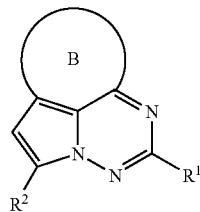

wherein;
B represents a 5, 6, 7 or 8 membered carbocyclic or heterocyclic ring comprising one or more double bonds, wherein B is optionally substituted with one or more oxo, thioxo, $NR_cR_d$, F, Cl, Br, I, $OR_z$, $SR_z$, alkyl, C≡N, C≡C—R, $N_3$ or $SO_2R'$;
wherein:
R is H, alkyl or aryl;
R' is OH, $NH_2$ or alkyl;
$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;
$R^2$ is a nucleoside sugar group;
$W^3$ is absent, alkyl, or H;
$R_a$ and $R_b$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl, amino, substituted amino, and NO; or $R_a$ and $R_b$ together with the nitrogen to which they are attached form a pyrrolidino, piperidino, piperazino, azetidino, morpholino, or thiomorpholino ring;
$R_c$ and $R_d$ are independently selected from the group consisting of H, alkyl, substituted alkyl, alkenyl, substituted alkenyl, alkynyl, substituted alkynyl, cycloalkyl, acyl, substituted acyl and $SO_2$-alkyl; or $R_c$ and $R_d$ together with the nitrogen to which they are attached form a pyrrolidino, piperidino, piperazino, azetidino, morpholino, or thiomorpholino ring; and
each $R_z$ is independently selected from the group consisting of H, alkyl, substituted alkyl, alkenyl, substituted alkenyl, alkynyl, substituted alkynyl, cycloalkyl, acyl and substituted acyl;

or a pharmaceutically acceptable salt or prodrug thereof.

In one embodiment of the invention the compound of formula I is a compound of formula II:

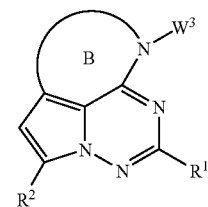

wherein;
B represents a 5, 6, 7 or 8 membered ring comprising one or more heteroatoms and one or more double bonds, wherein B is optionally substituted with one or more oxo, thioxo, $NR_cR_d$, F, Cl, Br, I, $OR_z$, $SR_z$, alkyl, C≡N, C≡C—R, $N_3$ or $SO_2R'$;
wherein:
R is H, alkyl or aryl;
R' is OH, $NH_2$ or alkyl;
$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;
$R^2$ is a nucleoside sugar group;
$W^3$ is absent, alkyl, or H;
$R_a$ and $R_b$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl, amino, substituted amino, and NO; or $R_a$ and $R_b$ together with the nitrogen to which they are attached form a pyrrolidino, piperidino, piperazino, azetidino, morpholino, or thiomorpholino ring;
$R_c$ and $R_d$ are independently selected from the group consisting of H, alkyl, substituted alkyl, alkenyl, substituted alkenyl, alkynyl, substituted alkynyl, cycloalkyl, acyl, substituted acyl and $SO_2$-alkyl; or $R_c$ and $R_d$ together with the nitrogen to which they are attached form a pyrrolidino, piperidino, piperazino, azetidino, morpholino, or thiomorpholino ring; and
each $R_z$ is independently selected from the group consisting of H, alkyl, substituted alkyl, alkenyl, substituted alkenyl, alkynyl, substituted alkynyl, cycloalkyl, acyl and substituted acyl;

or a pharmaceutically acceptable salt or prodrug thereof.

In one embodiment of the invention the compound of formula I is a compound of formula II wherein $W^3$ is absent or H.

In one embodiment of the invention the compound of formula I is a compound of formula III:

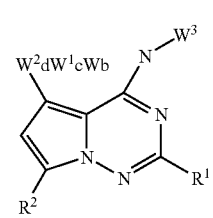

wherein:
each b, c and d is independently selected from a single and double bond provided that when b is a double bond, c is single bond, when c is a double bond, b and d are single bonds and when d is a double bond c is a single bond; or d is absent when $W^2$ is absent; and $W^2$ and d are not absent, when $bNW^3$ is absent;

W is $C=R_e$, $CH_2$, $CR_g$ or O, provided that when W is $C=R_e$, $CH_2$ or O, b and c are single bonds, or c is a single bond and $bNW^3$ is absent; and provided when W is $CR_g$, one of b or c is a double bond, or $bNW^3$ is absent and c is a double bond;

$R_e$ is O or S;
$R_g$ is H, $NR_cR_d$, $OR_z$, or $SR_z$;
$W^1$ is $C=R_h$, $CR_iR_i$, N, $NR_n$, $CR_j$ or O provided that when $W^1$ is $C=R_h$, $CR_iR_i$, $NR_n$ or O, c and d are single bonds or c is a single bond and $W^2d$ is absent; and provided when $W^1$ is $CR_j$ or N one of c or d is a double bond or W2d is absent and c is a double bond;

$R_h$ is O or S;
$R_i$ and $R_{i'}$ are H, $CH_3$, $NH_2$ or Br;
$R_j$ is $CH_3$, $NH_2$, or H;
$W^2$ is $C=R_k$, $(CR_lR_{l'})_{p'}$, $CR_m$, O, $NR_s$, absent or N provided that when $W^2$ is $C=R_k$, $CR_lR_{l'}$, O, or $NR_sd$ is a single bond; when $W^2$ is N or $CR_md$ is a double bond; and provided when $W^2$ is absent, d is absent;

$R_k$ is O or S;
$R_l$ and $R_{l'}$ are H, $CH_3$, $OCH_3$, $NH_2$ or $SCH_3$;
p' is 1 or 2;
$R_m$ is H, $NR_cR_d$, F, Cl, Br, I, $OR_z$, $SR_z$, alkyl, $C\equiv N$, $C\equiv C-R$, $N_3$ or $SO_2R'$;
$R_n$ is H, alkyl, or $NR_qR_r$ wherein each $R_q$ and $R_r$ is H or alkyl;
$R_s$ is H, $CH_3$, or $NH_2$; and
$W^3$ is absent, H or alkyl; provided that when $W^3$ is absent b is a double bond;
or a pharmaceutically acceptable salt or prodrug thereof.

In one embodiment of the invention the compound of formula I is a compound of formula IV:

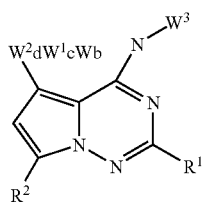

(IV)

wherein:
each b, c and d is independently selected from a single or double bond provided that when b is a double bond, c is single bond, when c is a double bond, b and d are single bonds and when d is a double bond c is a single bond; or d is absent when $W^2$ is absent;

W is $C=R_e$, $CR_fR_f$, $CR_g$ or O, provided that when W is $C=R_e$, $CR_fR_f$ or O, b and c are single bonds and when W is $CR_g$, one of b or c is a double bond;

$R_e$ is O or S;
$R_f$ is H;
$R_g$ is H, $NR_cR_d$, $OR_z$, or $SR_z$;
$W^1$ is $C=R_h$, $CR_iR_i$, NH, $CR_j$ or O provided that when $W^1$ is $C=R_h$, $CR_iR_i$, or O, c and d are single bonds; when $W^1$ is $CR_j$, one of c or d is a double bond; and when $W^1$ is NH, W is not O and $W^2$ is not O, NH, or N;

$R_h$ is O or S;
$R_i$ and $R_{i'}$ are H, $CH_3$ or Br;
$R_j$ is $CH_3$ or H;

$W^1$ is $C=R_k$, $(CR_lR_{l'})_{p'}$, $CR_m$, O, NH, absent, or N provided that when $W^2$ is $C=R_k$, $CR_lR_{l'}$, $CR_m$, O, or NHd is a single bond; when $W^2$ is N or $CR_md$ is a double bond; or when $W^2$ is absent, d is absent;

$R_k$ is O or S;
$R_l$ and $R_{l'}$ are H, $CH_3$, $OCH_3$ or $SCH_3$;
p' is 1 or 2;
$R_m$ is H, $NR_cR_d$, F, Cl, Br, I, $OR_z$, $SR_z$, alkyl, $C\equiv N$, $C\equiv C-R$, $N_3$ or $SO_2R'$; and
$W^3$ is absent, H or alkyl; provided that when $W^3$ is absent b is a double bond;
or a pharmaceutically acceptable salt or prodrug thereof.

In one embodiment of the invention the compound of formula I is a compound of formula IV wherein:
each b, c and d is independently selected from a single or double bond provided that when b is a double bond, c is single bond, when c is a double bond, b and d are single bonds and when d is a double bond c is a single bond;

W is $C=R_e$, $CR_fR_f$, $CR_g$ or O, provided that when W is $C=R_e$, $CR_fR_f$ or O, b and c are single bonds and when W is $CR_g$, one of b or c is a double bond;

$R_e$ is O or S;
$R_f$ is H;
$R_g$ is H, $NR_cR_d$, $OR_z$ or $SR_z$;
$W^1$ is $C=R_h$, $CR_iR_i$, $CR_j$ or O provided that when $W^1$ is $C=R_h$, $CR_iR_i$, or O, c and d are single bonds and when $W^1$ is $CR_j$, one of c or d is a double bond;

$R_h$ is O or S;
$R_i$ and $R_{i'}$ are H, $CH_3$ or Br;
$R_j$ is $CH_3$ or H;
$W^2$ is $C=R_k$, $(CR_lR_{l'})_{p'}$, $CR_m$, O, NH or N provided that when $W^2$ is $C=R_k$, $CR_lR_{l'}$, $CR_m$, O, or NHd is a single bond and when $W^2$ is N or $CR_md$ is a double bond;

$R_k$ is O or S;
$R_l$ and $R_{l'}$ are H, $CH_3$, $OCH_3$ or $SCH_3$;
p' is 1 or 2;
$R_m$ is H, $NR_cR_d$, F, Cl, Br, I, $OR_z$, $SR_z$, alkyl, C_N, $C\equiv C-R$, $N_3$ or $SO_2R'$; and
$W^3$ is absent or H, provided that when $W^3$ is absent b is a double bond;
or a pharmaceutically acceptable salt or prodrug thereof.

In one embodiment of the invention the compound of formula I is a compound of formula V:

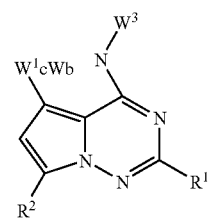

(V)

wherein:
each of b and c is independently selected from a single or double bond provided that when b is a double bond, c is single bond and when c is a double bond b is a single bond;

W is $C=R_e$, $CR_fR_f$, $CR_g$ or O, provided that when W is $C=R_e$, $CR_fR_f$ or O, b and c are single bonds and when W is $CR_g$, one of b or c is a double bond;

$R_e$ is O or S;
$R_f$ is H;
$R_g$ is H, $NR_cR_d$, $OR_z$ or $SR_z$;

$W^1$ is C=$R_h$, $CR_iR_i$, NH, $CR_j$ or O provided that when $W^1$ is C=$R_h$, $CR_iR_i$, or O, c is a single bond; when $W^1$ is $CR_j$, c is a double bond; and when $W^1$ is NH, W is not O;

$R_h$ is O or S;

$R_i$ and $R_{i'}$ are each independently H, $CH_3$ or Br;

$R_j$ is $CH_3$ or H; and $W^3$ is absent, H, or alkyl, provided that when $W^3$ is absent b is a double bond;

or a pharmaceutically acceptable salt or prodrug thereof.

In one embodiment of the invention the compound of formula I is a compound of formula V wherein $W^3$ is absent, H, or methyl.

In one embodiment of the invention the compound of formula I is a compound of formula V wherein $W^3$ is methyl.

In another embodiment of the invention provides compounds of formula I that are compounds of formula 1-9:

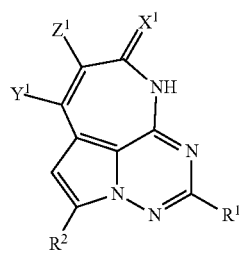

1

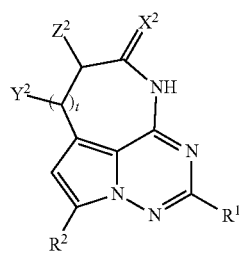

2

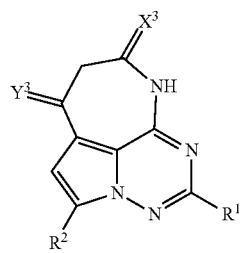

3

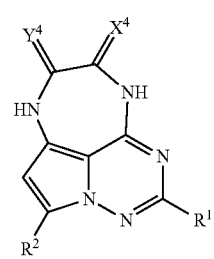

4

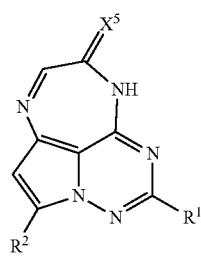

5

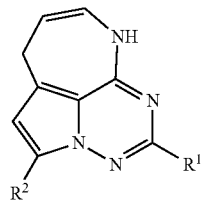

6

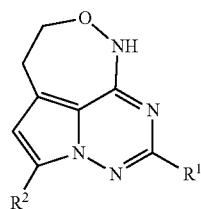

7

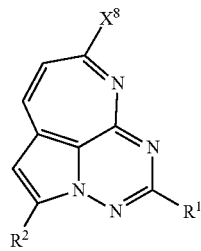

8

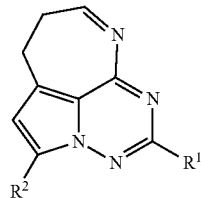

9 wherein:
$X^1$ is O, S, or two hydrogens;
$X^2$ is O, S, or two hydrogens;
$X^3$ is O or S;
$X^4$ is O, S, or two hydrogens;
$X^5$ is O, S, or two hydrogens;
$X^8$ is $NH_2$, $OCH_3$ or $SCH_3$;
$Y^1$ is H, OH, $NH_2$, $NHCH_3$, $N(CH_3)_2$, F, Cl, Br, I, $OCH_3$, Oalkyl, alkyl $SCH_3$, $CH_3$, C≡N, C≡C—R, $N_3$ or $SO_2R'$;
$Y^2$ is H, $CH_3$, $OCH_3$ or $SCH_3$;
$Y^3$ is O or S;
$Y^4$ is O, S, or two hydrogens;
$Z^1$ is H or $CH_3$;
$Z^2$ is H, $CH_3$ or Br; and
t is 1 or 2;
or a pharmaceutically acceptable salt or prodrug thereof.

In another embodiment the invention provides a compound of Formula I as described above, wherein $R^1$ is H or $NR_aR_b$; or a pharmaceutically acceptable salt or prodrug thereof.

In another embodiment the invention provides a compound of Formula I as described above, wherein $R^2$ is a nucleoside sugar group of Group A, B, C, D, E, or F described hereinbelow; or a pharmaceutically acceptable salt or prodrug thereof.

In another embodiment the invention provides a compound of Formula I as described above, wherein $R^2$ is ribose, 2-methylribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose; or a pharmaceutically acceptable salt or prodrug thereof.

In another embodiment the invention provides a compound of Formula I as described above, wherein $R^2$ is thioribose, 2-deoxythioribose; 2-deoxy-2-fluorothioribose; thioarabinose; 2-deoxy-2-fluorothioarabinose; 2,3-dideoxythioribose; 2,3-dideoxy-2-fluorothioarabinose; 2,3-dideoxy-3-fluorothioribose; 2,3-dideoxy-2,3-didehydrothioribose; or 2,3-dideoxy-3-azidothioribose; or a pharmaceutically acceptable salt or prodrug thereof.

In another embodiment the invention provides a compound of Formula I as described above, wherein $R^2$ is 4-hydroxymethylcyclopent-2-ene; 2,3-dihydroxy-4-hydroxymethylcyclopent-4-ene; 3-hydroxy-4-hydroxymethylcyclopentane; 2-hydroxy-4-hydroxymethylcyclopentene; 2-fluoro-3-hydroxy-4-hydroxymethylcyclopentane; 2,3-dihydroxy-4-hydroxymethyl-5-methylenecyclopentane; 4-hydroxymethylcyclopentane, 2,3-dihydroxy-4-hydroxymethylcyclopentane; or 2,3-dihydroxymethylcyclobutane; or a pharmaceutically acceptable salt or prodrug thereof.

In another embodiment the invention provides a compound of Formula I as described above, wherein $R^2$ is 4-hydroxymethylpyrrolidine; 2,3-dihydroxy-4-hydroxymethylpyrrolidine; 2/3-hydroxy-4-hydroxymethylpyrrolidine; 2-fluoro-3-hydroxy-4-hydroxymethylpyrrolidine; or 3-fluoro-2-hydroxy-4-hydroxymethyl-pyrrolidine; or a pharmaceutically acceptable salt or prodrug thereof.

In another embodiment the invention provides a compound of Formula I as described above, wherein $R_a$, $R_b$, $R_c$, and $R_d$ are independently selected from the group consisting of H, alkyl, and substituted alkyl; or $R_a$ and $R_b$ together with the nitrogen to which they are attached form a pyrrolidino, piperidino, piperazino, azetidino, morpholino, or thiomorpholino ring; or $R_b$ and $R_c$ together with the nitrogen to which they are attached form a pyrrolidino, piperidino, piperazino, azetidino, morpholino, or thiomorpholino ring.

In another embodiment the invention provides a compound selected from,

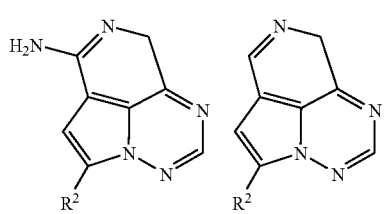

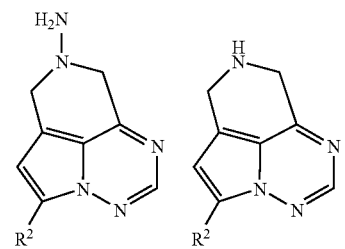

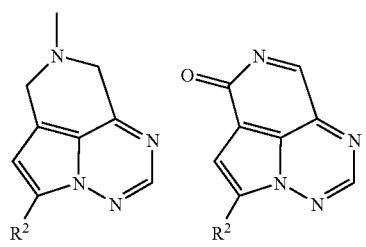

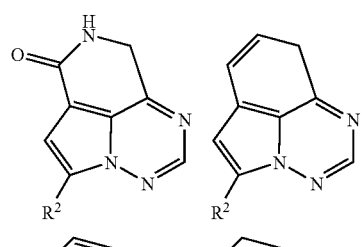

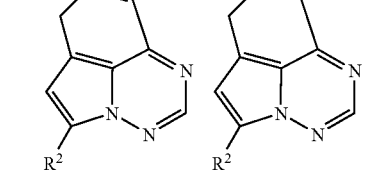

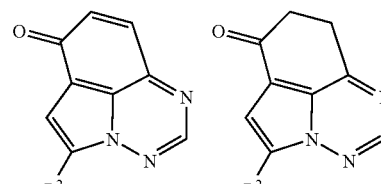

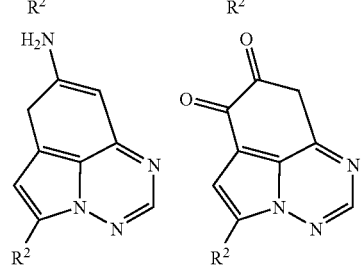

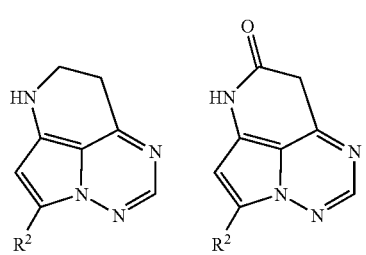

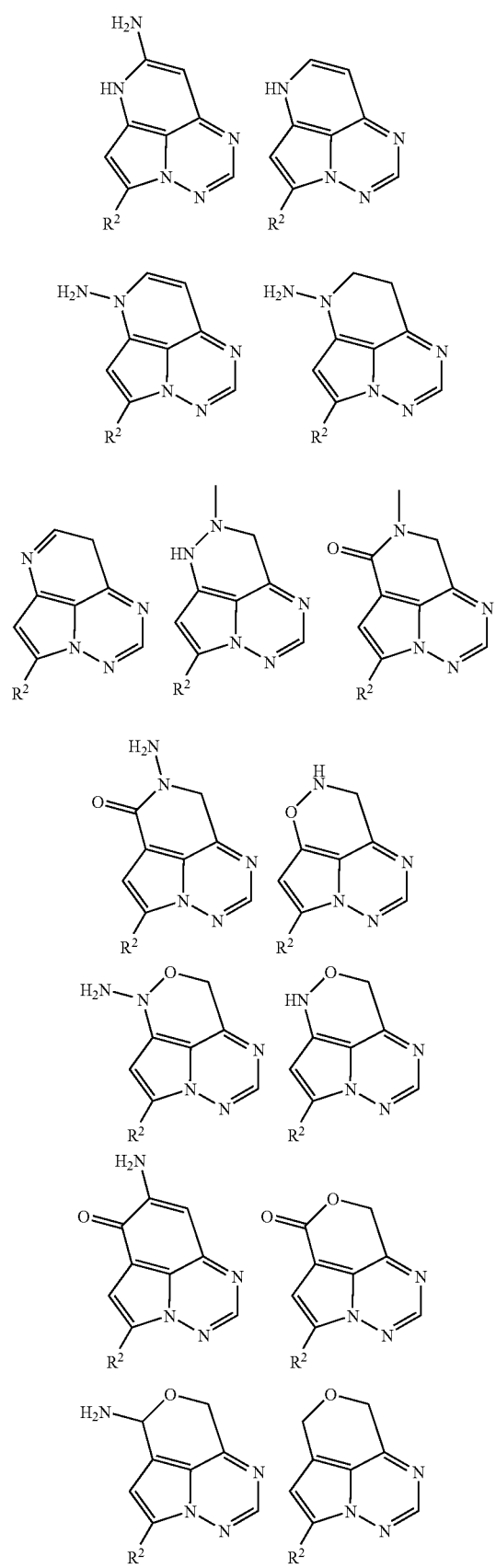
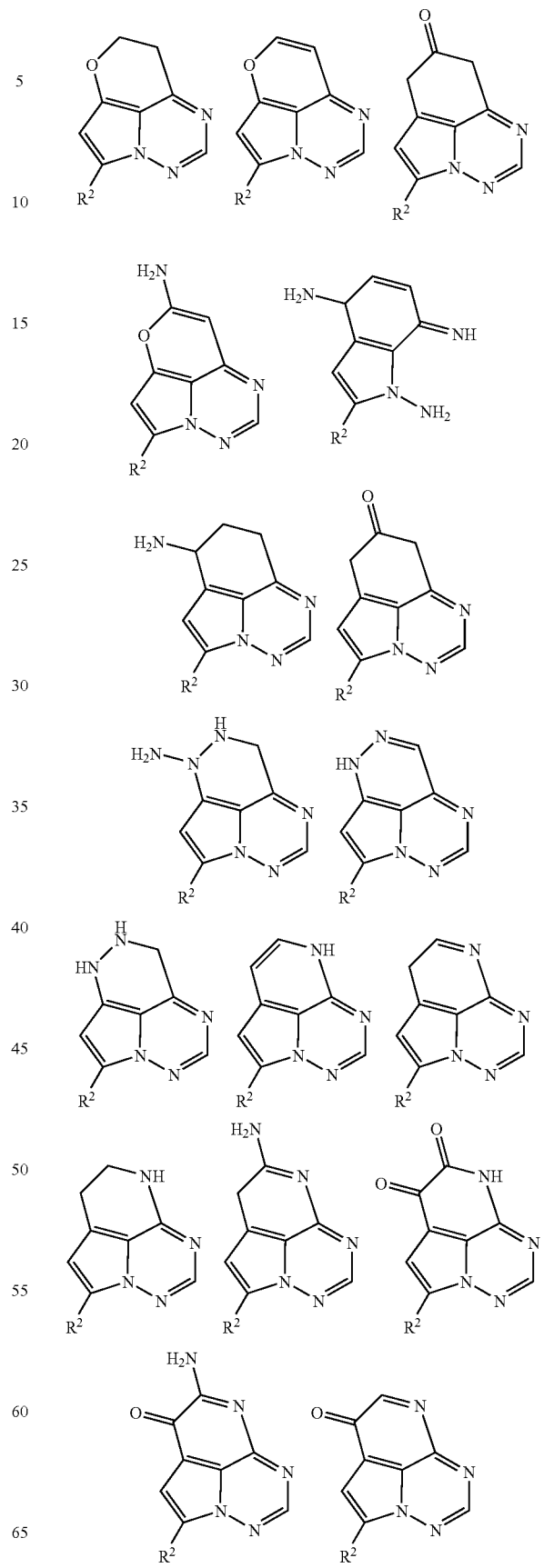

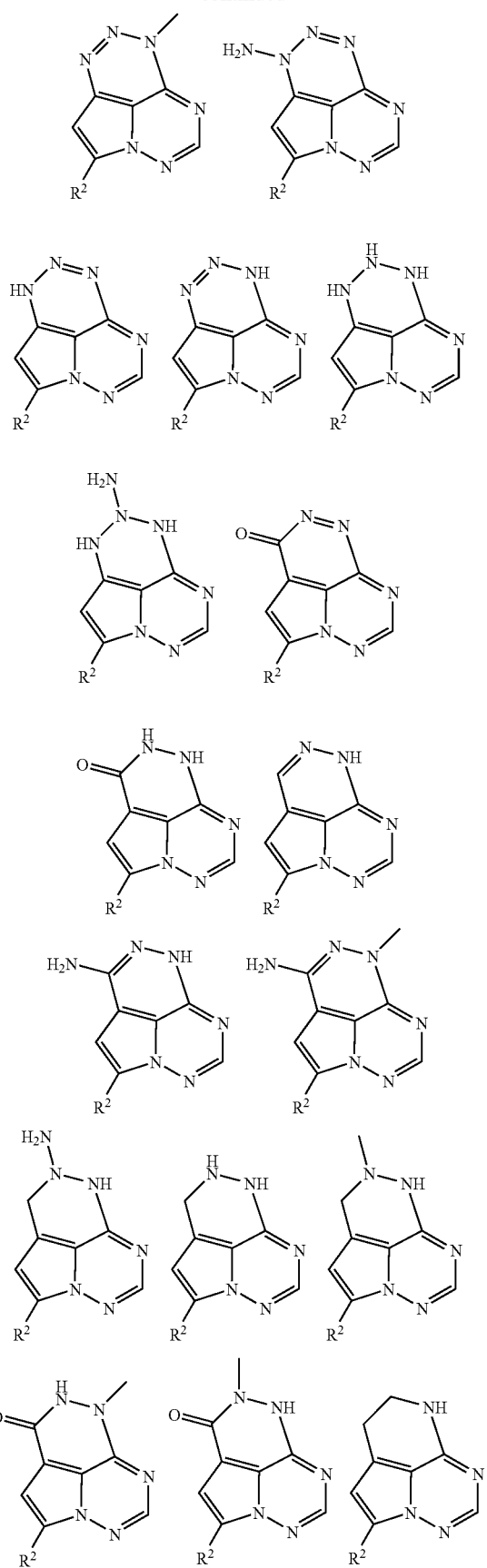
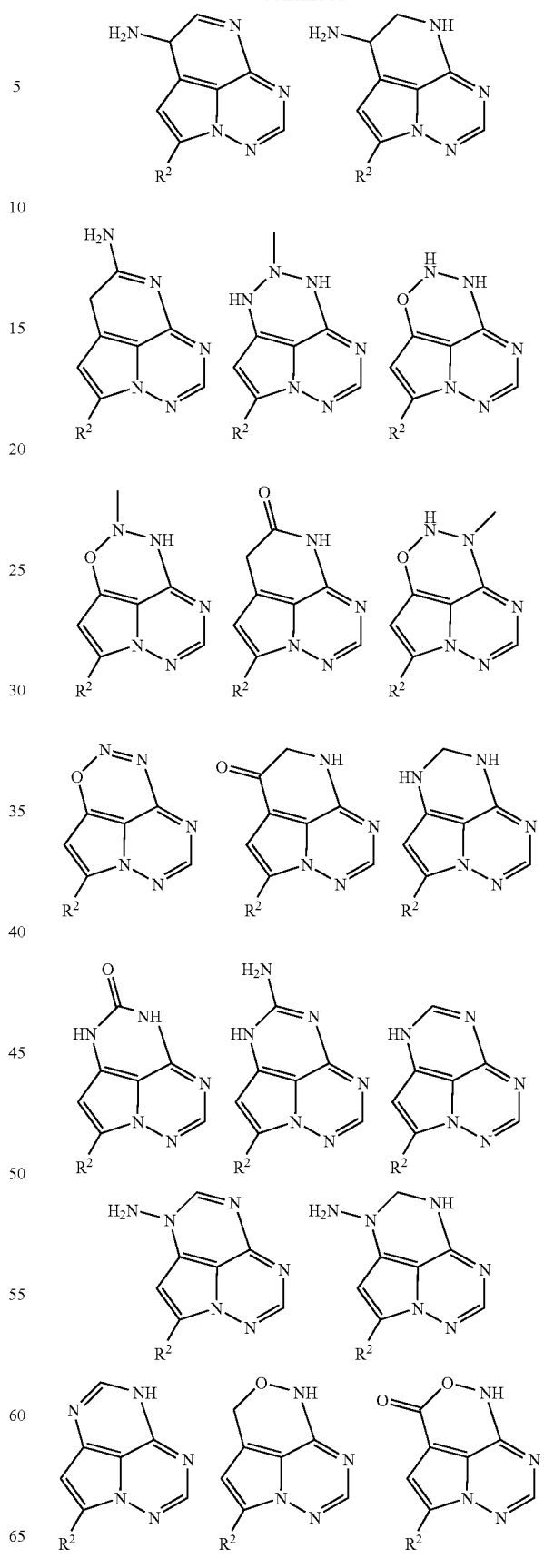

-continued
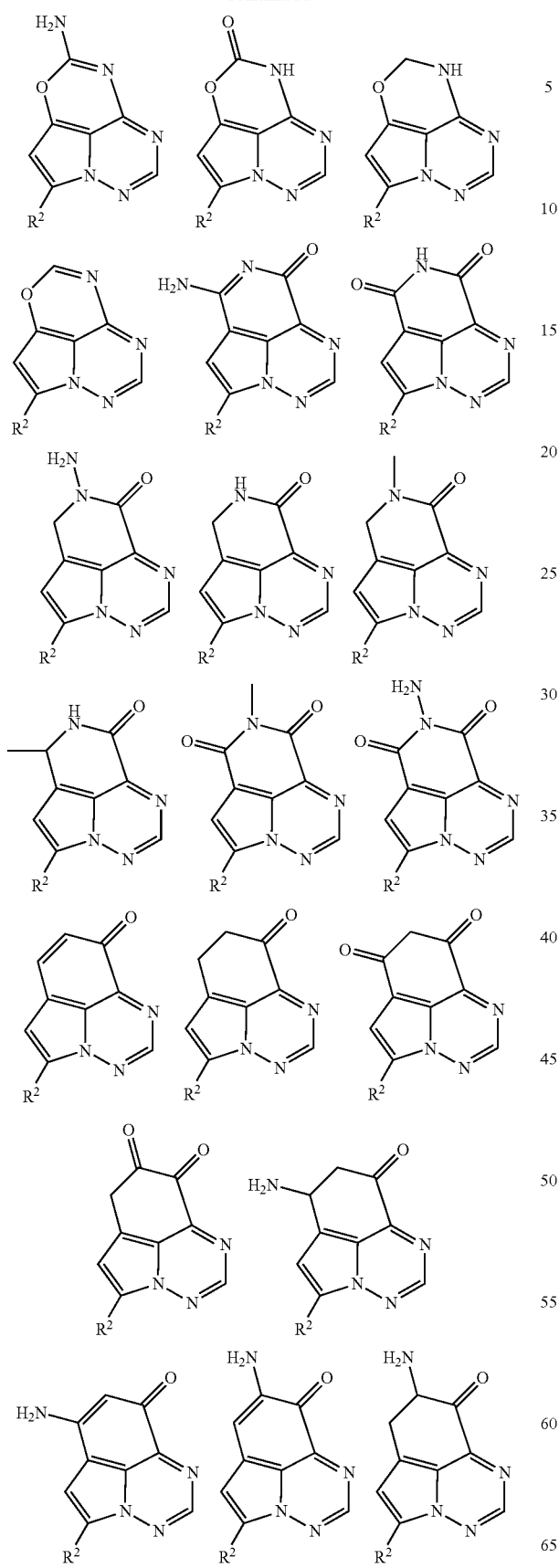
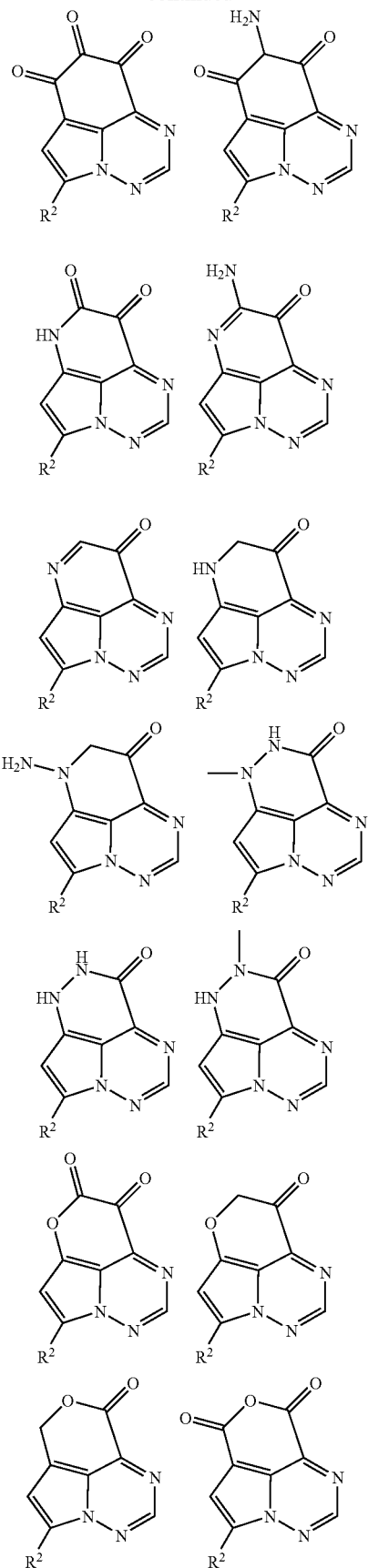

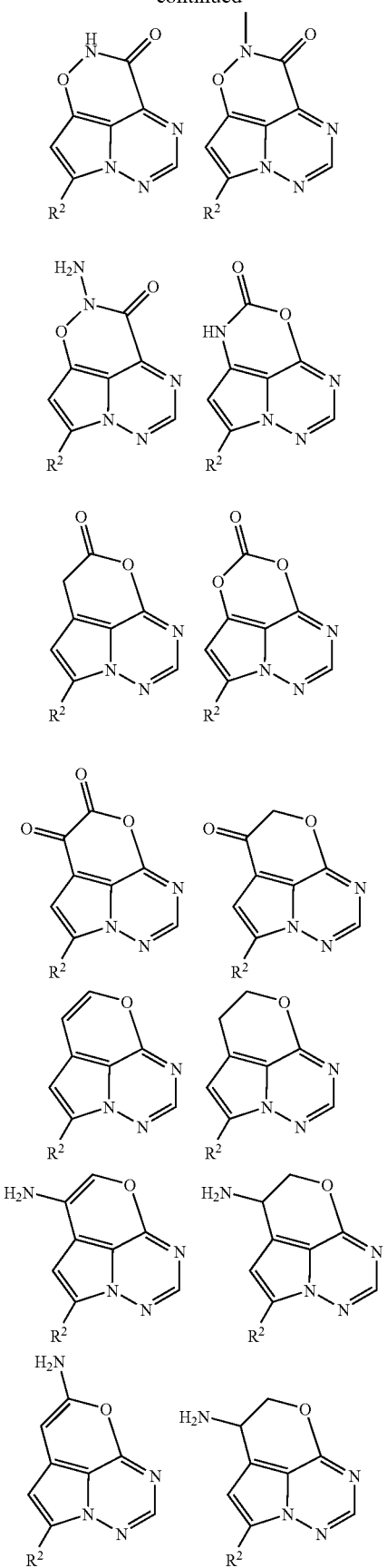
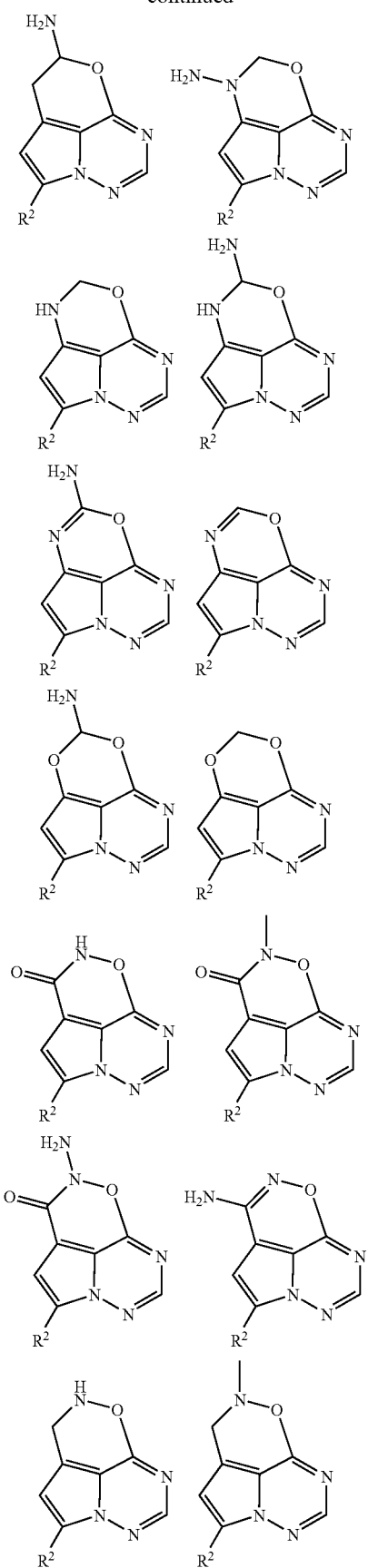

-continued
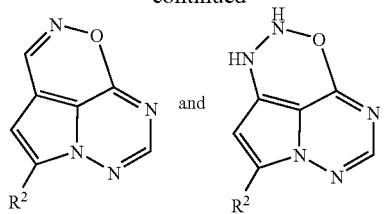
or a pharmaceutically acceptable salt or prodrug thereof.
In one embodiment the invention provides a compound of formula I selected from:
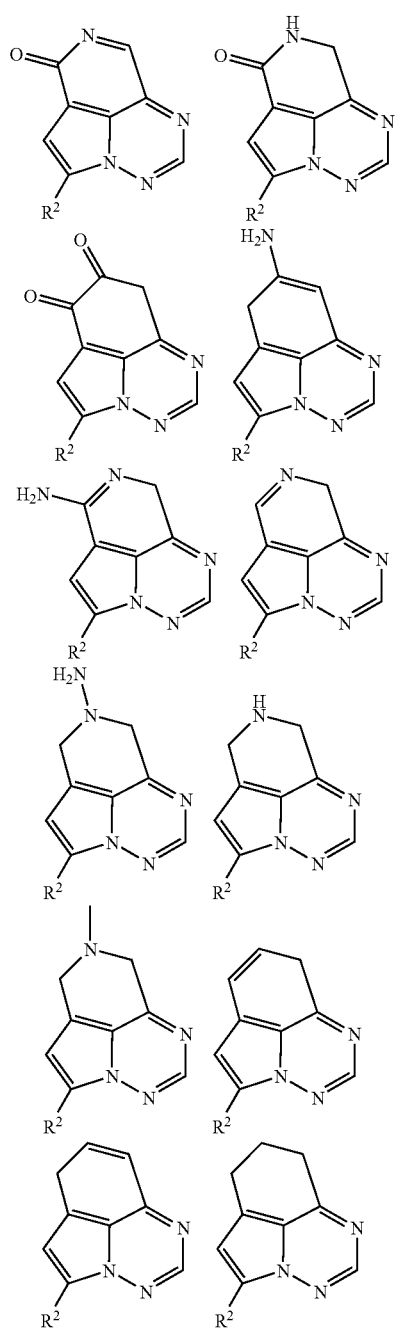
-continued
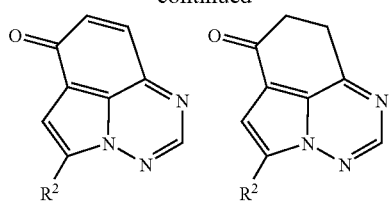
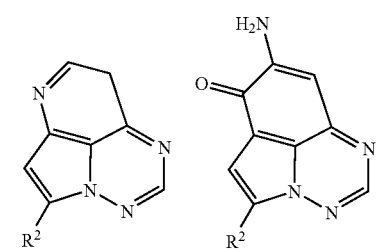
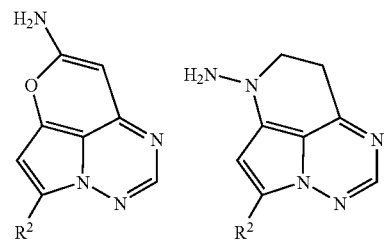
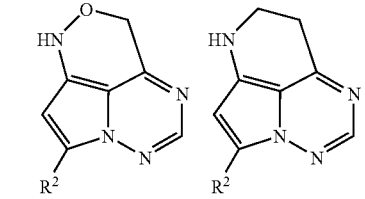
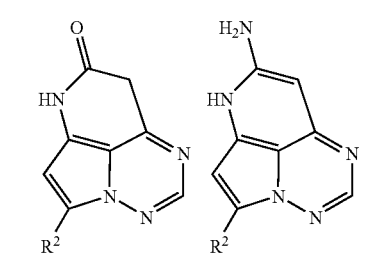
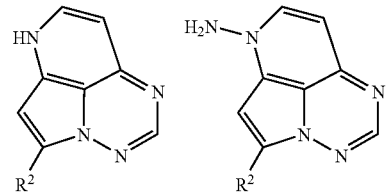
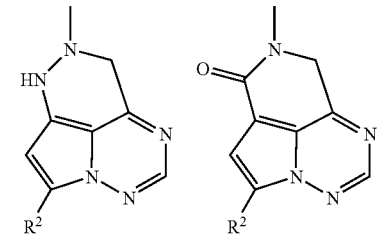

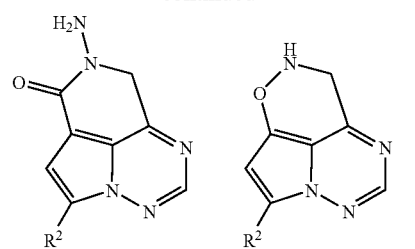
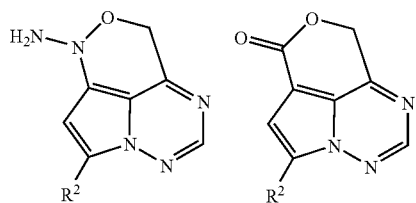
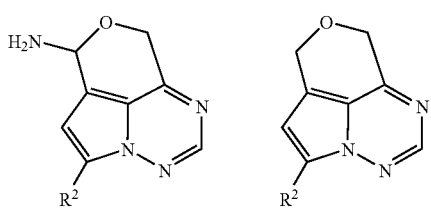
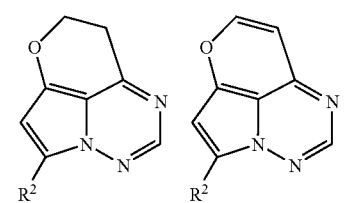
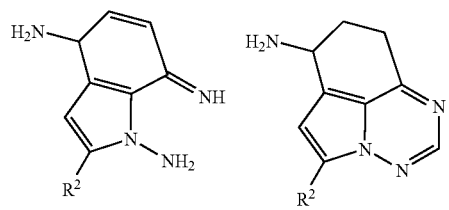
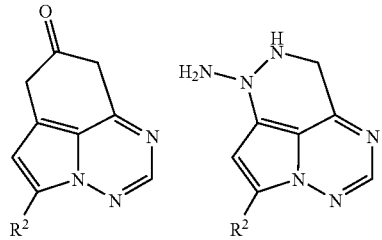
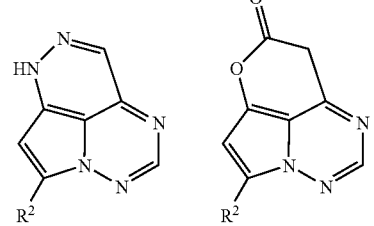
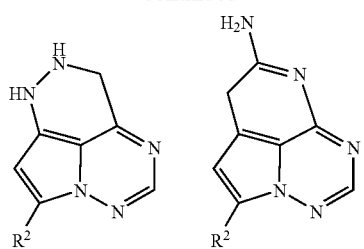
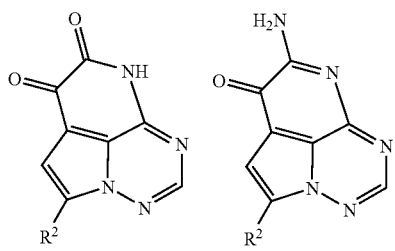
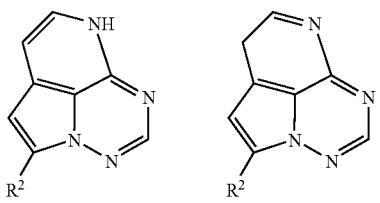
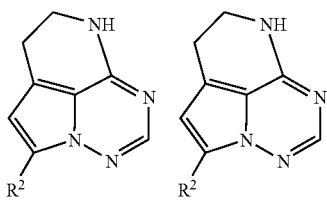
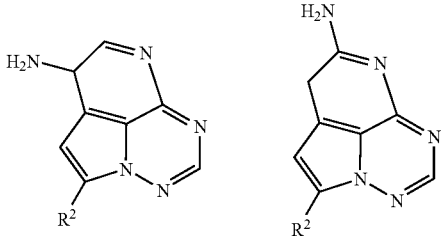
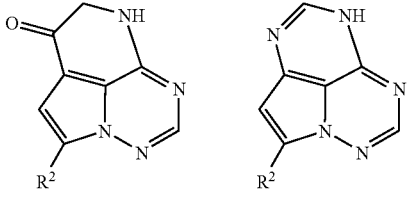
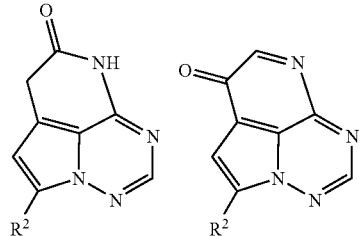

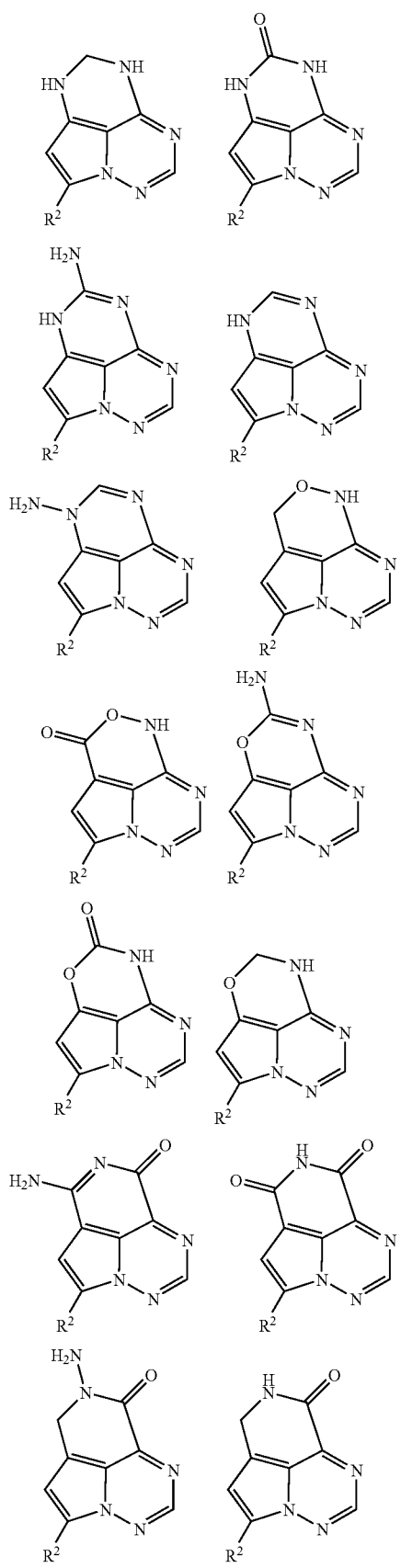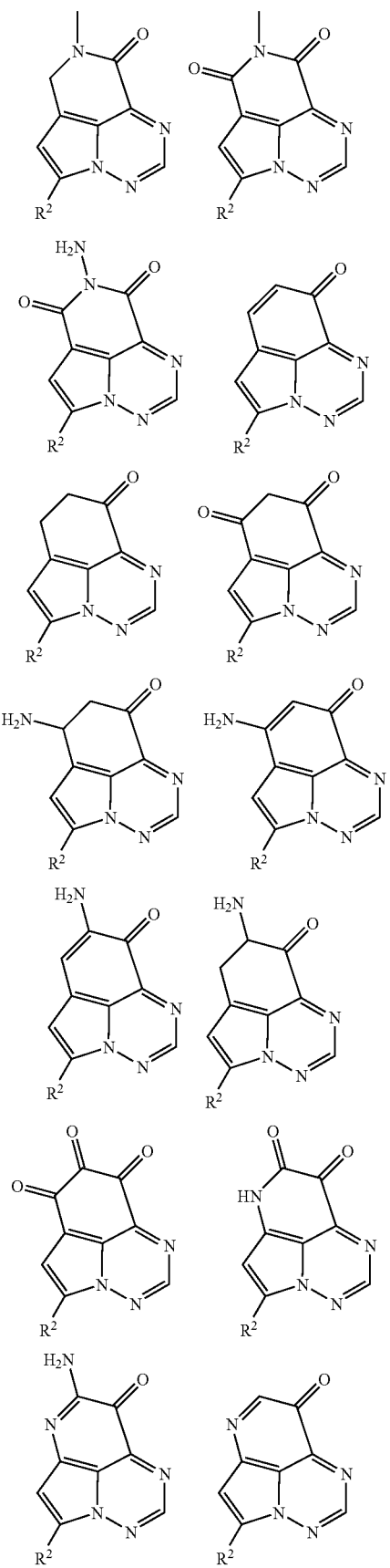

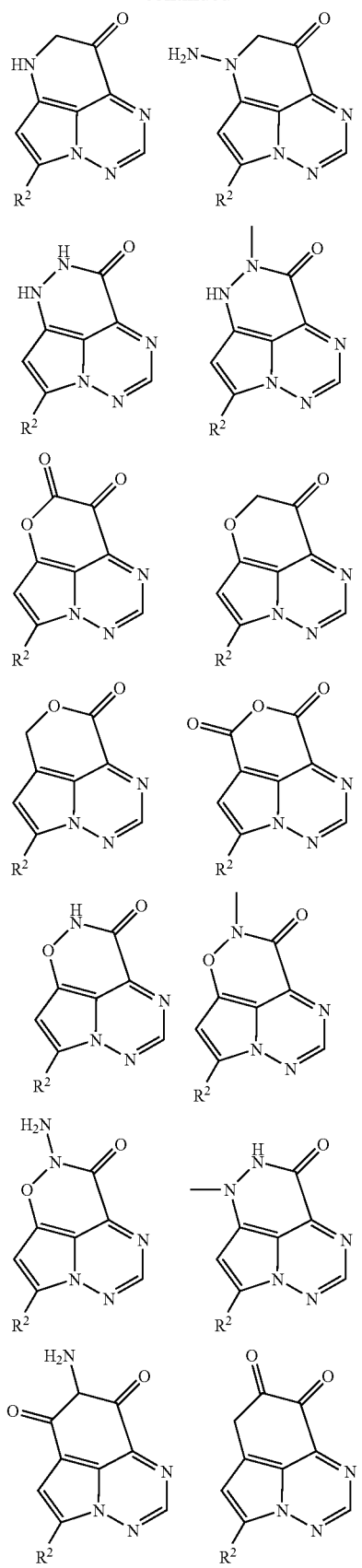
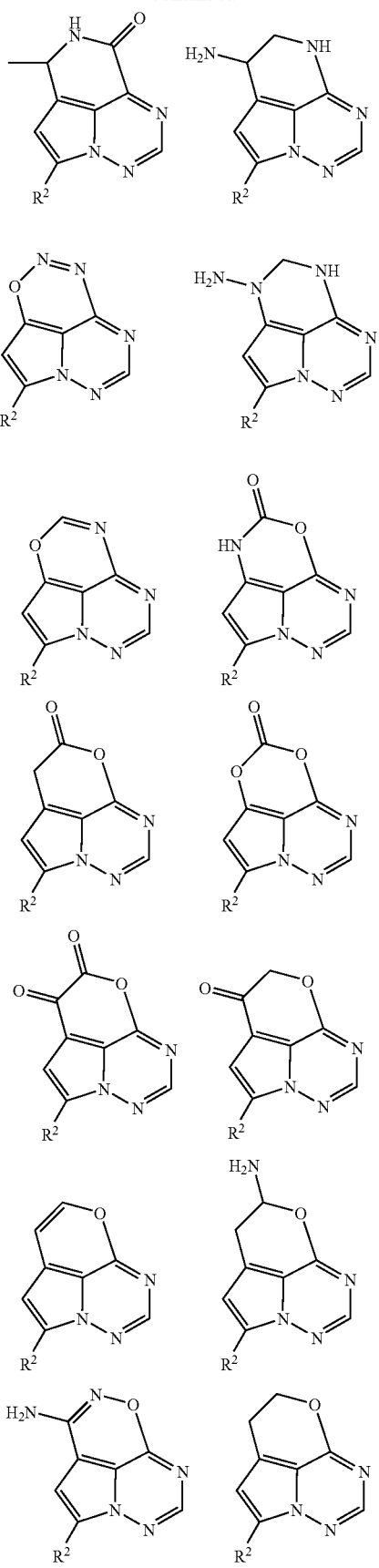

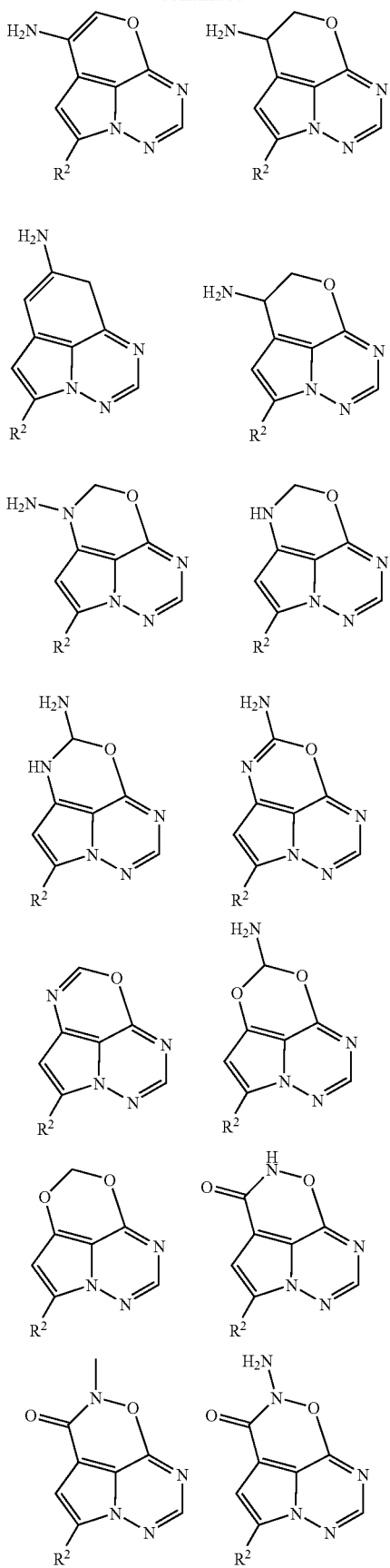

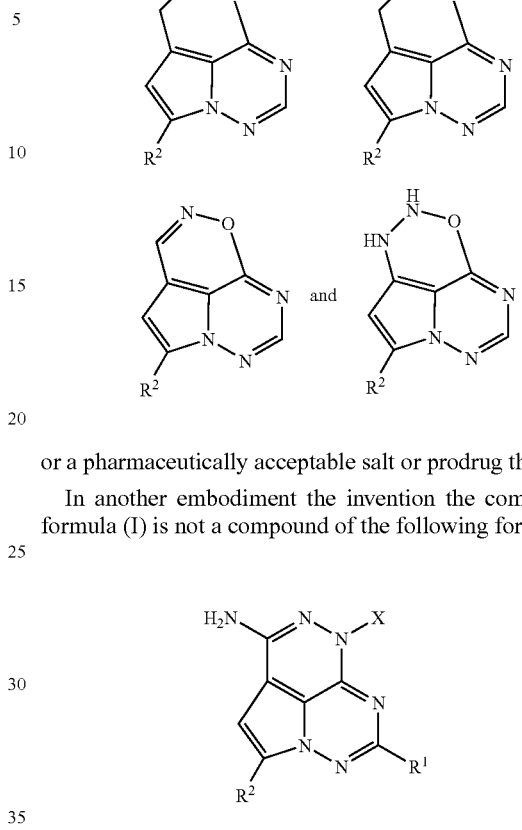

or a pharmaceutically acceptable salt or prodrug thereof.

In another embodiment the invention the compound of formula (I) is not a compound of the following formula (X):

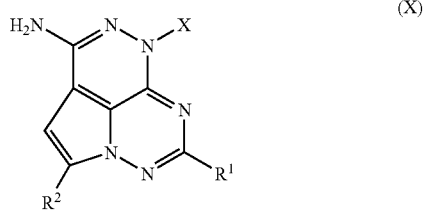

or a pharmaceutically acceptable salt or prodrug thereof; wherein X is H or alkyl.

In another embodiment the invention the compound of formula (I) is not a compound of the following formula:

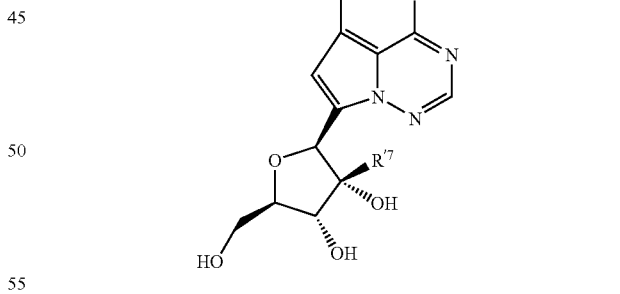

or a pharmaceutically acceptable salt or prodrug thereof; wherein X is H or methyl; and $R'^7$ is H or methyl.

In another embodiment the invention B is not a 6 membered ring comprising two nitrogens and one double bond, wherein B is substituted with $NR_cR_d$.

In another embodiment the invention B represents a 5, 7, or 8 membered ring comprising one or more heteroatoms and one or more double bonds, wherein B is optionally substituted with one or more oxo, thioxo, $NR_cR_d$, F, Cl, Br, I, $OR_z$, $SR_z$, alkyl, C≡N, C≡C—R, $N_3$ or $SO_2R'$.

In another embodiment the invention the compound of formula (I) is:

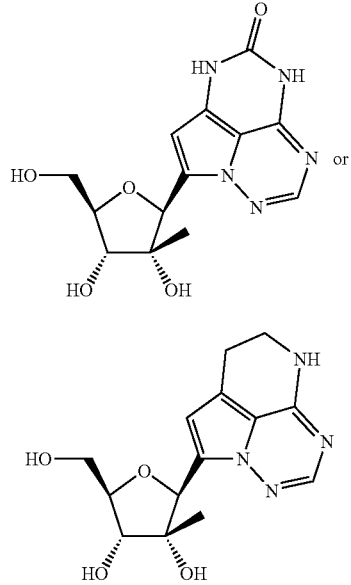
88e

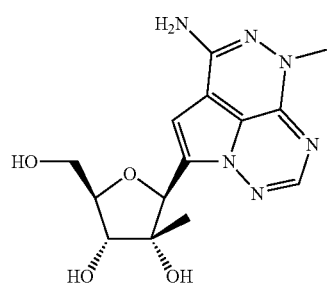
93f or a pharmaceutically acceptable salt or prodrug thereof.

In another embodiment the invention the compound of formula (I) is:

87j or a pharmaceutically acceptable salt or prodrug thereof.

In another embodiment the invention the compound of formula (I) is:

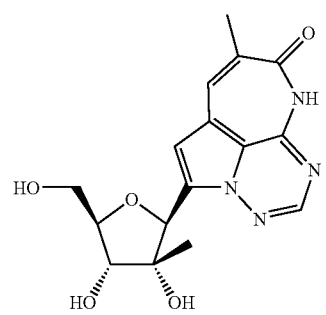
89c

-continued

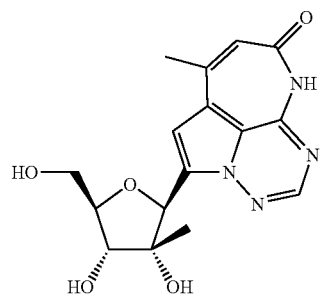
90c

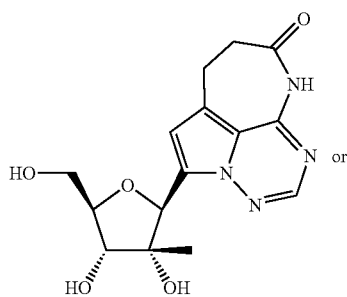
91b

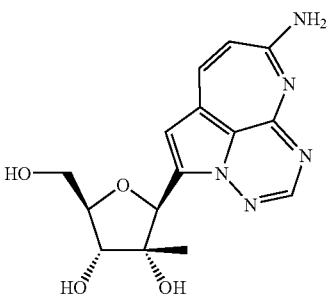
92c or a pharmaceutically acceptable salt or prodrug thereof.

In another embodiment the invention the compound of formula (I) is:

95

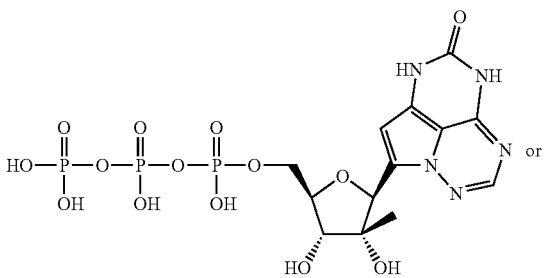

94 or a pharmaceutically acceptable salt or prodrug thereof.

In another embodiment the invention B represents a 5 membered ring comprising one or more heteroatoms (e.g. 1, 2, or 3) and one or more double bonds (e.g. 1, 2, or 3), wherein B is optionally substituted with one or more (e.g. 1, 2, or 3) oxo, thioxo, $NR_cR_d$, F, Cl, Br, I, $OR_z$, $SR_z$, alkyl, C≡N, C≡C—R, $N_3$ or $SO_2R'$.

In another embodiment the invention B represents a 6 membered ring comprising one or more heteroatoms (e.g. 1, 2, or 3) and one or more double bonds (e.g. 1, 2, or 3), wherein B is optionally substituted with one or more (e.g. 1, 2, or 3) oxo, thioxo, $NR_cR_d$, F, Cl, Br, I, $OR_z$, $SR_z$, alkyl, C≡N, C≡C—R, $N_3$ or $SO_2R'$.

In another embodiment the invention B represents a 7 membered ring comprising one or more heteroatoms (e.g. 1, 2, or 3) and one or more double bonds (e.g. 1, 2, or 3), wherein B is optionally substituted with one or more (e.g. 1, 2, or 3) oxo, thioxo, $NR_cR_d$, F, Cl, Br, I, $OR_z$, $SR_z$, alkyl, C≡N, C≡C—R, $N_3$ or $SO_2R'$.

In another embodiment the invention B represents an 8 membered ring comprising one or more heteroatoms (e.g. 1, 2, or 3) and one or more double bonds (e.g. 1, 2, or 3), wherein B is optionally substituted with one or more (e.g. 1, 2, or 3) oxo, thioxo, $NR_cR_d$, F, Cl, Br, I, $OR_z$, $SR_z$, alkyl, C≡N, C≡C—R, $N_3$ or $SO_2R'$.

Prodrugs

The term "prodrug" as used herein refers to a compound that can be metabolized in vivo to provide a compound of Formula I. Thus prodrugs include compounds that can be prepared by modifying one or more functional groups in a compound of Formula I to provide a corresponding compound that can be metabolized in vivo to provide a compound of Formula I. Such modifications are known in the art. For example, one or more hydroxy groups or amine groups in a compound of Formula I can be acylated with alkyl-C(═O)- groups or with residues from amino acids to provide a prodrug. Alternatively, one or more pendent hydroxyl groups from a mono-, di-, or tri-phosphate functionality in a compound of Formula I can be converted to an alkoxy, substituted alkoxy, aryloxy, or substituted aryloxy group.

In one embodiment, the term prodrug includes a compound wherein one or more hydroxy groups on a nucleoside sugar group (e.g. a 2', 3', or 5' hydroxy group) have been converted to a group that can be metabolized in vivo to provide a compound of Formula I. For example, the invention provides a compound wherein one or more hydroxy groups on a nucleoside sugar group (e.g. a 2', 3', or 5' hydroxy group) have been converted to an acyloxy, acylamino or R—O group, wherein R is a carboxy-linked amino acid.

In one embodiment, the term prodrug includes a compound wherein one or more pendent hydroxyl groups from a mono-, di-, or tri-phosphate functionality in a compound of Formula I is converted to a group $R_y$—O—; wherein each $R_y$ is independently a 1-20 carbon branched or unbranched, saturated or unsaturated chain, wherein one or more (e.g. 1, 2, 3, or 4) of the carbon atoms is optionally replaced with —O— or —S— and wherein one or more of the carbon atoms is optionally substituted with oxo (═O) or thioxo (═S) (See Lefebvre et al., J. Med. Chem. 1995, 38, 3941-50).

In another embodiment, the term prodrug includes a compound wherein one or more pendent hydroxyl groups from a mono-, di-, or tri-phosphate functionality in a compound of Formula I is converted to a group $R_z$—N—; wherein each $R_z$ is a residue of an amino acid. Thus, in the methods of treatment of the present invention, the term "administering" includes administration of a compound of Formula I, as well as administration of a prodrug which converts to a compound of Formula I or a salt thereof in vivo. Conventional procedures for the selection and preparation of prodrug derivatives are described, for example, in "Design of Prodrugs", ed. H. Bundgaard, Elsevier, 1985; and in International Patent Application Publication Number WO 2005/084192. A variety of prodrugs are also described in International Patent Application Number PCT US2004/013063, which was published as International Publication Number WO 2004/096286.

In another embodiment the prodrug comprises one of more groups of formula:

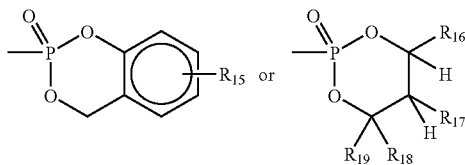

wherein:

$R_{15}$ is H, alkyl, substituted alkyl, aryl, substituted aryl, cycloalkyl, substituted cycloalkyl, heteroaryl, substituted heteroaryl, heterocyclic, substituted heterocyclic, and an amino acid;

$R_{16}$ is H, optionally substituted monocyclic aryl, or optionally substituted monocyclic heteroaryl; and $R_{17}$ is H, halogen, CN, —CO—$R_{20}$, —CON($R_{21}$)$_2$, —CO$_2R_{20}$, —SO$_2R_{20}$, —SO$_2N(R_{21})_2$, —OR$_{21}$, —SR$_{21}$, —R$_{21}$, —N($R_{21}$)$_2$, —O—COR$_{20}$, —O—CO$_2R_{20}$, —SCOR$_{20}$, —S—CO$_2R_{20}$, —NHCOR$_{21}$, —NHCO$_2R_{21}$, —(CH$_2$)$_p$—OR$_{22}$, or —(CH$_2$)$_p$—SR$_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, heterocycloalkyl, aralkyl, optionally substituted monocyclic aryl or optionally substituted monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, heterocycloalkyl, aralkyl, optionally substituted monocyclic aryl or optionally substituted monocyclic heteroaryl; and $R_{20}$ is alkyl, aryl, heterocycloalkyl, or arylalkyl;

$R_{21}$ is H, alkyl, aryl, heterocycloalkyl, or arylalkyl;

$R_{22}$ is H or lower acyl;

n is an integer from 2-5;

m is an integer from 10-20; and p is an integer from 2-3.

Prodrug forms of a compound bearing various nitrogen functions (amino, hydroxyamino, amide, etc.) may include the following types of derivatives where each $R_p$ group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined earlier.

(a) Carboxamides, represented as —NHC(O)$R_p$ (b) Carbamates, represented as —NHC(O)O$R_p$ (c) (Acyloxy)alkyl Carbamates, represented as NHC(O) OROC(O)$R_p$ (d) Enamines, represented as —NHCR(═CHCO$_2R_p$) or —NHCR(═CHCONR$_pR_p$)

(e) Schiff Bases, represented as —N═CR$_pR_p$ (f) Mannich Bases (from carboximide compounds), represented as RCONHCH$_2$NR$_pR_p$ Preparations of such prodrug derivatives are discussed in various literature sources (examples are: Alexander et al., J. Med. Chem. 1988, 31, 318; Aligas-Martin et al., PCT WO0041531, p. 30).

Prodrug forms of carboxyl-bearing compounds include esters (—CO$_2$R$_m$) where the R$_m$ group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem. 1980, 23, 469.

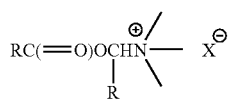

Nucleoside Sugar Groups

The term "nucleoside sugar group" as used herein includes cyclic and acyclic groups that can be included as the sugar portion of a nucleoside analog of Formula I. Many examples of such groups are known in the field of nucleoside chemistry (See for example Antiviral Drugs by John S. Driscoll (2002) published by Ashgate Publishing Ltd.).

The term nucleoside sugar group includes substituted and unsubstituted tetrahydrofuranyl and dihydrofuranyl compounds including those set forth in group (A) below, substituted and unsubstituted tetrahydrothiophenyl and dihydrothiophenyl compounds including those set forth in group (B) below, substituted and unsubstituted alkyl compounds including those set forth in group (C) below, substituted and unsubstituted cycloalkyl and cycloalkenyl compounds including those set forth in group (D) below, substituted and unsubstituted dihydropyrrolidinyl and tetrahydropyrrolidinyl compounds including those set forth in group (E) below, and substituted and unsubstituted dioxolane, substituted and unsubstituted thioxolane, and substituted and unsubstituted dithiolane compounds including those set forth in group (F) below.

Group A

Examples of substituted tetrahydro and dihydrofuranyl compounds include those compounds represented by the general structures:

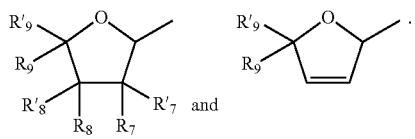

Specific examples include, but are not limited to, the following compounds:

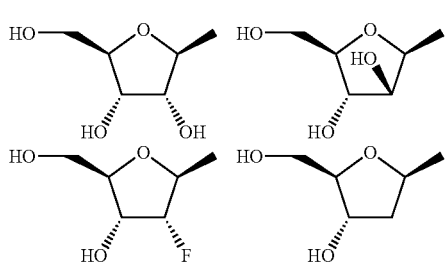

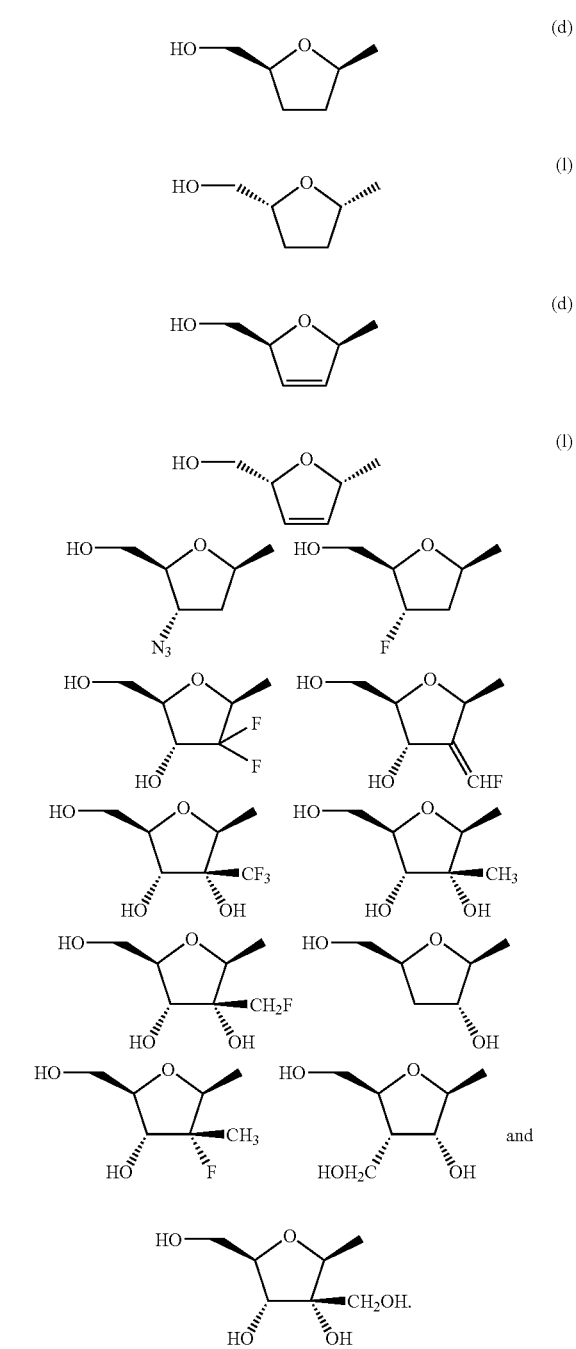

Group B

Examples of substituted tetrahydrothiophenyl and dihydrothiophenyl compounds include those compounds represented by the general structures:

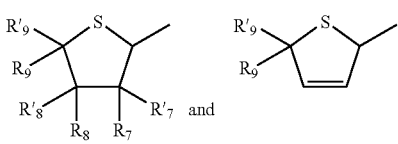

Specific examples include, but are not limited to, the following compounds:

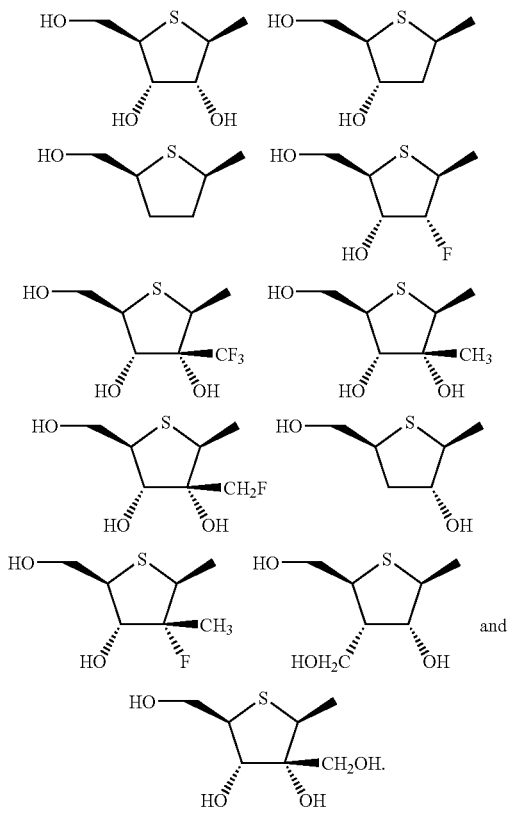

Group C

Examples of substituted alkyl compounds include those compounds represented by:

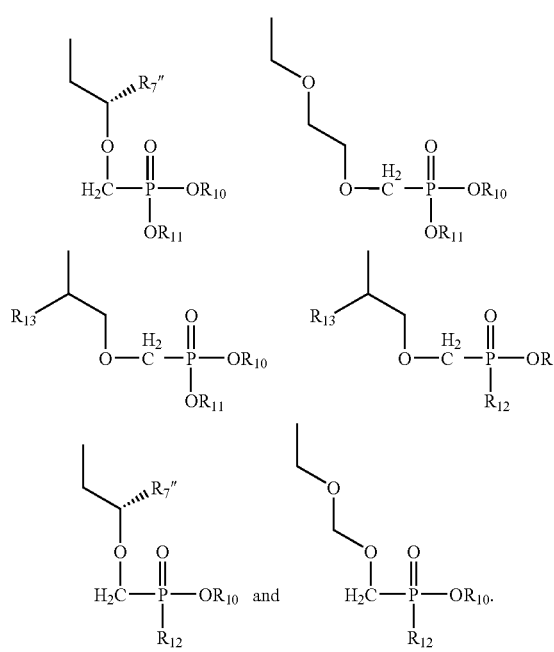

Specific examples include, but are not limited to, the following compounds:

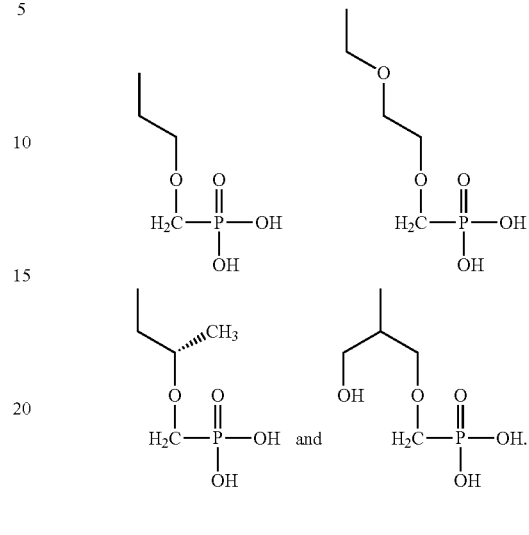

Group D

Examples of substituted cycloalkyl and cycloalkenyl compounds include those compounds represented by the general structures:

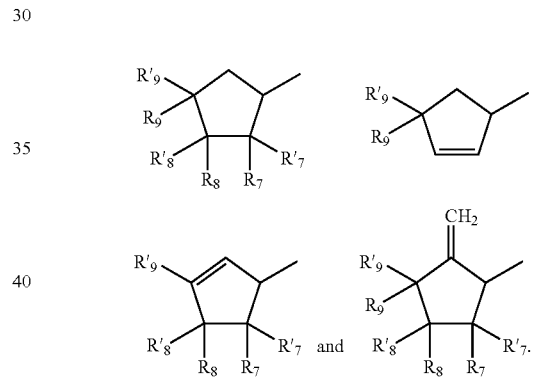

Specific examples include, but are not limited to, the following compounds:

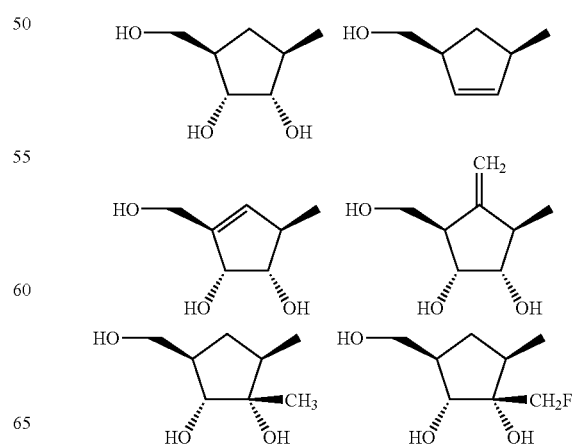

-continued

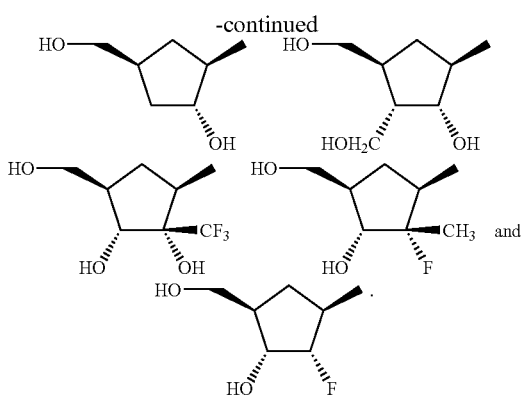

Group E
Examples of substituted dihydropyrrolidinyl and tetrahydropyrrolidinyl compounds include those compounds represented by the general structures:

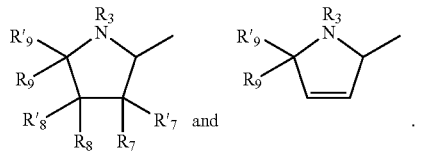

Specific examples include, but are not limited to, the following compounds:

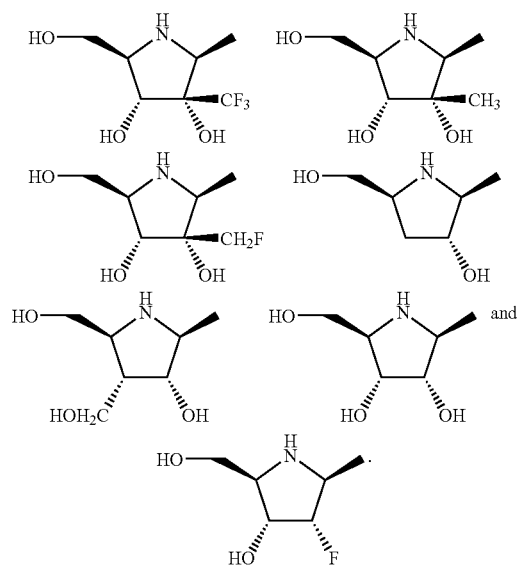

Group F
Examples of substituted dioxolane, substituted thioxolane and substituted dithiolane compounds include those compounds represented by the general structures:

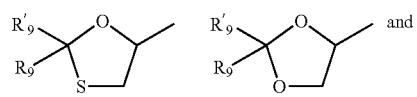

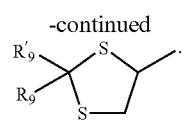

Specific examples include, but are not limited to, the following compounds:

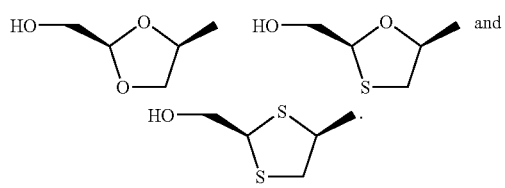

For the structures in Groups A-F, the following definitions apply:

$R_7$ is H, $OR_{14}$, $N_3$, $NH_2$, or F; and $R'_7$ is H, F, OH, O-alkyl, alkyl, substituted alkyl, alkenyl, substituted alkenyl, alkynyl, or substituted alkynyl; or $R_7$ and $R'_7$ together may be $=CH_2$, $=CHF$; wherein both $R_7$ and $R'_7$ are not OH; and when one of $R_7$ and $R'_7$ is $NH_2$, the other is not OH; and when one of $R_7$ and $R'_7$ is $N_3$, the other is not OH;

$R_8$ is H, $OR_{14}$, $N_3$, $NH_2$, or F; and $R'_8$ is H, F, OH, O alkyl, alkyl, substituted alkyl, alkenyl, substituted alkenyl, alkynyl, or substituted alkynyl; or $R_8$ and $R'_8$ together may be $=CH_2$, $=CHF$; wherein both $R_8$ and $R'_8$ are not OH; and when one of $R_8$ and $R'_8$ is $NH_2$, the other is not OH; and when one of $R_8$ and $R'_8$ is $N_3$, the other is not OH;

or $R_7$ and $R_8$ together can form

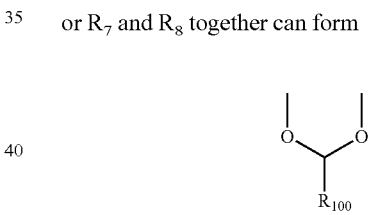

wherein: $R_{100}$ is $C_{1-12}$ alkyl $C_{3-8}$ cycloalkyl, aryl or heteroaryl; wherein any $C_{1-12}$ alkyl and $C_{3-8}$ cycloalkyl of $R_{100}$ is unsubstituted or is substituted with 1-3 substituents selected from halogen, hydroxy, carboxy, and $C_{1-4}$ alkoxy; and wherein any aryl or heteroaryl of $R_{100}$ is unsubstituted or is substituted with 1-5 substituents independently selected from $R_{101}$;

each $R_{101}$ is independently halo, $C_{1-4}$ alkyl, $C_{1-4}$ alkoxy, $C_{1-4}$ alkylthio, $C_{1-4}$ alkylsulfoyl, cyano, nitro, amino, phenyl, carboxy, trifluoromethyl, trifluoromethoxy, $C_{1-4}$ alkylamino, di($C_{1-4}$ alkyl)amino, $C_{1-4}$ alkanoyl, $C_{1-4}$ alkanoyloxy, or $C_{1-4}$ alkyloxycarbonyl;

$R_9$ is H, $CH_3$, $C_2H_5$, or $N_3$;

$R'_9$ is $CH_2OR_{14}$, $CH_2F$, $CH_2SH$, $CHFOH$, $CF_2OH$, $CH_2$-diphosphate, $CH_2$-triphosphate,

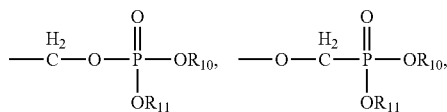

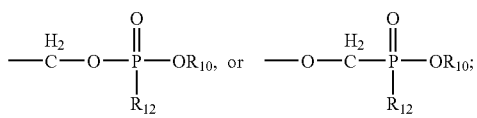

$R_{10}$ and $R_{11}$ are each independently H, alkyl, aryl, substituted aryl, acyloxyalkyl, or $(CH_2)_n$—O—$(CH_2)_m CH_3$;

$R_{12}$ is an N-linked amino acid residue (e.g. —NH—CH($CH_3$)$CO_2$alkyl or —NH—CH(isopropyl)-$CO_2$alkyl); and $R_{14}$ is H;

n is 2-5; and m is 10-20.

In one specific embodiment of the invention for the structures in Groups A-F:

$R_7$ is H, $OR_{14}$, $N_3$, $NH_2$, or F; and $R'_7$ is H, F, OH, O-alkyl, alkyl, substituted alkyl, alkenyl, substituted alkenyl, alkynyl, or substituted alkynyl; or $R_7$ and $R'_7$ together may be =$CH_2$, =CHF; wherein both $R_7$ and $R'_7$ are not OH; and when one of $R_7$ and $R'_7$ is $NH_2$, the other is not OH; and when one of $R_7$ and $R'_7$ is $N_3$, the other is not OH; $R_7''$ is alkyl or substituted alkyl.

$R_8$ is H, $OR_{14}$, $N_3$, $NH_2$, or F; and $R'_8$ is H, F, OH, O alkyl, alkyl, substituted alkyl, alkenyl, substituted alkenyl, alkynyl, or substituted alkynyl; or $R_8$ and $R'_8$ together may be =$CH_2$, =CHF; wherein both $R_8$ and $R'_8$ are not OH; and when one of $R_8$ and $R'_8$ is $NH_2$, the other is not OH; and when one of $R_8$ and $R'_8$ is $N_3$, the other is not OH;

$R_9$ is H, $CH_3$, $C_2H_5$, or $N_3$;

$R'_9$ is $CH_2OR_{14}$, $CH_2F$, $CH_2SH$, CHFOH, $CF_2OH$,

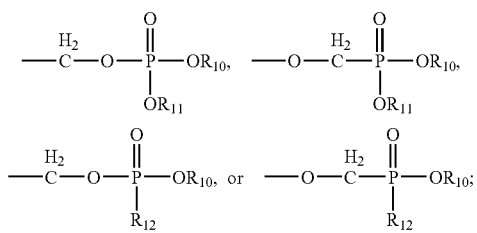

$R_{10}$ and $R_{11}$ are each independently H, alkyl, aryl, substituted aryl, acyloxyalkyl, or $(CH_2)_n$—O—$(CH_2)_m CH_3$;

$R_{12}$ is an N-linked amino acid residue (e.g. —NH—CH($CH_3$)$CO_2$alkyl or —NH—CH(isopropyl)-$CO_2$alkyl);

$R_{13}$ is H, $CH_3$, $C_2H_5$, $CH_2F$, $CH_2OH$, $CH_2CH_2F$, $CH_2CH_2OH$, $CH_2N_3$, $CH_2CH_2N_3$, $CH_2NH_2$, or $CH_2CH_2NH_2$;

$R_{14}$ is H;

n is 2-5; and m is 10-20.

In one embodiment, for a compound of Formula I, $R_{14}$ is replaced to form a pharmaceutically acceptable prodrug, for example, a prodrug selected from the group consisting of: acyl, oxyacyl, phosphonate, phosphate, phosphate esters, phosphonamidate, phosphorodiamidate, phosphoramidate mono ester, cyclic phosphoramidate, cyclic phosphorodiamidate, phosphoramidate diester, C(O)CHR$_{15}$NH$_2$,

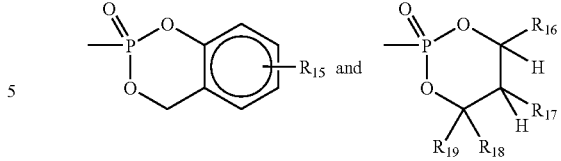

wherein:

$R_{15}$ is H, alkyl, substituted alkyl, aryl, substituted aryl, cycloalkyl, substituted cycloalkyl, heteroaryl, substituted heteroaryl, heterocyclic, substituted heterocyclic, or an amino acid;

$R_{16}$ is H, optionally substituted monocyclic aryl, or optionally substituted monocyclic heteroaryl; and $R_{17}$ is H, halogen, CN, —CO—$R_{20}$, —CON($R_{21}$)$_2$, —$CO_2R_{20}$, —$SO_2R_{20}$, —$SO_2N(R_{21})_2$, —$OR_{21}$, —$SR_{21}$, —$R_{21}$, —N($R_{21}$)$_2$, —O—$COR_{20}$, —O—$CO_2R_{20}$, —$SCOR_{20}$, —S—$CO_2R_{20}$, —$NHCOR_{21}$, —$NHCO_2R_{21}$, —$(CH_2)_p$—$OR_{22}$, or —$(CH_2)_p$—$SR_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, heterocycloalkyl, aralkyl, optionally substituted monocyclic aryl or optionally substituted monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, heterocycloalkyl, aralkyl, optionally substituted monocyclic aryl or optionally substituted monocyclic heteroaryl; and $R_{20}$ is alkyl, aryl, heterocycloalkyl, or arylalkyl;

$R_{21}$ is H, alkyl, aryl, heterocycloalkyl, or arylalkyl;

$R_{22}$ is H or lower acyl; and p is an integer from 2-3.

Synthetic Processes

Processes for preparing compounds of Formula I, or a pharmaceutically acceptable salts or prodrugs thereof, as well as processes for preparing intermediate compounds that can be used to prepare compounds of Formula I or pharmaceutically acceptable salts or prodrugs thereof are provided as further embodiments of the invention. For example in one embodiment the invention provides a method for preparing a pharmaceutically acceptable salt of compound of Formula I comprising converting a corresponding compound of Formula I to the salt.

In another embodiment the invention provides a method for preparing a prodrug of a compound of Formula I comprising converting a corresponding compound of Formula I to the prodrug.

In another embodiment the invention provides a method for preparing a compound of Formula I comprising deprotecting a corresponding compound of Formula I that comprises one or more protecting groups to provide the compound of Formula I.

Synthetic Intermediates

The invention also provides synthetic intermediates that are useful for preparing compounds of Formula I or a salt or prodrug thereof. For example, the invention provides novel synthetic intermediates such as those described in the Examples herein.

Isomers and Physical Forms

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixtures thereof, of a compound of the invention (e.g. a compound of Formula I, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-viral or anti-cancer activity using the standard tests described herein, or using other similar tests which are well known in the art. Although the invention includes all isomeric forms of the compounds described herein, one embodiment of the invention provides compounds having the absolute stereochemistry depicted in the Examples hereinbelow.

Pharmaceutical Compositions, Modes of Administration and Methods of Treatment

The present disclosure provides compounds of the general Formula I as detailed above which are inhibitors of DNA and/or RNA viral polymerases and anticancer agents. Various forms of DNA and RNA viral polymerases are inhibited by the compounds disclosed, such as but not limited to viral RdRps. The compounds of the present disclosure therefore have utility in treating and/or preventing viral infections in a host and in treatment and/or preventing a variety of disease states and/or conditions caused by or related to such viral infections. In one embodiment, the compounds are useful in the above mentioned treating and/or preventing by inhibiting a viral RNA and DNA polymerases. Such viral agents include, but are not limited to, hepatitis B, hepatitis C, human immunodeficiency virus, Polio, Coxsackie A and B, Rhino, Echo, small pox, Ebola, and West Nile virus. In a particular embodiment, the causative agent of the viral infection is a flavivirus.

The present disclosure provides for a compound of the general Formula I and a pharmaceutical composition comprising a pharmaceutically effective amount of at least one compound of general Formula I as described herein. Such compounds and/or pharmaceutical compositions may be used in the manufacture of a medicament for treating and/or preventing a disease or condition in which it is desirable to inhibit a viral RNA and DNA polymerases. Such pharmaceutical compositions may also comprise a pharmaceutically acceptable carrier and other ingredients known in the art, or may comprise solely a compound of the general Formula I.

The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds described in the instant disclosure can be administered by any conventional method available for use in conjunction with pharmaceuticals, either as individual therapeutic agents or in combination with additional therapeutic agents.

The compounds described are administered in a pharmaceutically effective amount. The pharmaceutically effective amount of the compound and the dosage of the pharmaceutical composition administered will, of course, vary depending upon known factors, such as the pharmacodynamic characteristics of the particular agent and its mode and route of administration; the age, health and weight of the recipient; the severity and stage of the disease state or condition; the kind of concurrent treatment; the frequency of treatment; and the effect desired.

A daily dosage of active ingredient can be expected to be about 0.001 to 1000 milligrams (mg) per kilogram (kg) of body weight per day. In one embodiment, the total amount is between about 0.1 mg/kg and about 100 mg/kg of body weight per day; in an alternate embodiment between about 1.1 mg/kg and about 50 mg/kg of body weight per day; in yet another alternate embodiment between 0.1 mg/kg and about 30 mg/kg of body weight per day. The above described amounts may be administered as a series of smaller doses over a period of time if desired. The pharmaceutically effective amount can be calculated based on the weight of the parent compound to be delivered. If the salt or prodrug exhibits activity in itself, the pharmaceutically effective amount can be estimated as above using the weight of the salt or prodrug, or by other means known to those skilled in the art. The dosage of active ingredient may be given other than daily if desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

Dosage forms of the pharmaceutical compositions described herein (forms of the pharmaceutical compositions suitable for administration) contain from about 0.1 mg to about 3000 mg of active ingredient (i.e. the compounds disclosed) per unit. In these pharmaceutical compositions, the active ingredient will ordinarily be present in an amount of about 0.5-95% weight based on the total weight of the composition. Multiple dosage forms may be administered as part of a single treatment. The active ingredient may be administered to achieve peak plasma concentrations of the active ingredient of from about 0.2 to 70 µM, or from about 1.0 to 10 µM.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation via the pulmonary system, such as by propellant based metered dose inhalers or dry powders inhalation devices. Other dosage forms are potentially possible such as administration transdermally, via patch mechanisms or ointment.

Formulations suitable for oral administration can include (a) liquid solutions, such as a pharmaceutically effective amount of the compound dissolved in diluents, such as water, saline, or orange juice; (b) capsules, sachets, tablets, lozenges, and troches, each containing a predetermined pharmaceutically effective amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives.

The compound can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl .beta.-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include pastilles comprising the active ingredient in an inert base, such as gelatin and glycerin, or sucrose and acacia, as well as creams, emulsions, and gels containing, in addition to the active ingredient, such carriers as are known in the art. Furthermore, transdermal patches can be prepared using methods known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an patient are available, and, although more than one route can be used to administer a particular compound, a particular route can provide a more immediate and more effective reaction than another route.

Useful embodiments of pharmaceutical dosage forms for administration of the compounds according to the present invention can be illustrated as follows:

A large number of hard-shell capsules are prepared by filling standard two-piece hard gelatine capsules each with 100 mg of powdered active ingredient, 150 mg of lactose, 50 mg of cellulose and 6 mg of magnesium stearate.

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate release tablets/capsules are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

In one embodiment, the teachings of the present disclosure provide for the use of such pharmaceutical compositions and medicaments in a method of treating a viral infection or treating a disease state and/or condition caused by or related to such viral infection. In one embodiment, the treatment is the result of the inhibition of a viral RNA or DNA polymerase, such as but not limited to a RdRp. Such treatment or inhibition need not be complete to be useful. The method of treatment comprises the steps of: (i) identifying a patient in need of such treatment; (ii) providing such pharmaceutical composition containing at least one compound of the invention; and (iii) administering such pharmaceutical composition in a therapeutically effective amount to treat the viral infection in a patient in need of such treatment or to inhibit the activity of a viral RNA or DNA polymerase in a patient in need of such treatment.

In one embodiment, the teachings of the present disclosure provide for the use of such pharmaceutical compositions and medicaments in a method of preventing or suppressing a viral infection or preventing or suppressing a disease state and/or condition caused by or related to such viral infection. In one embodiment, the prevention or suppression is the result of the inhibition of a viral RNA or DNA polymerase, such as but not limited to a RdRp. Such prevention, suppression or inhibition need not be complete to be useful. The method of preventing or suppressing can optionally comprises the steps of: (i) identifying a patient in need of such prevention; (ii) providing such pharmaceutical composition containing at least one compound of the general Formula I; and (iii) administering such pharmaceutical composition in a therapeutically effective amount to prevent or suppress the viral infection in a patient in need of such treatment or to inhibit the activity of a viral RNA and DNA polymerase in a patient in need of such treatment.

The methods of the treating and preventing a viral infection or a disease state and/or condition caused by or related to said viral infection may further comprise administering a therapeutically effective amount of a compound of the present invention in combination with a therapeutically effective amount of another anti-viral agent which, in particular, may be active against HCV. Agents active against HCV include, but are not limited to, ribavirin, levovirin, viramidine, thymosin alpha-1, an inhibitor of HCV NS3 serine protease, an inhibitor of inosine monophosphatedehydrognease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a, interferon-α2b, a consensus interferon, and a purified interferon-α product.

The compounds and pharmaceutical compositions of the present disclosure can be administered to patients to prevent and/or treat a number of cancers. Cancers include, but are not limited to, leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The cancer may be related to a viral infection or an activity of a viral DNA or RNA polymerase.

The methods of the treating and preventing cancer may also comprises further administering of a chemotherapeutic agent in combination with any of the compounds or pharmaceutical compositions of the present disclosure. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, azaserine, thioguanine, floxuridine, fludarabine, cladribine and L-asparaginase.

Examples of chemotherapeutic agents that are natural products include actinomycin D, bleomycin, camptothecins, daunomycin, doxorubicin, etoposide, mitomycin C, TAXOL™ (paclitaxel), taxotere, teniposide, vincristine, vinorelbine, mithramycin, idarubicin, MITHRACIN™. (plicamycin), and deoxycoformycin.

An example of a hormonal chemotherapeutic agent includes tamoxifen. Examples of the aforesaid miscellaneous chemotherapeutic agents include mitotane, mitoxantrone, vinblastine, and levamisole.

The ability of a compound to inhibit viral polymerases can be evaluated using known assays. The ability of a compound to inhibit HCV NS5B polymerase can be evaluated using the following assay.

HCV NS5B Polymerase Assay

Antiviral activity of the test compounds was assessed (Okuse et al, Antiviral Res. 2005, 65, 23-34) in the stably HCV RNA-replicating cell line, AVA5, derived by transfection of the human hepatoblastoma cell line, Huh7 (Blight et al., Sci. 2000, 290, 1972). Compounds were added to dividing cultures once daily for three days. Media was changed with each addition of compound. Cultures generally started the assay at 30-50% confluence and reached confluence during the last day of treatment. Intracellular HCV RNA levels and cytotoxicity were assessed 24 hours after the last dose of compound.

Triplicate cultures for HCV RNA levels (on 48-well and 96-well plates) and cytotoxicity (on 96-well plates) were used. A total of six untreated control cultures, and triplicate cultures treated with α-interferon and ribavirin served as positive antiviral and toxicity controls.

Intracellular HCV RNA levels were measured using a conventional blot hybridization method in which HCV RNA levels are normalized to the levels of B-actin RNA in each individual culture (Okuse et al., Antivir. Res. 2005, 65, 23-34). Cytotoxicity was measured using a neutral red dye uptake assay (Korba and Gerin, Antivir. Res. 1992, 19, 55). HCV RNA levels in the treated cultures are expressed as a percentage of the mean levels of RNA detected in untreated cultures.

A representative compound of Formula I demonstrated significant activity in this assay.

Compound Synthesis

Compounds of Formula I can be prepared using synthetic intermediates and synthetic procedures that are known, or they can be prepared using the synthetic intermediates and synthetic procedures described herein, for example, as described in the following Schemes.

The following abbreviations are used herein.
Tr: trityl
Bn: benzyl
TBDPS: tert-butyldiphenylsilyl
m-CPBA: 3-chloroperoxybenzoic acid
TFA: trifluoroacetic acid
TBDMSCl: tert-butyldimethylsilyl chloride
DMF: dimethylformamide
THF: tetrahydrofuran
LDA: lithium diisopropylamine
TEAB: triethylammonium bicarbonate
MmTrCl: monomethoxytrityl chloride
MMTrCl: monomethoxytrityl chloride
DMAP: dimethylaminopyridine
DEAE: diethylaminoethyl-sepharose
CMA-80: Chloroform 80:MeOH 18:$NH_4OH$:2
CMA-50: Chloroform 50:MeOH 40:$NH_4OH$:10
Bz: benzoyl
BnBr: benzyl bromide
LiHMDS: lithium hexamethyldisalazane
TBDPSCl: tert-butyldiphenylsilyl chloride
DMSO: dimethylsulfoxide
RMgBr: alkyl magnesium bromide
DIBAL: diisobutylaluminum hydride
DBN: 1,5-diazabicyclo[4.3.0]non-5-ene
DBU: 1,8-diazabicyclo[5.4.0]undec-7-ene
MeMgBr: methylmagnesium bromide
P: Represents a suitable protecting group
R: In Schemes 41-86 R can have any of the values defined for $R^2$ herein

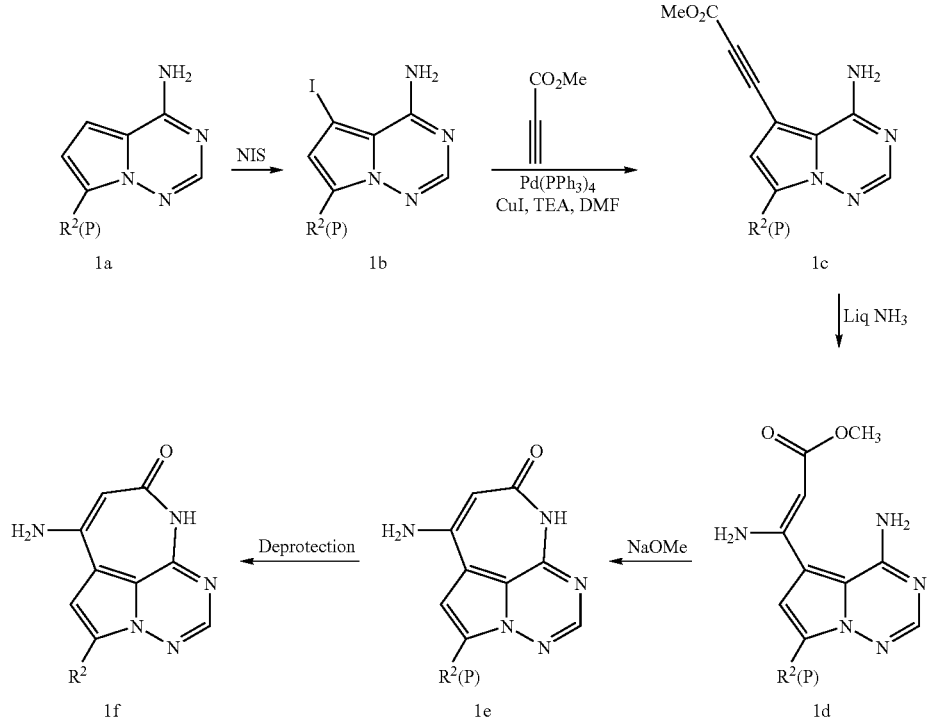

Scheme 1

Synthesis of a compound of formula 1; where $X^1$ = O, $Y^1$ = $NH_2$, $Z^1$ = H, $R^1$ = H (1f)

Scheme 2
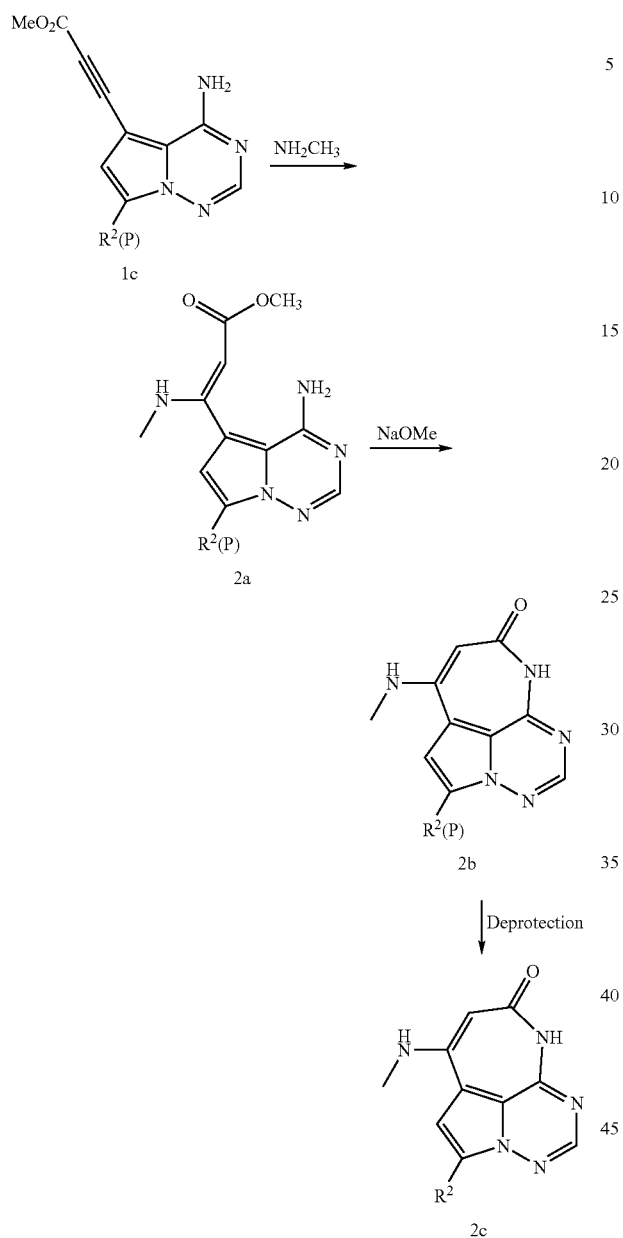
Synthesis of a compound of formula 1; where $X^1 = O$, $Y^1 = NHCH_3$, $Z^1 = H$, $R^1 = H$ (2c)
Scheme 3
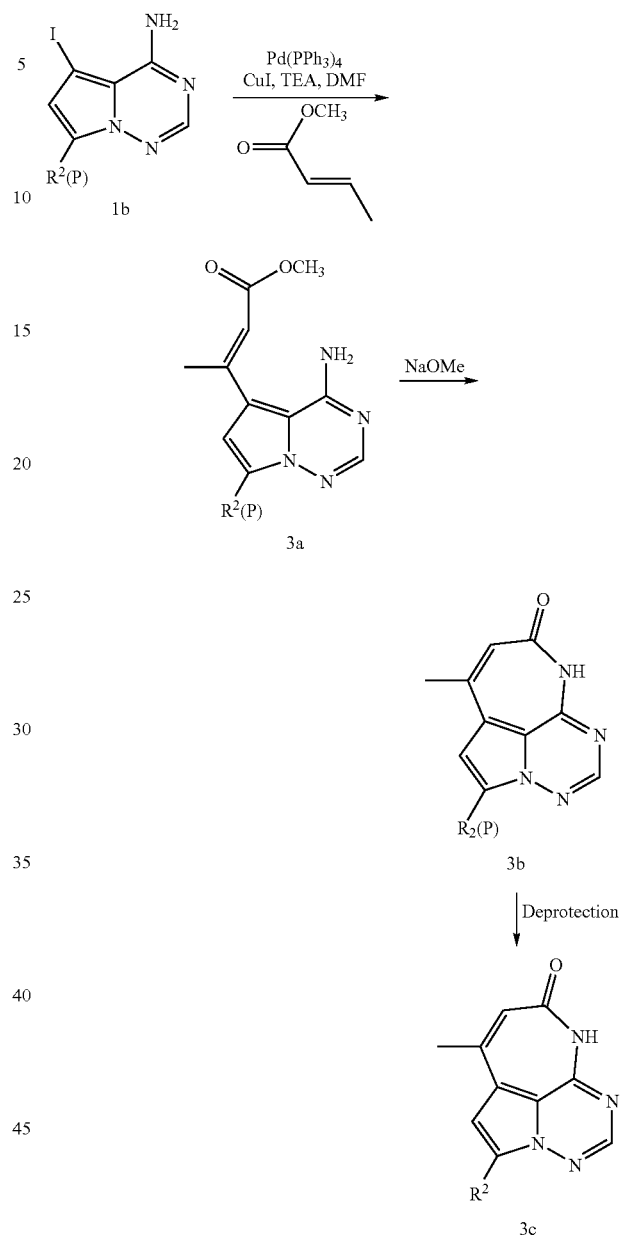
Synthesis of a compound of formula 1; where $X^1 = O$, $Y^1 = CH_3$, $Z^1 = H$, $R^1 = H$ (3c)
Scheme 4
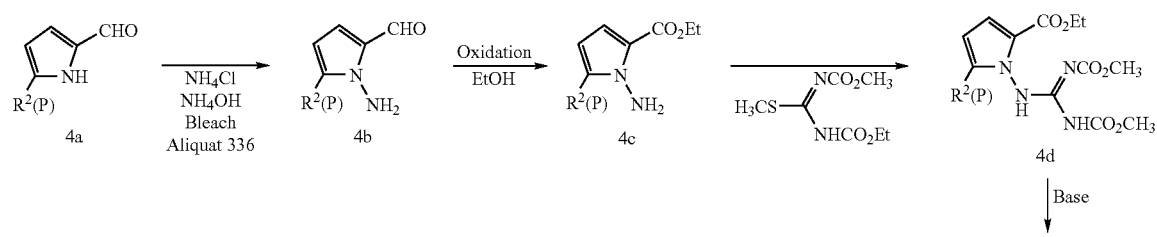

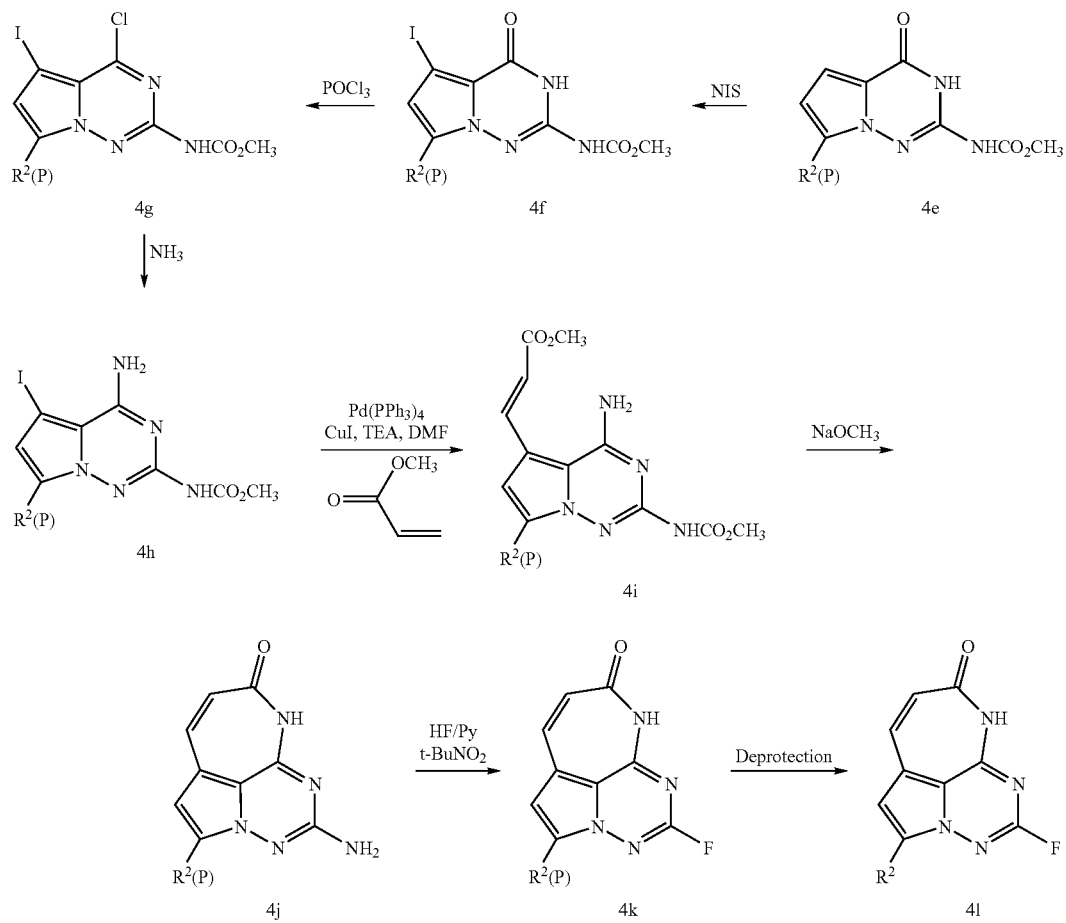
Synthesis of a compound of formula 1; where $X^1 = O$, $Y^1 = Z^1 = H$, $R^1 = F$ (4l)
Scheme 5
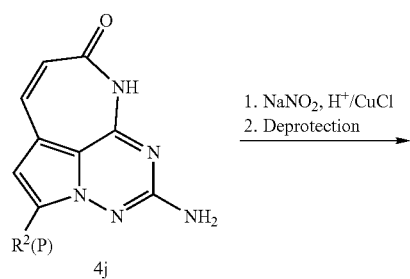
Scheme 6
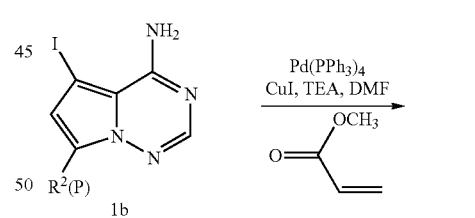
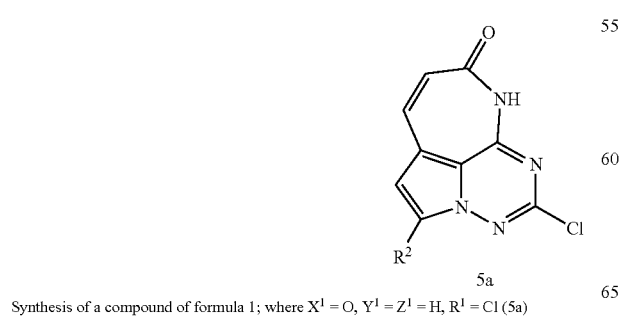
Synthesis of a compound of formula 1; where $X^1 = O$, $Y^1 = Z^1 = H$, $R^1 = Cl$ (5a)
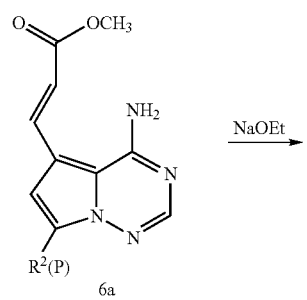

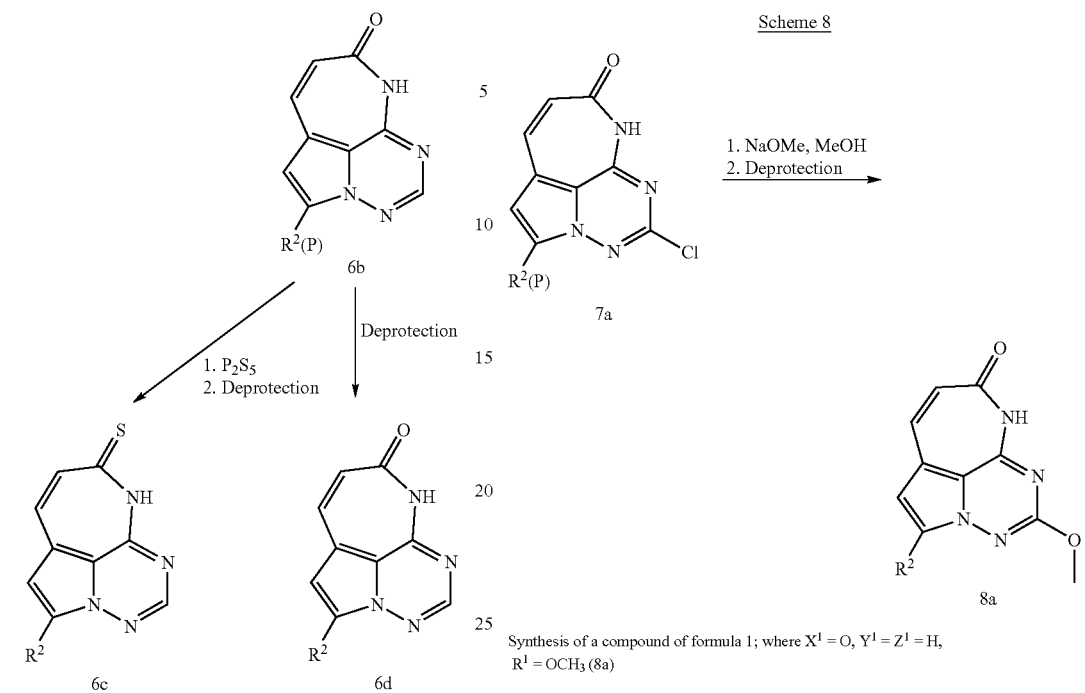
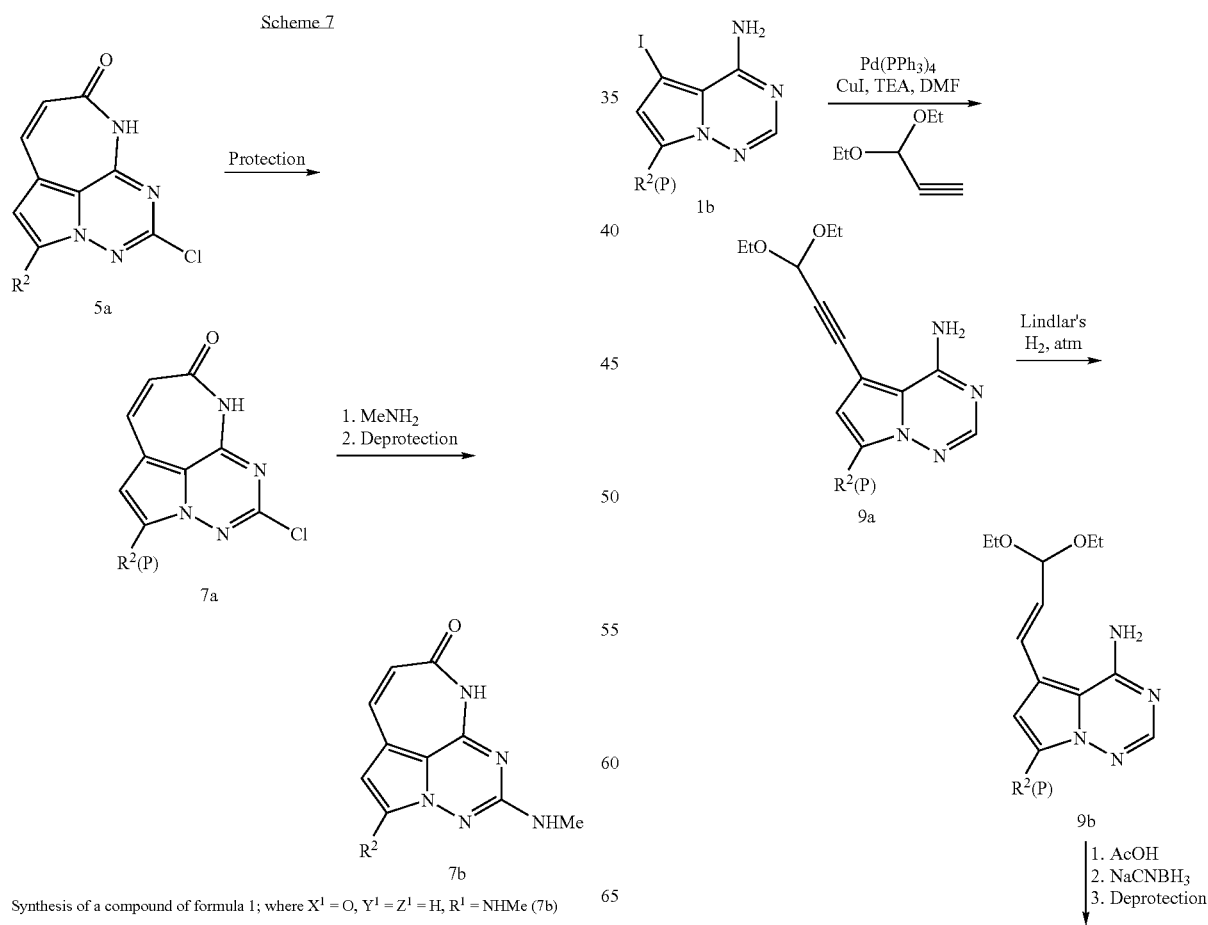

59
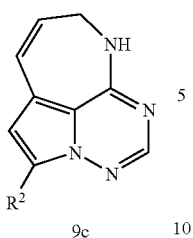
9c
Synthesis of a compound of formula 1; where $X^1$ = two hydrogens, $Y^1 = Z^1$ = H, $R^1$ = H (9c)
Scheme 10
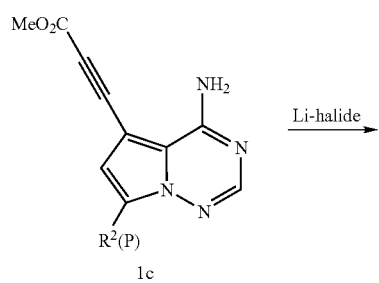
1c
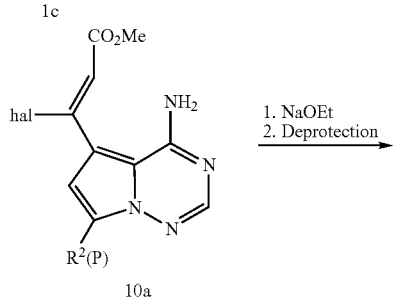
10a
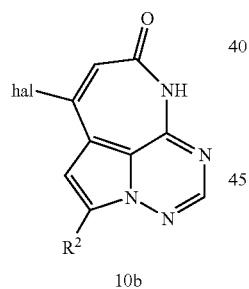
10b
Synthesis of a compound of formula 1; where $X^1$ = O, $Z^1$ = H, $Y^1$ = hal = halogen, $R^1$ = H (10b)
Scheme 11
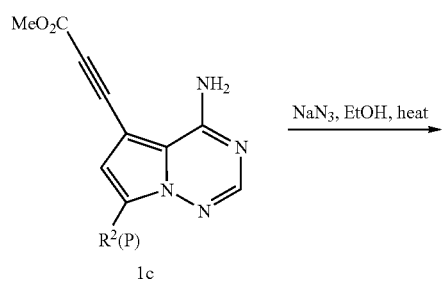
1c
60
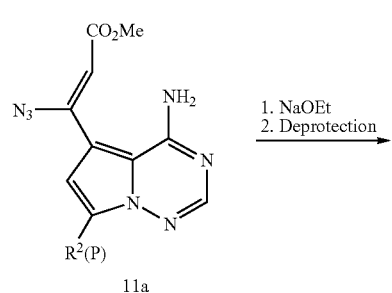
11a
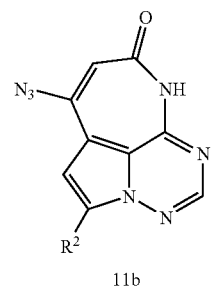
11b
Synthesis of a compound of formula 1; where $X^1$ = O, $Y^1 = N_3$, $Z^1$ = H, $R^1$ = H (11b)
Scheme 12
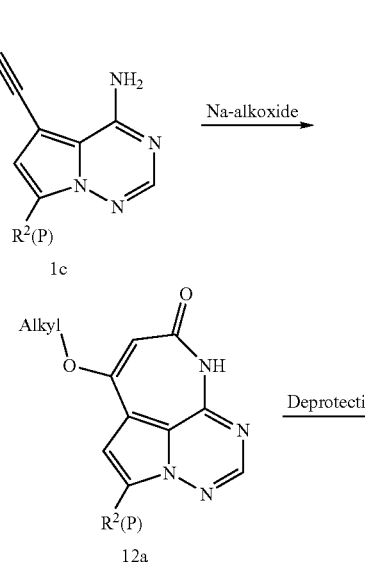
1c
12a
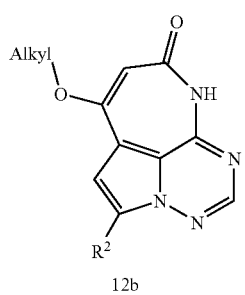
12b
Synthesis of a compound of formula 1; where $X^1$ = O, $Y^1$ = O-alkyl, $Z^1$ = H, $R^1$ = H (12b)

Scheme 13
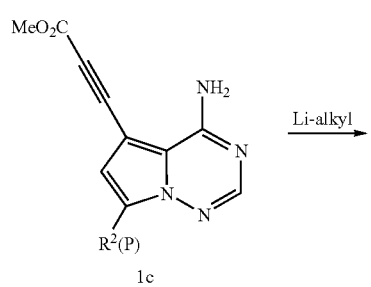
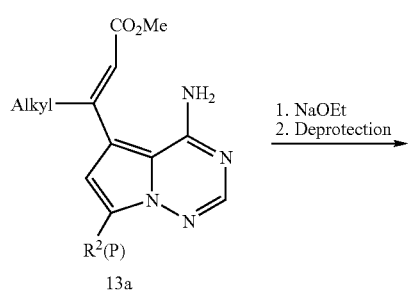
Synthesis of a compound of formula 1; where $X^1 = O$, $Y^1 = $ alkyl, $Z^1 = H$, $R^1 = H$ (13b)
Scheme 14
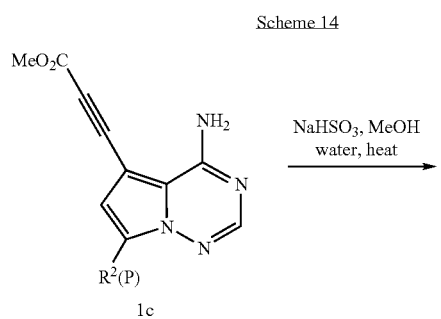
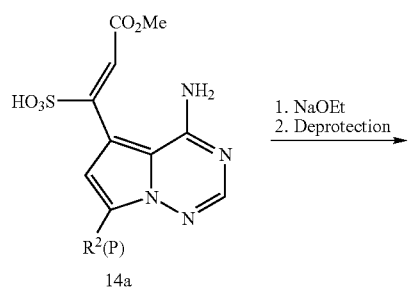
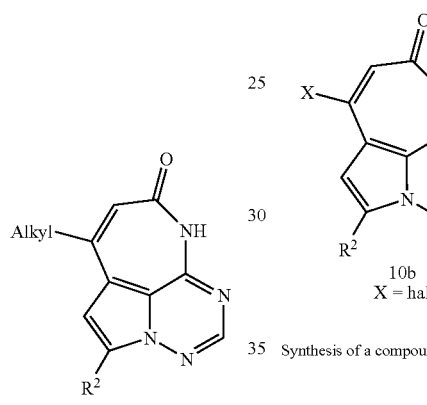
Synthesis of a compound of formula 1; where $X^1 = O$, $Y^1 = SO_3H$, $Z^1 = H$, $R^1 = H$ (14b)
Scheme 15
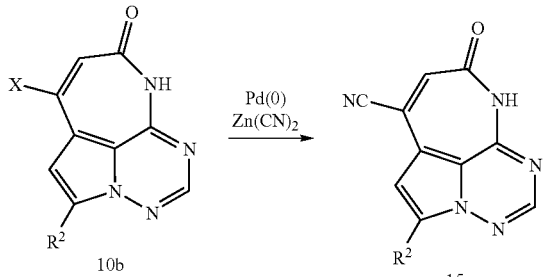
Synthesis of a compound of formula 1; where $X^1 = O$, $Y^1 = CN$, $Z^1 = H$, $R^1 = H$ (15a)
Scheme 16
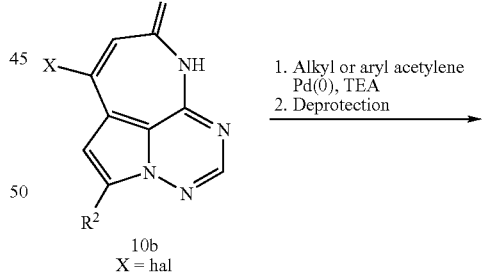
Synthesis of a compound of formula 1; where $X^1 = O$, $Y^1 = C \equiv CR$, $Z^1 = H$, $R = $ alkyl or aryl, $R^1 = H$ (16a)

Scheme 17
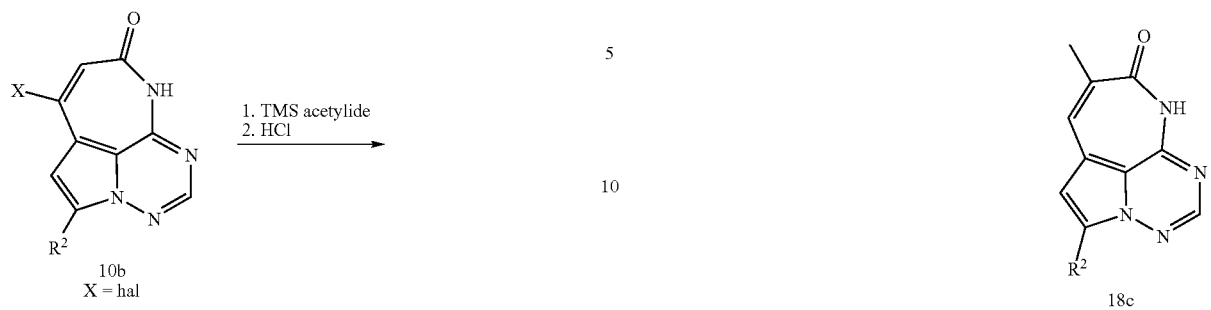
Synthesis of a compound of formula 1; where $X^1 = O$, $Y^1 = C \equiv CH$, $Z^1 = H$, $R^1 = H$, (17a)
Scheme 18
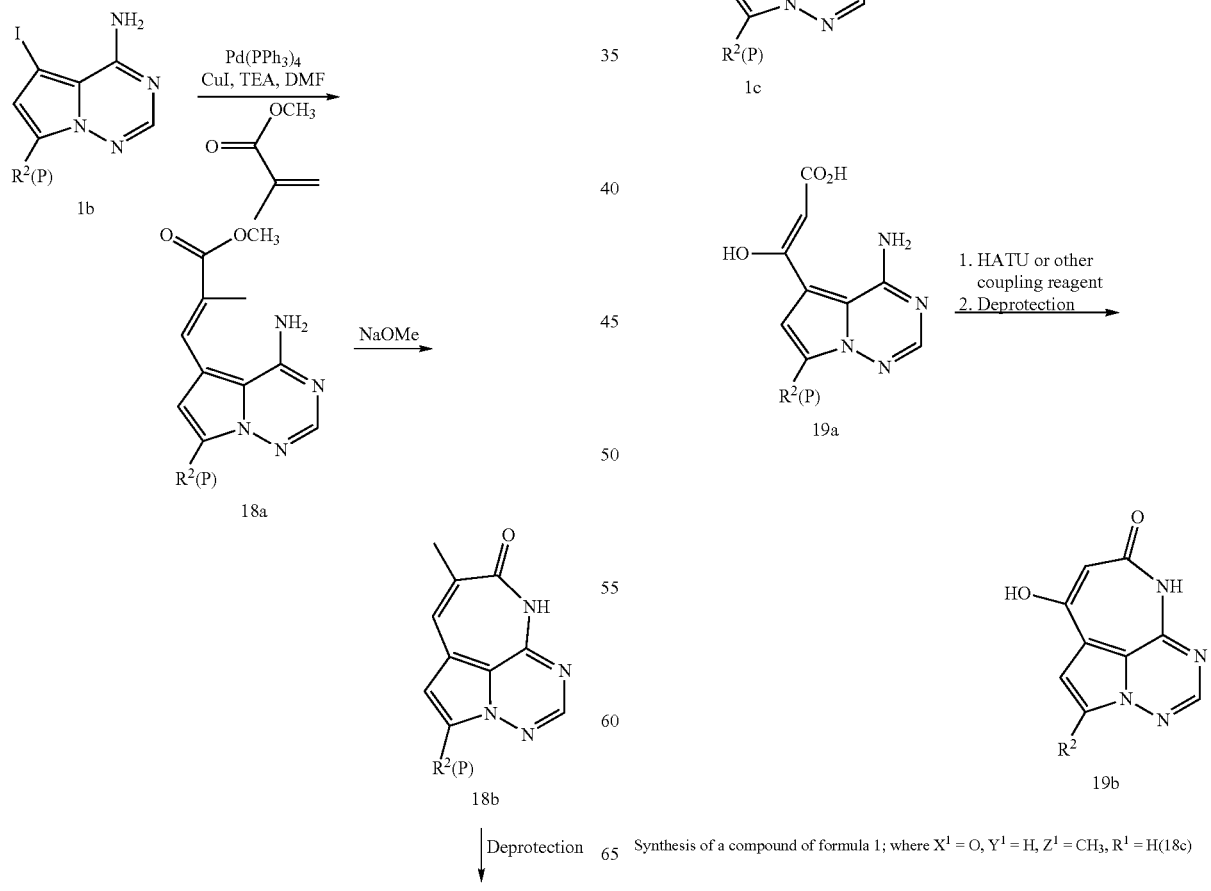
Synthesis of a compound of formula 1; where $X^1 = O$, $Y^1 = H$, $Z^1 = CH_3$, $R^1 = H$ (18c)
Scheme 19
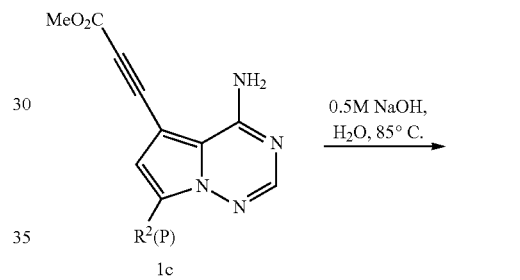
Synthesis of a compound of formula 1; where $X^1 = O$, $Y^1 = H$, $Z^1 = CH_3$, $R^1 = H$(18c)

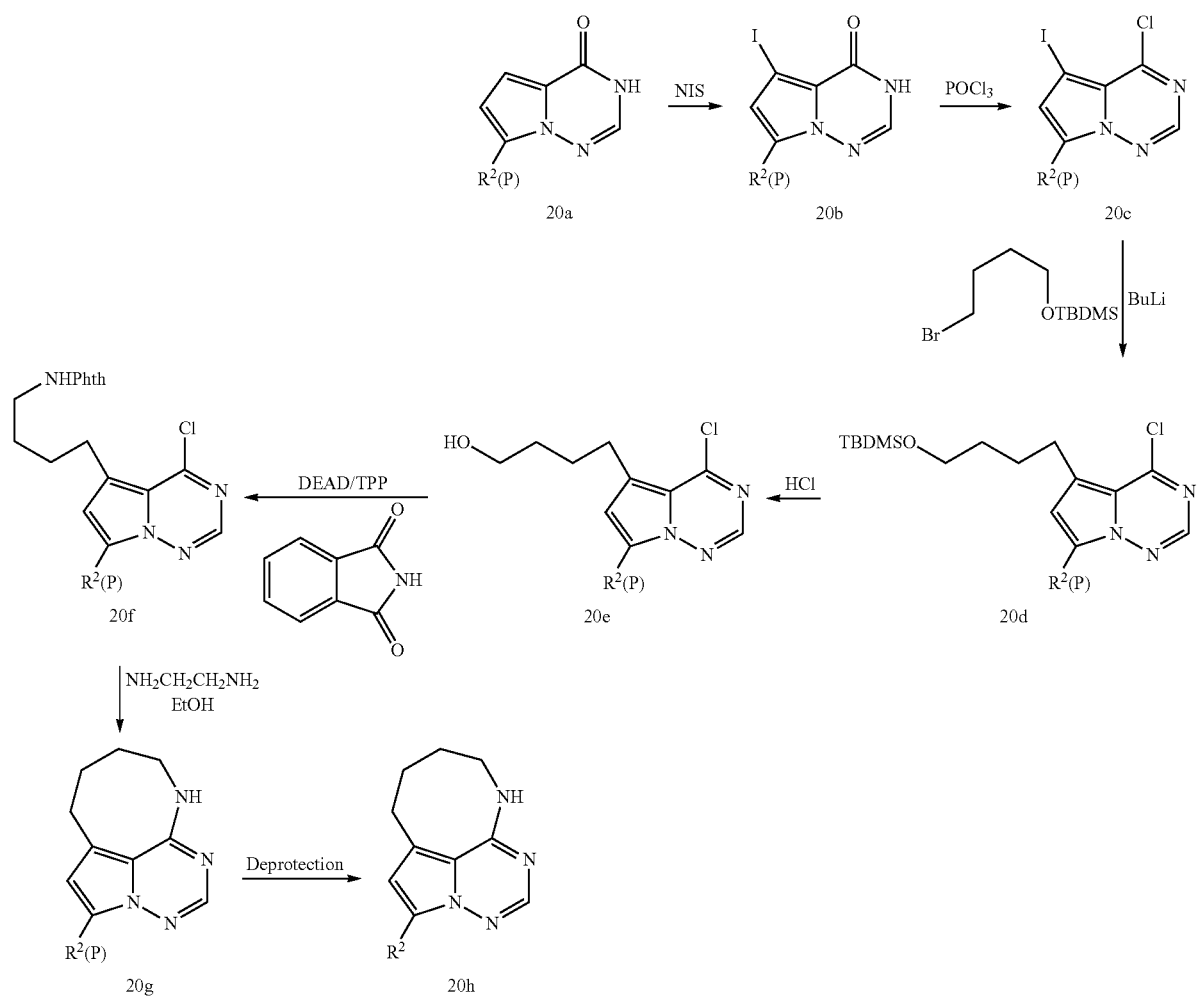
Scheme 20
Synthesis of a compound of formula 2; where $X^2$ = two hydrogens, $Y^2 = Z^2 = H$, t = 2, $R^1 = H$ (20h)
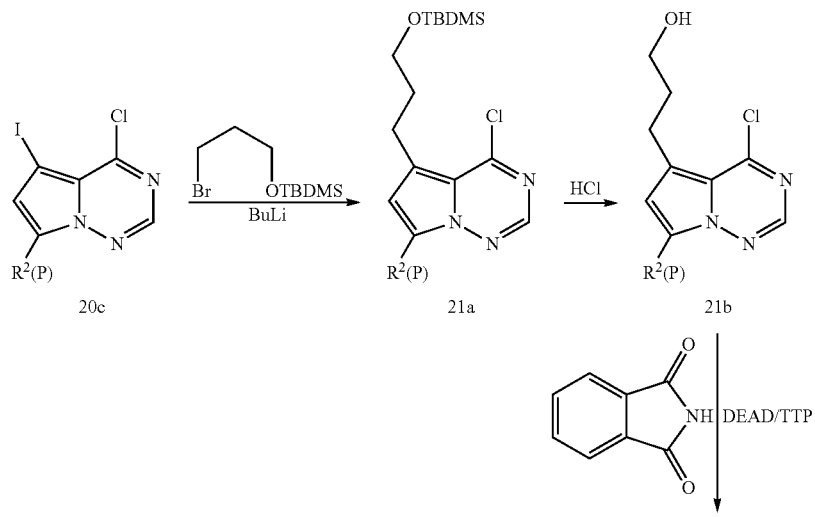
Scheme 21

Scheme 22
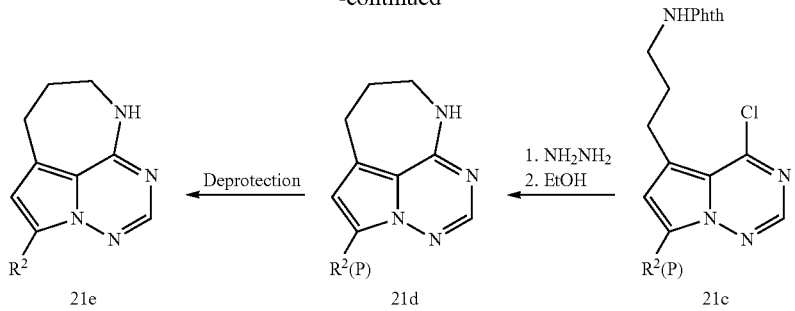
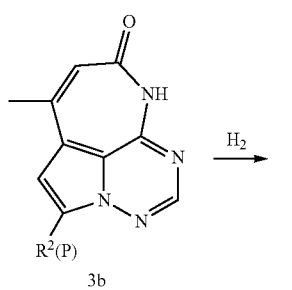
Synthesis of a compound of formula 2; where $X^2 = O$, $Y^2 = H$, $Z^2 = CH_3$, $t = 1$, $R^1 = H$ (23b)
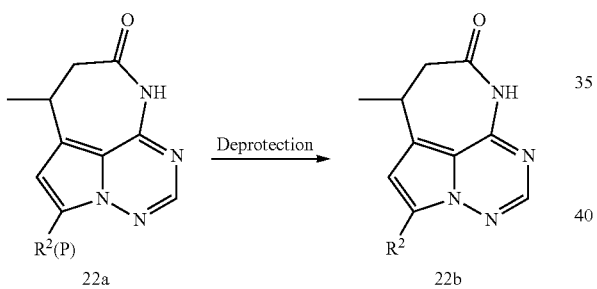
Synthesis of a compound of formula 2; where $X^2 = O$, $Y^2 = CH_3$, $Z^2 = H$, $t = 1$, $R^1 = H$ (22b)
Scheme 24
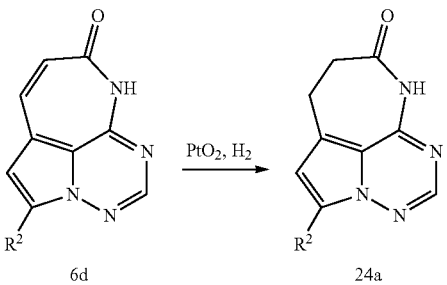
Synthesis of a compound of formula 2; where $X^2 = O$, $Y^2 = Z^2 = H$, $t = 1$, $R^1 = H$ (24a)
Scheme 25
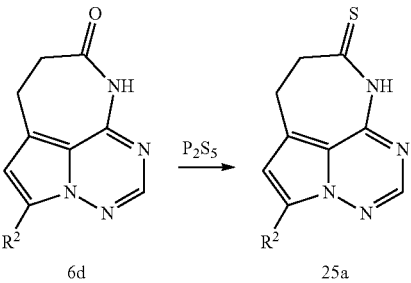
Synthesis of a compound of formula 2; where $X^2 = S$, $Y^2 = Z^2 = H$, $t = 1$, $R^1 = H$ (25a)
Scheme 23
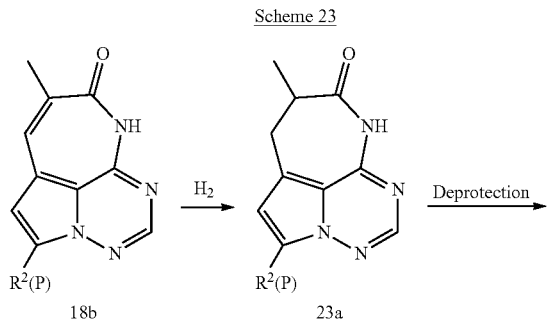

Scheme 26
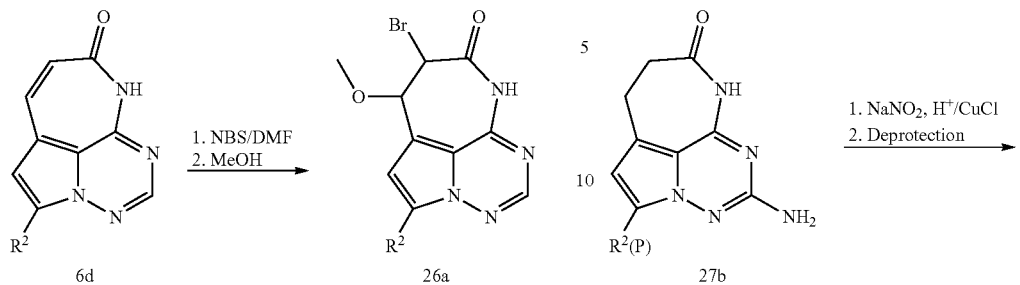
Synthesis of a compound of formula 2;
where $X^2 = O$, $Y^2 = OCH_3$, $Z^2 = Br$, $t = 1$, $R^1 = H$ (26a)
Scheme 27
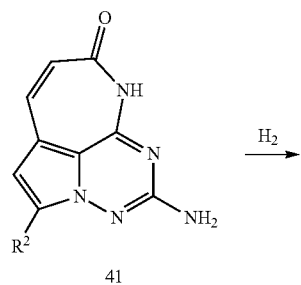
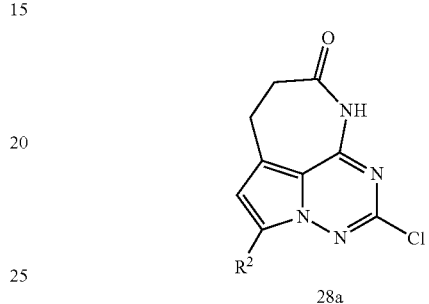
Synthesis of a compound of formula 2;
where $X^2 = O$, $Y^2 = Z^2 = H$, $t = 1$, $R^1 = F$ (27c)
Scheme 28
Synthesis of a compound of formula 2;
where $X^2 = O$, $Y^2 = Z^2 = H$, $t = 1$, $R^1 = Cl$ (28a)
Scheme 29
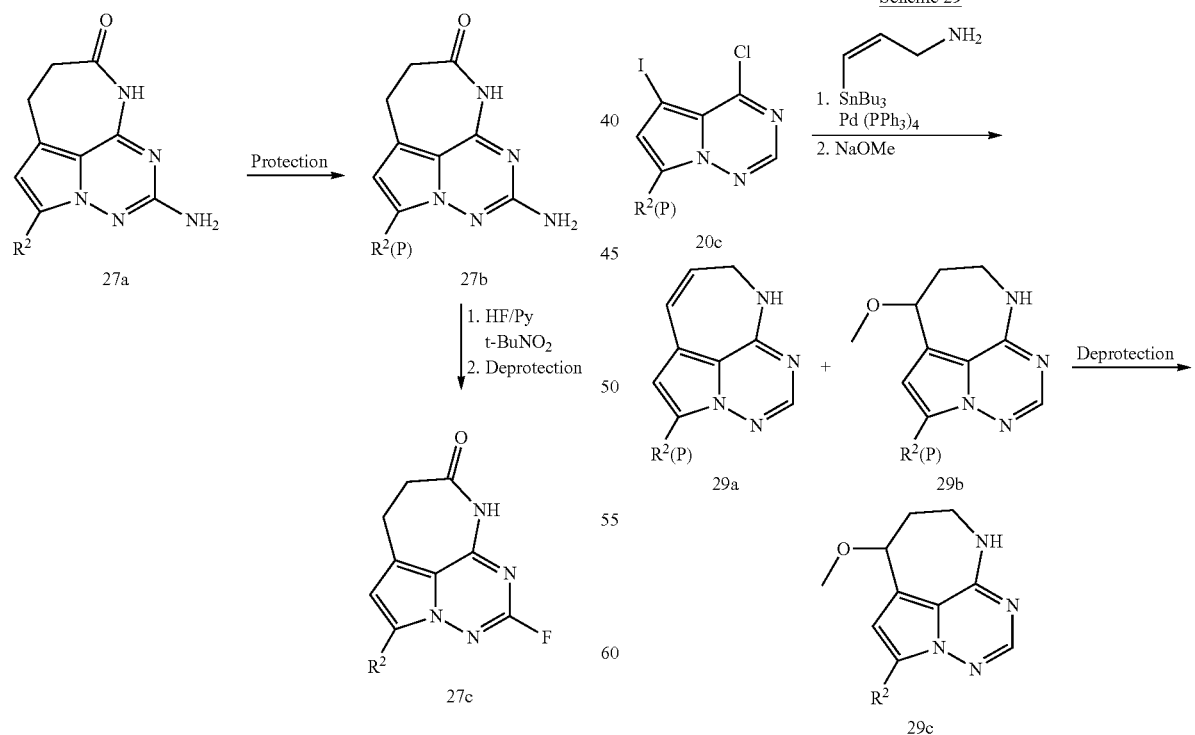
Synthesis of a compound of formula 2;
where $X^2 =$ two hydrogens, $Y^2 = OCH_3$, $Z^2 = H$, $t = 1$, $R^1 = H$ (29c)

Scheme 30
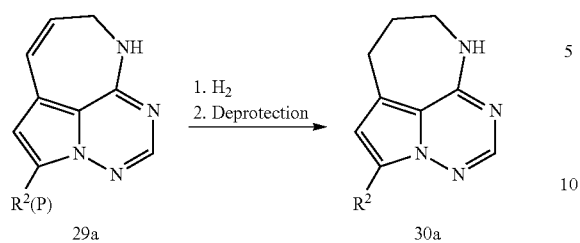
Synthesis of a compound of formula 2;
where $X^2$ = two hydrogens, $Y^2 = Z^2$ = H, t = 1, $R^1$ = H (30a)
Scheme 31
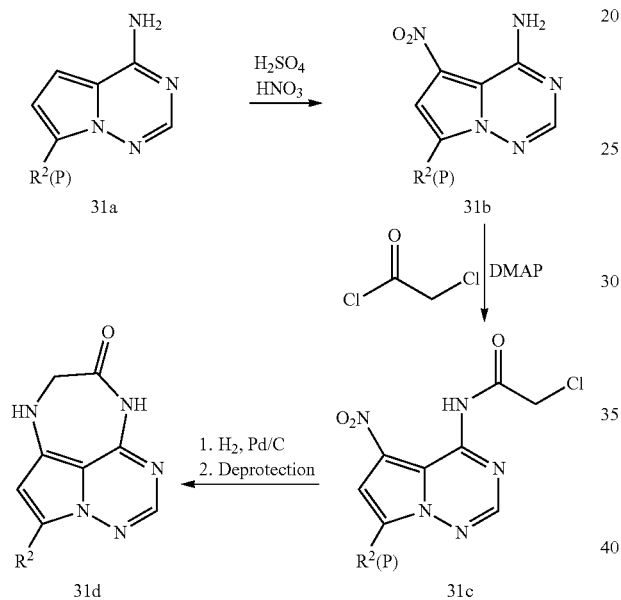
Synthesis of a compound of formula 4;
where $X^4$ = O, $Y^4$ = two hydrogens, $R^1$ = H (31d)
Scheme 32
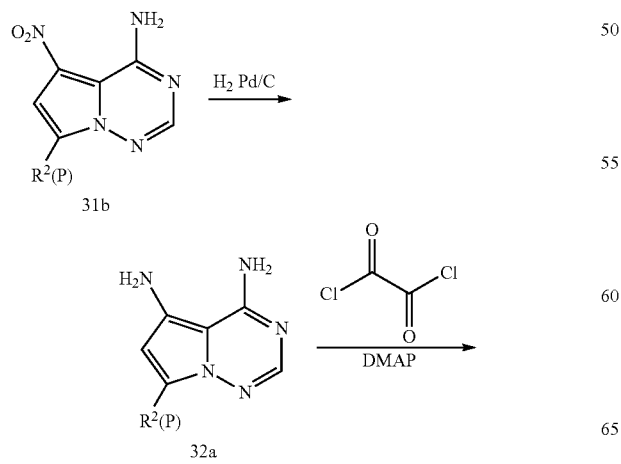
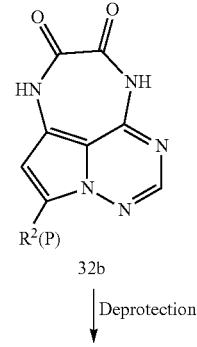
Deprotection
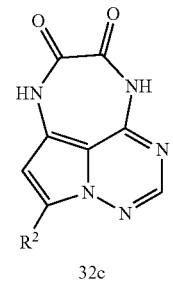
Synthesis of a compound of formula 4;
where $X^4 = Y^4$ = O, $R^1$ = H (32c)
Scheme 33
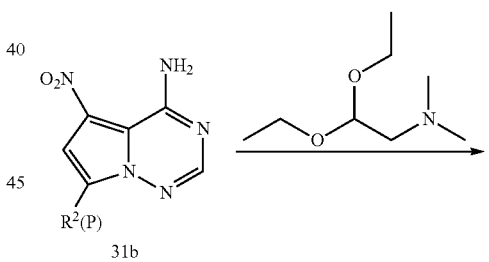
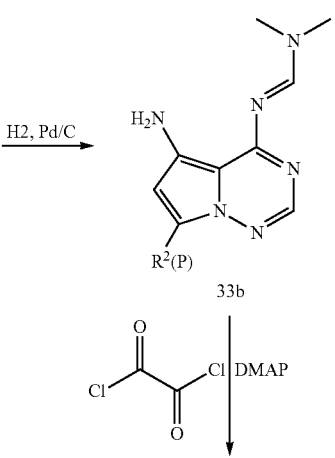

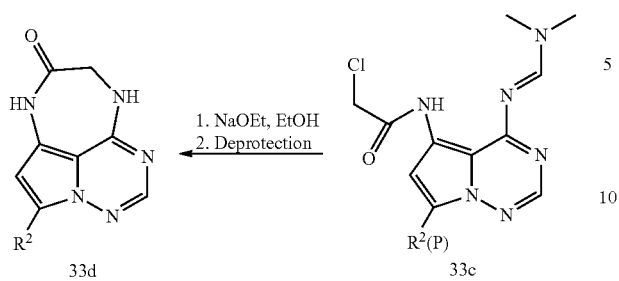
33d      33c
Synthesis of a compound of formula 4;
where $X^4$ = two hydrogens, $Y^4$ = O, $R^1$ = H (33d)
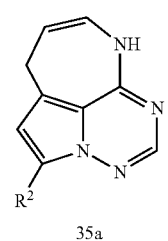
35a
Synthesis of a compound of formula 6; where $R^1$ = H (35a)
Scheme 34
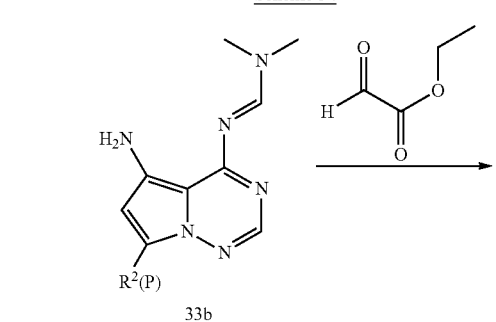
33b
Scheme 36
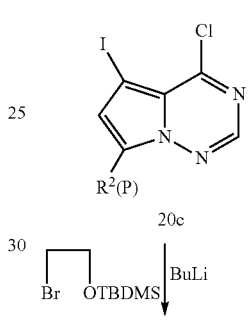
20c
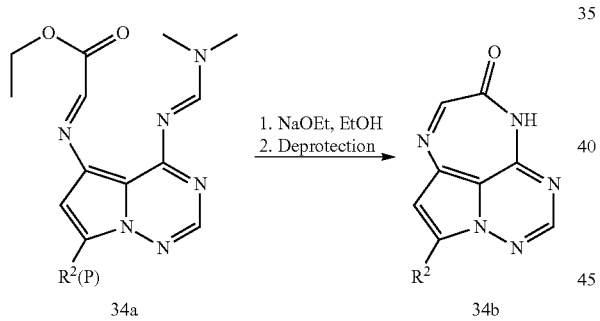
34a      34b
Synthesis of a compound of formula 5; where $X^5$ = O, $R^1$ = H (34b)
Scheme 35
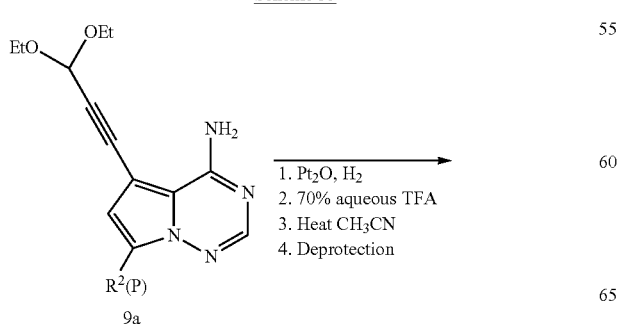
9a
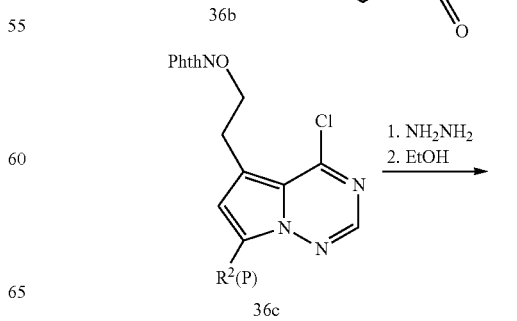
36c

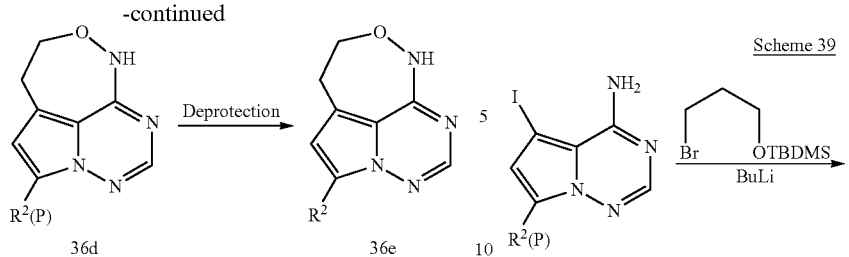
Scheme 39
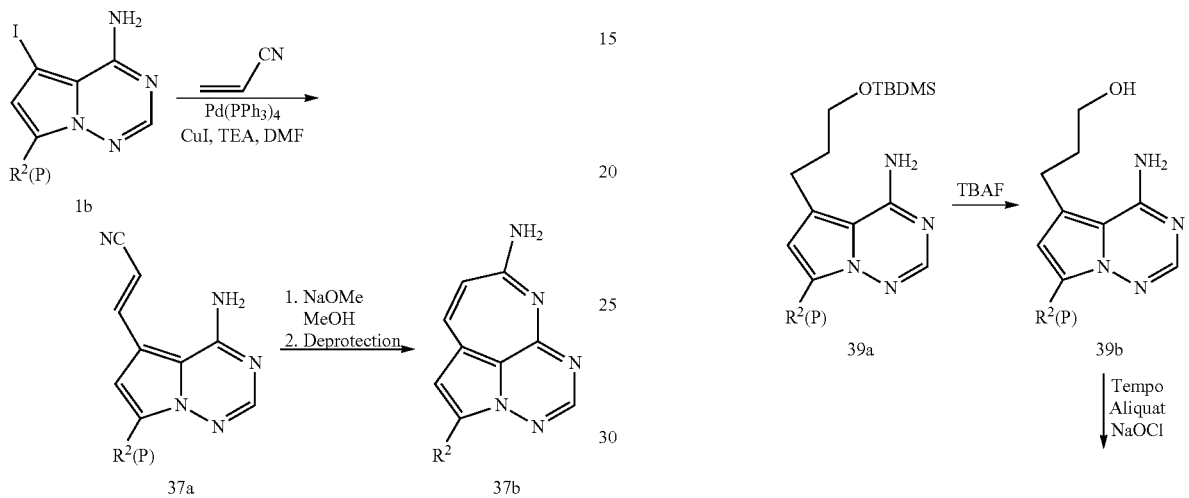
Scheme 37
Synthesis of a compound of formula 8; where $X^8 = NH_2$, $R^1 = H$ (37b)
Scheme 38
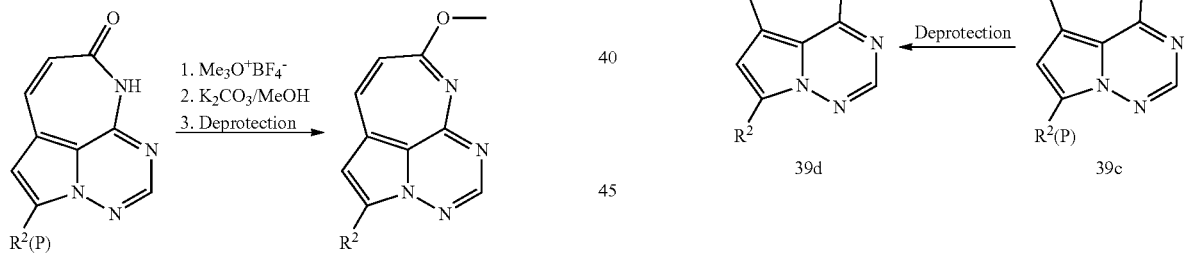
Synthesis of a compound of formula 8; where $X^8 = OCH_3$, $R^1 = H$ (38a)
Synthesis of a compound of formula 9; where $R^1 = H$ (39d)
Scheme 40 for the Synthesis of Example 1
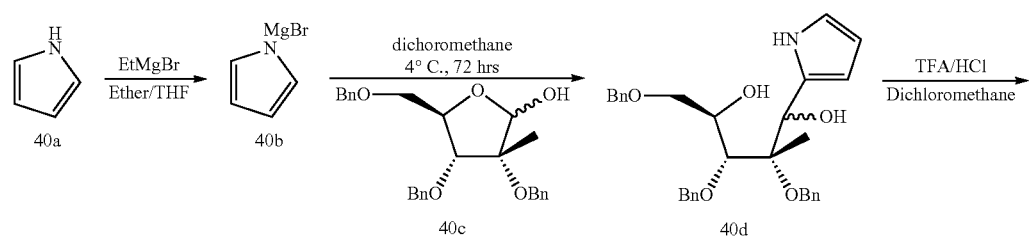

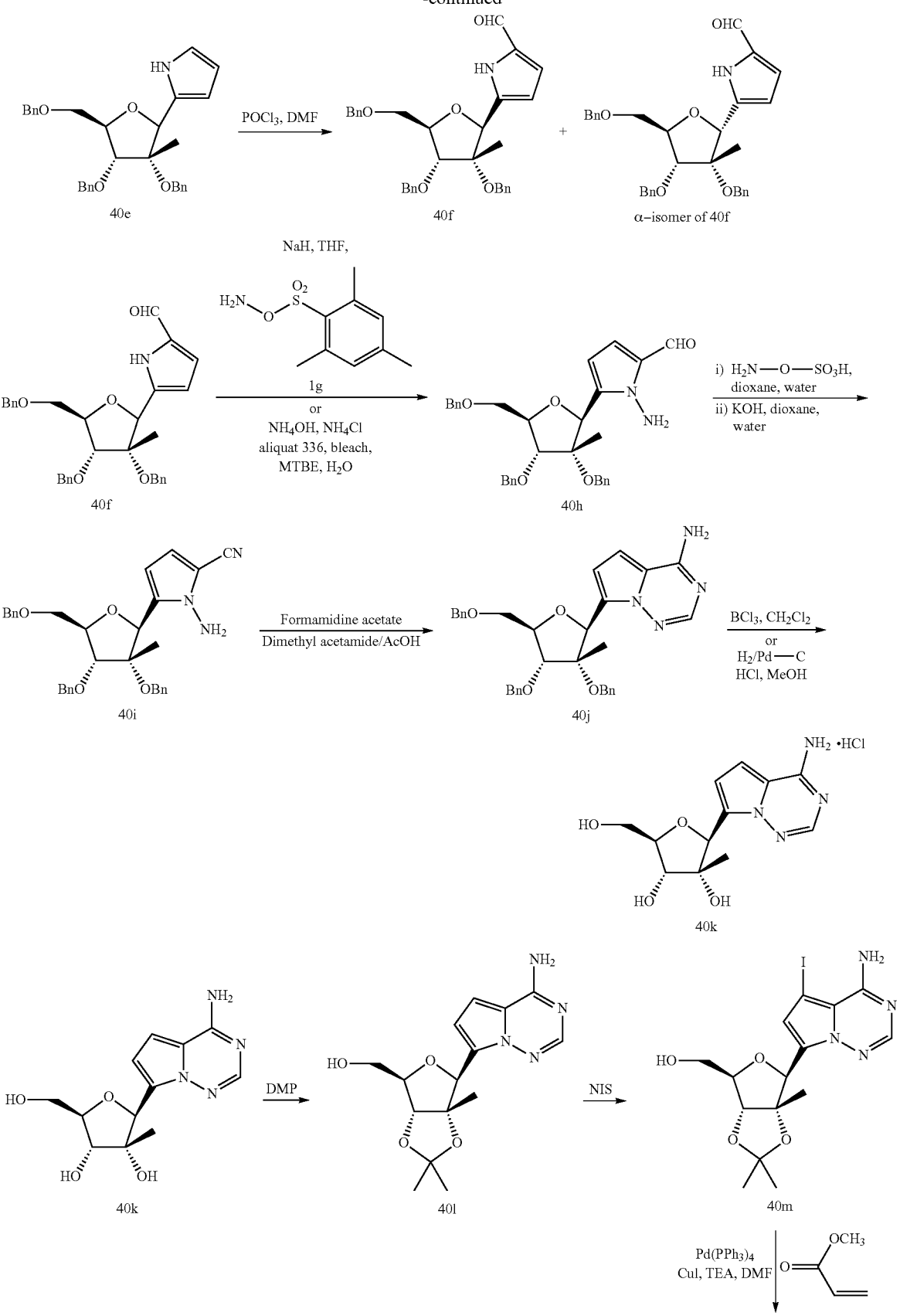

-continued
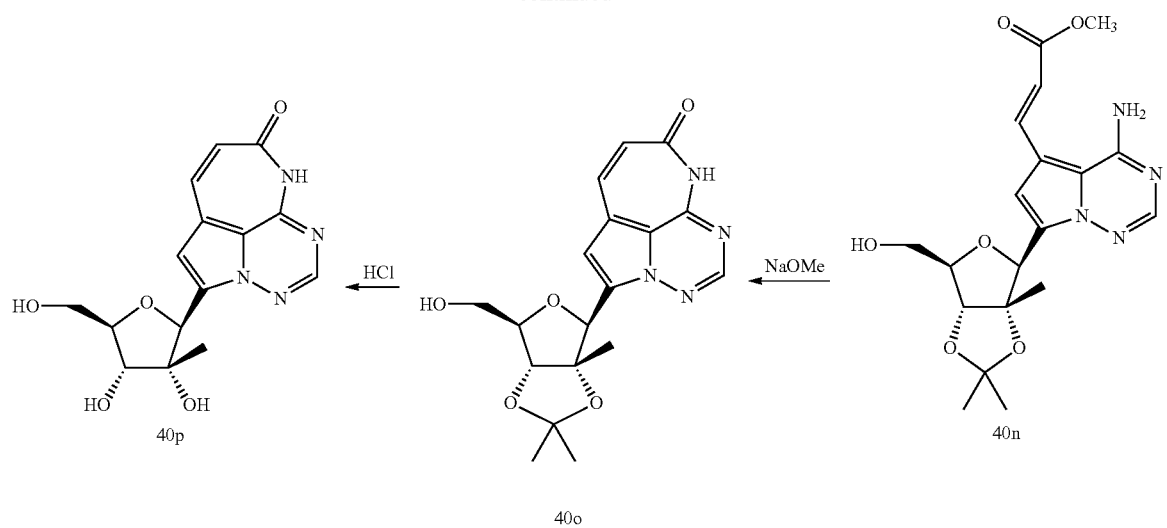
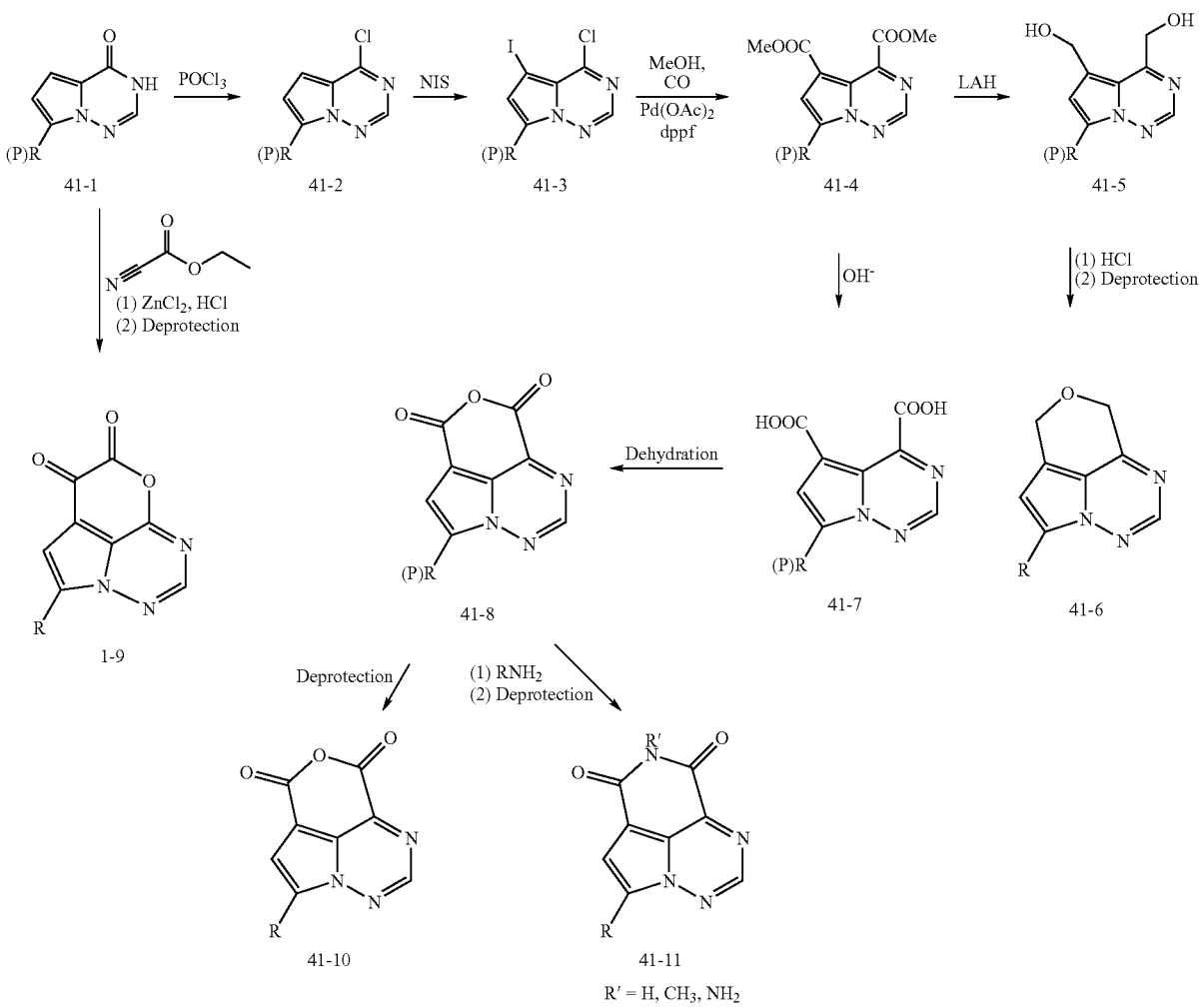
Scheme 41.
R' = H, CH$_3$, NH$_2$

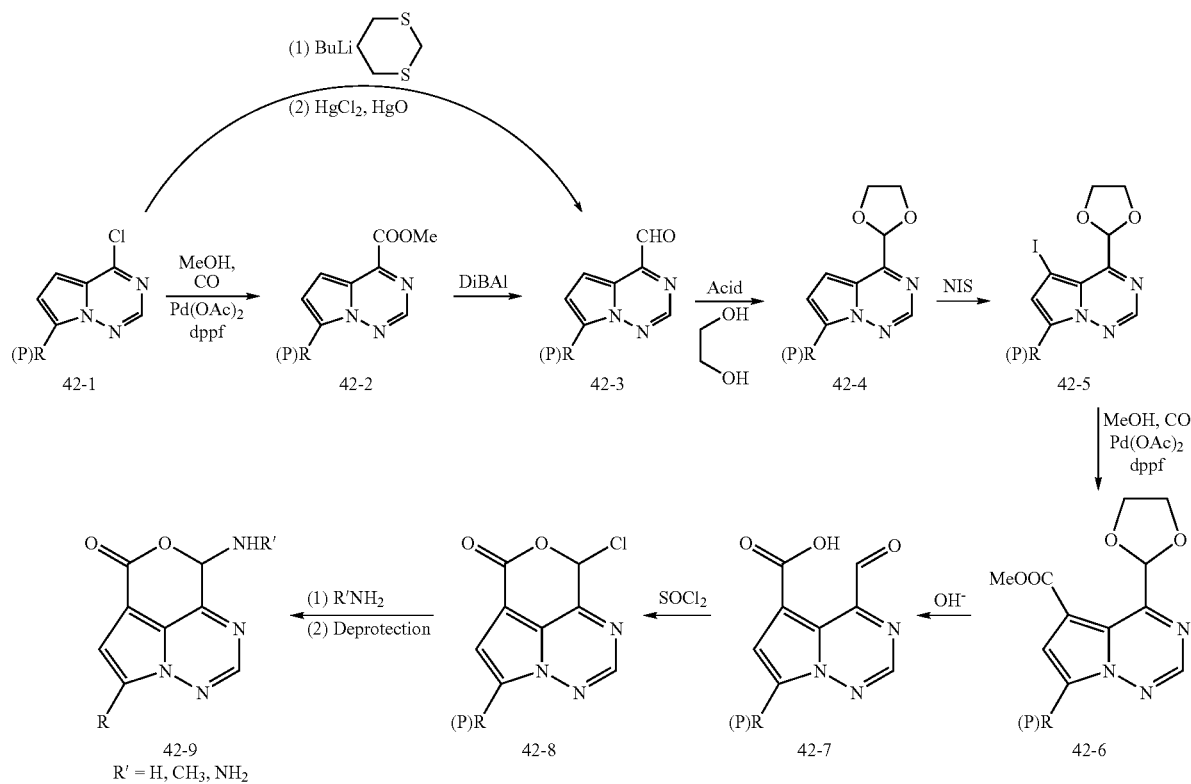
Scheme 42.

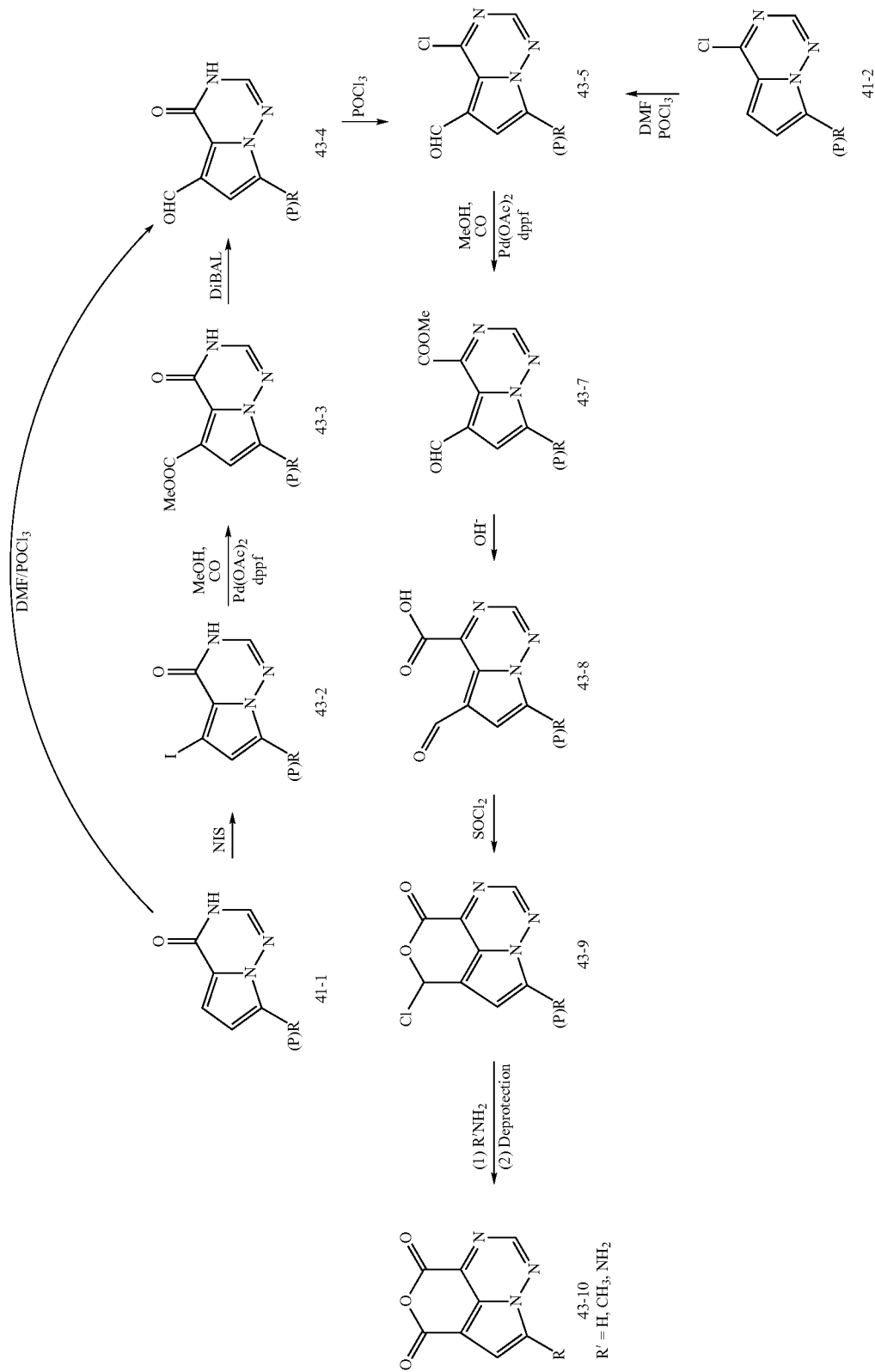

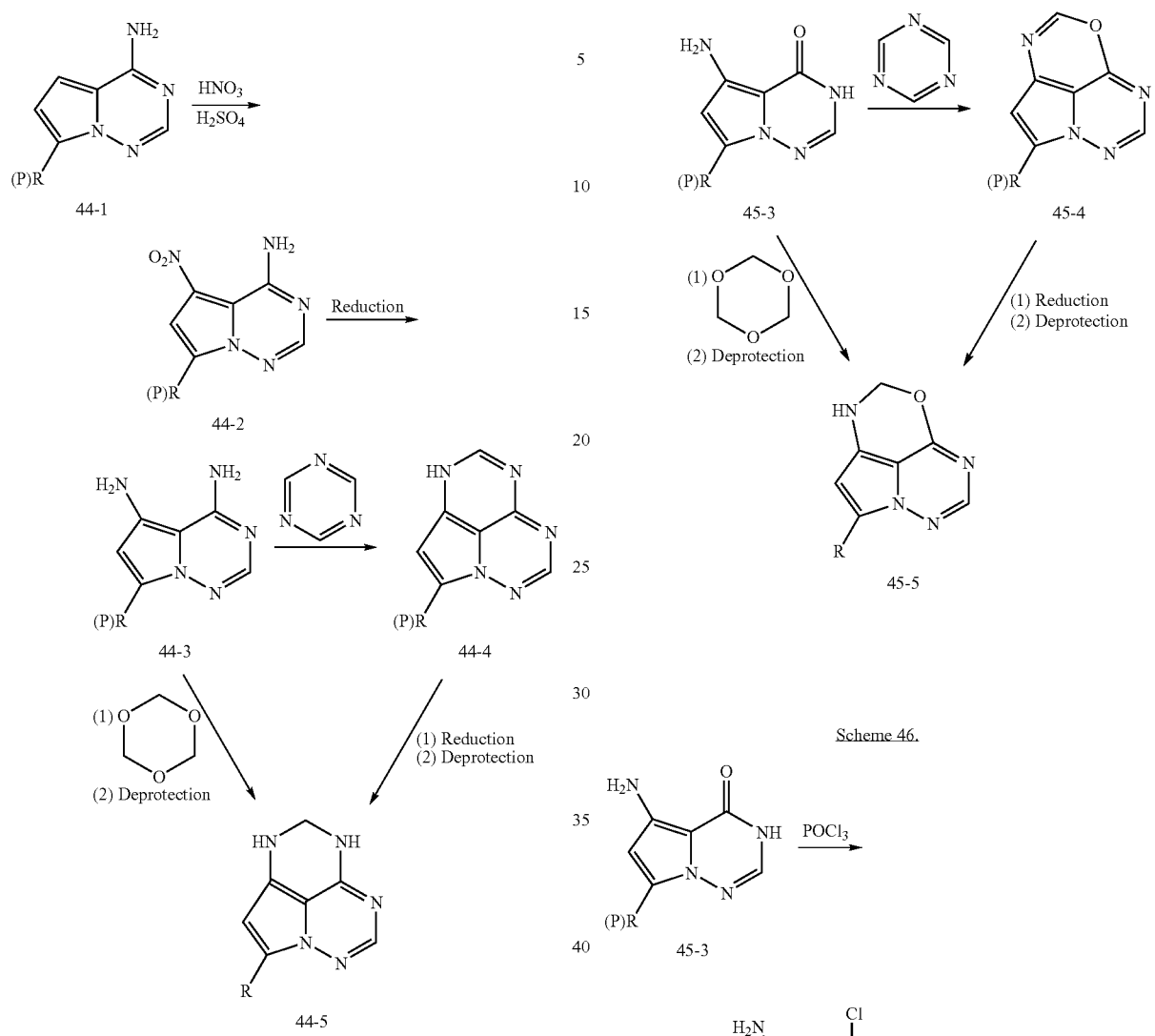
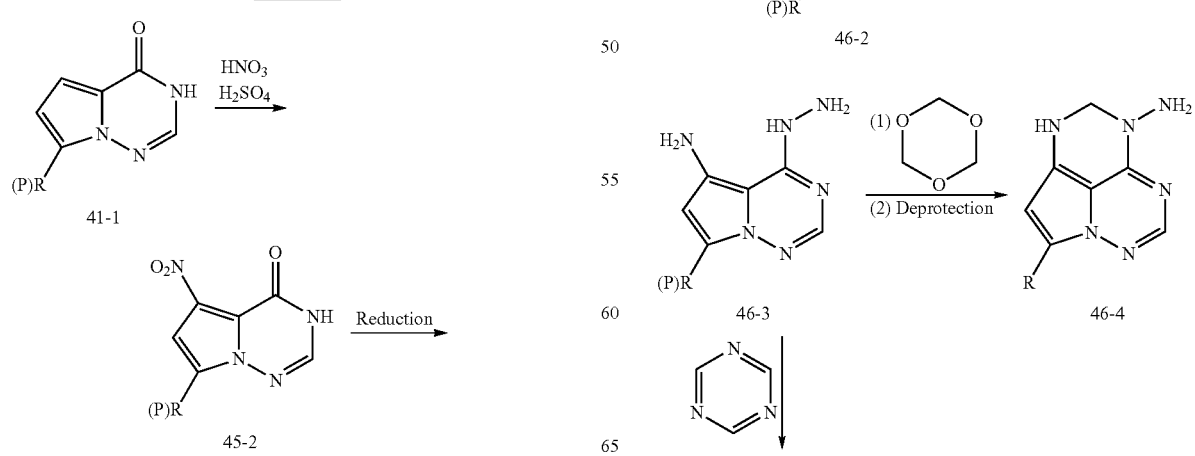

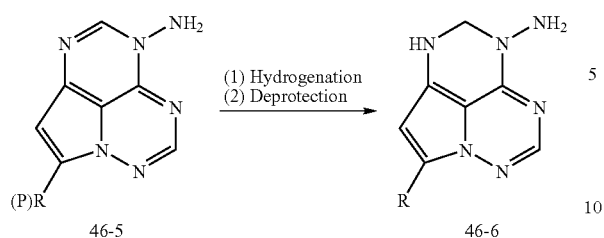
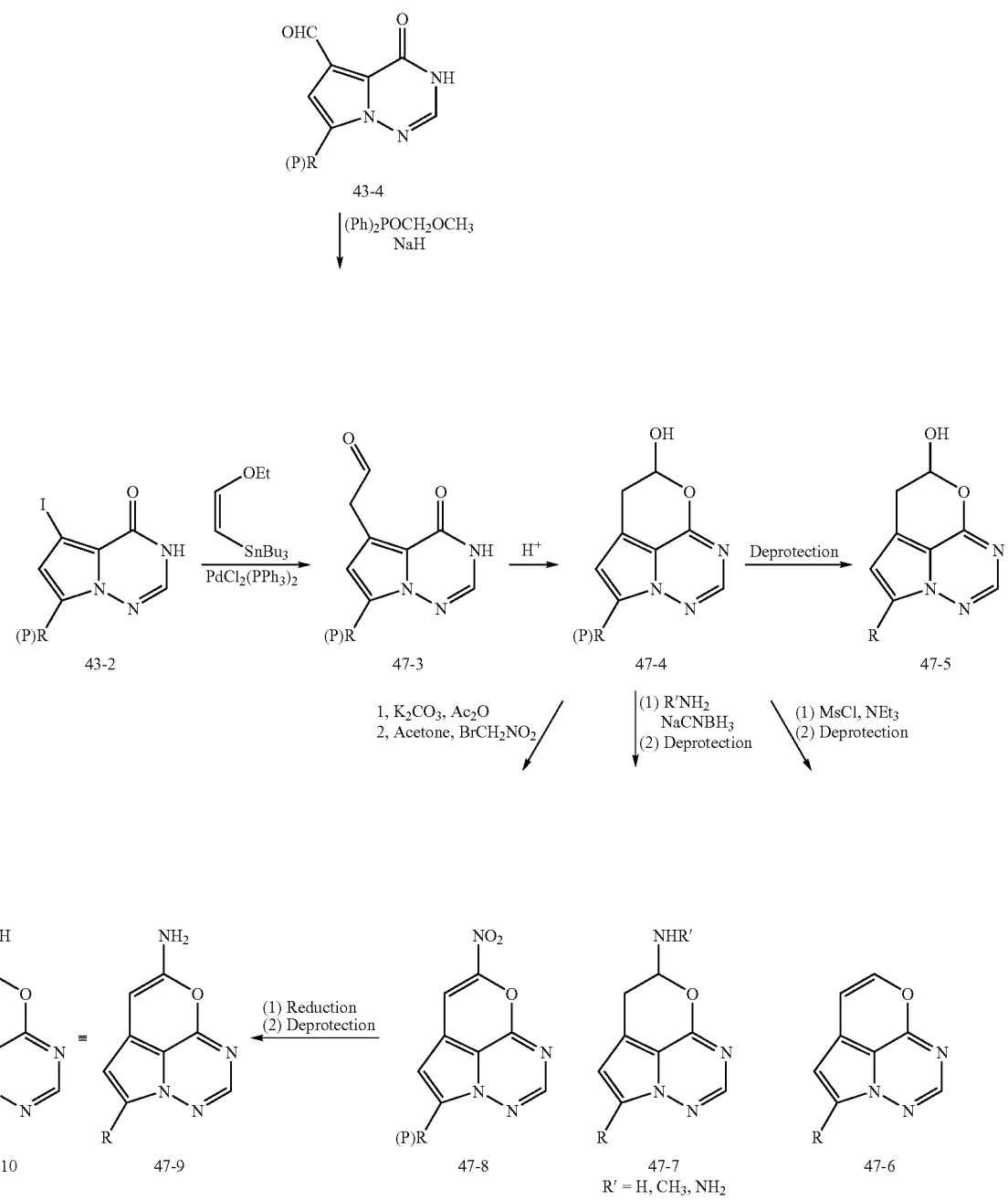
Scheme 47.

Scheme 48.
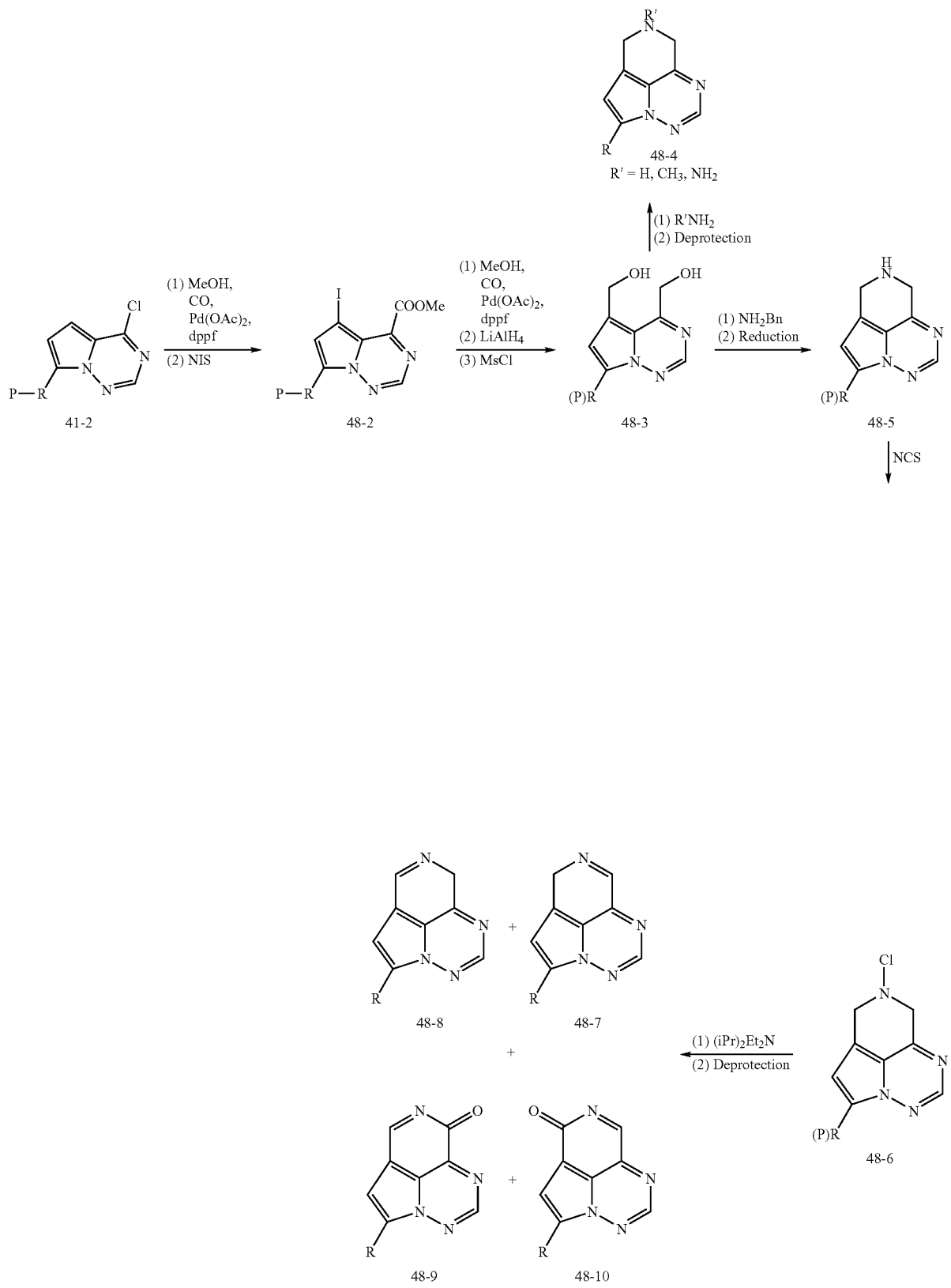

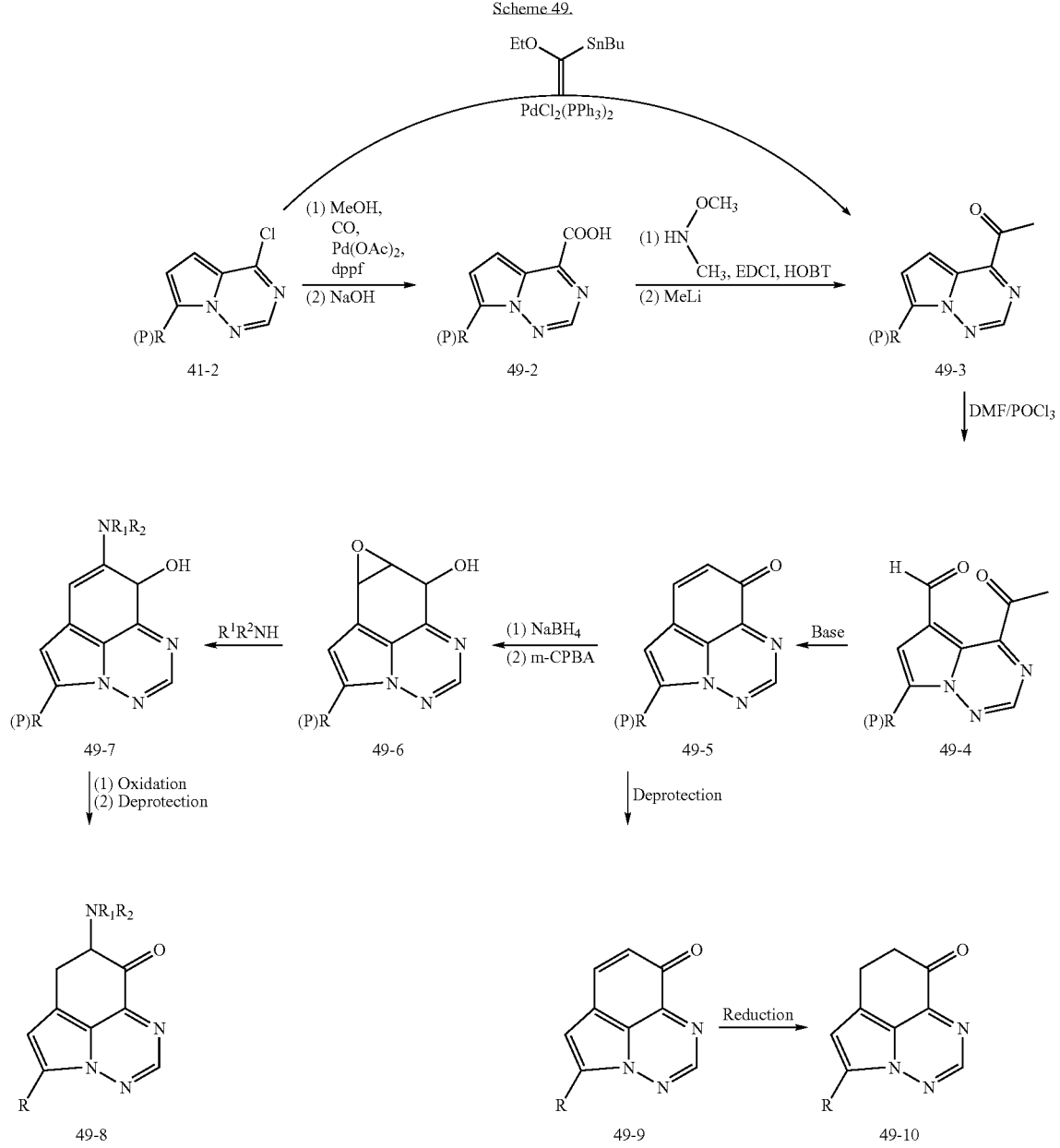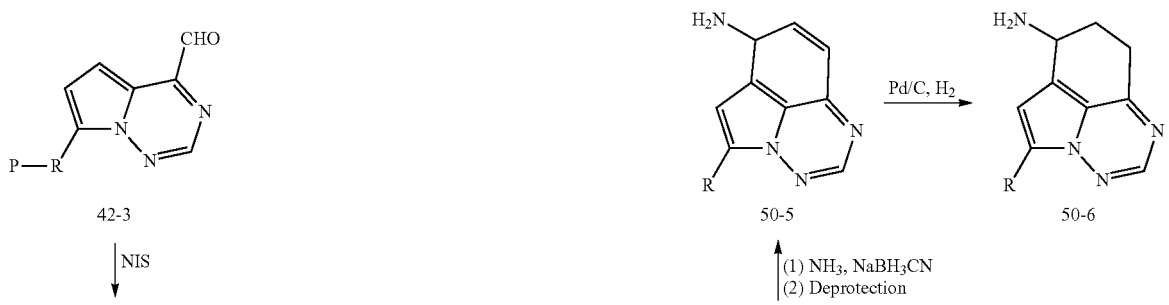

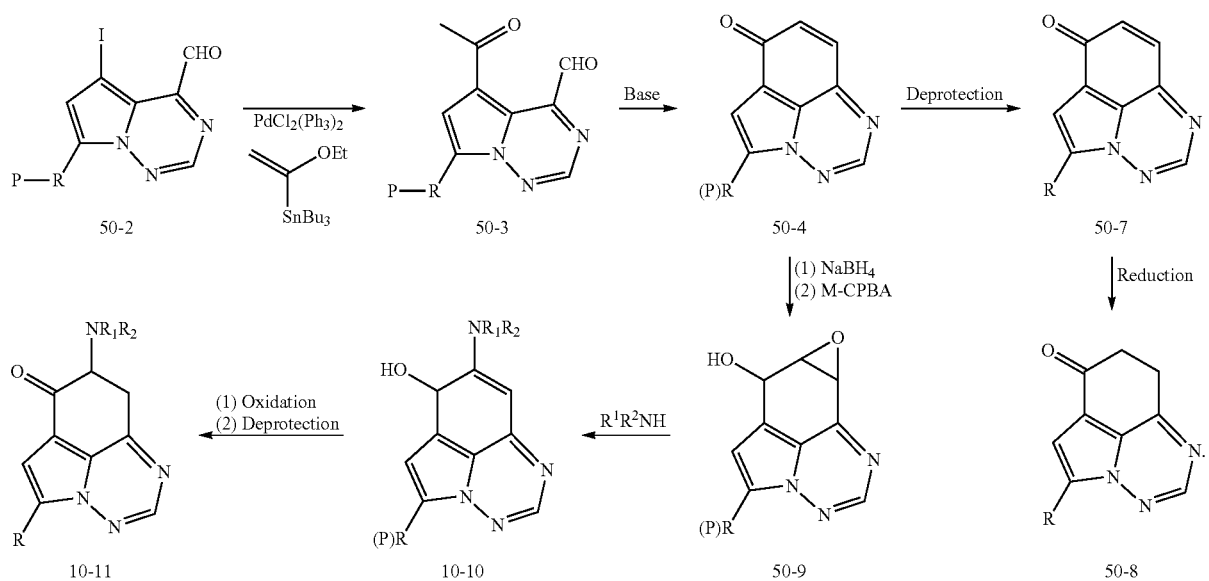
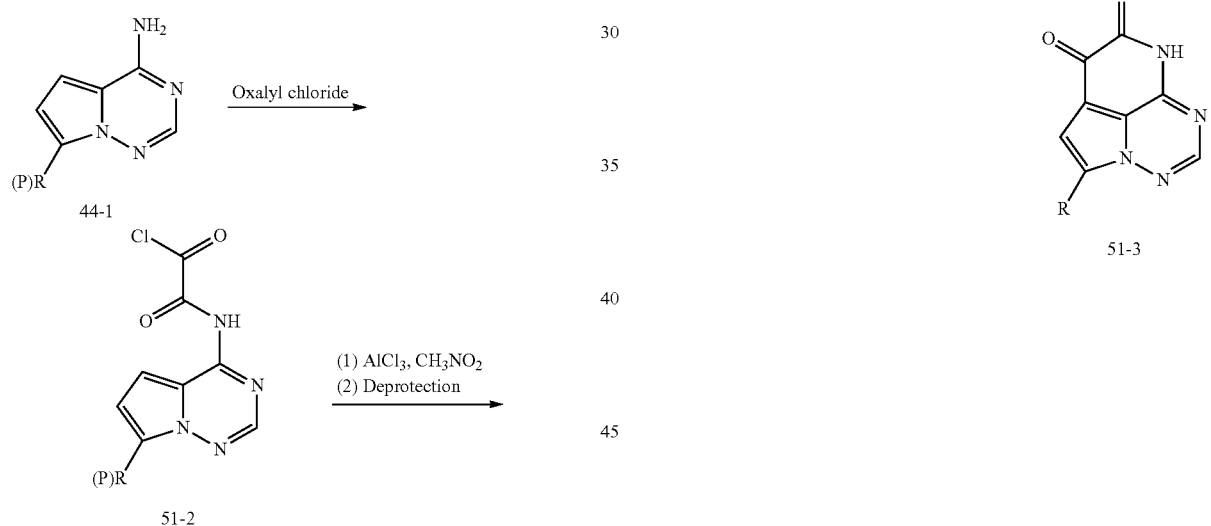
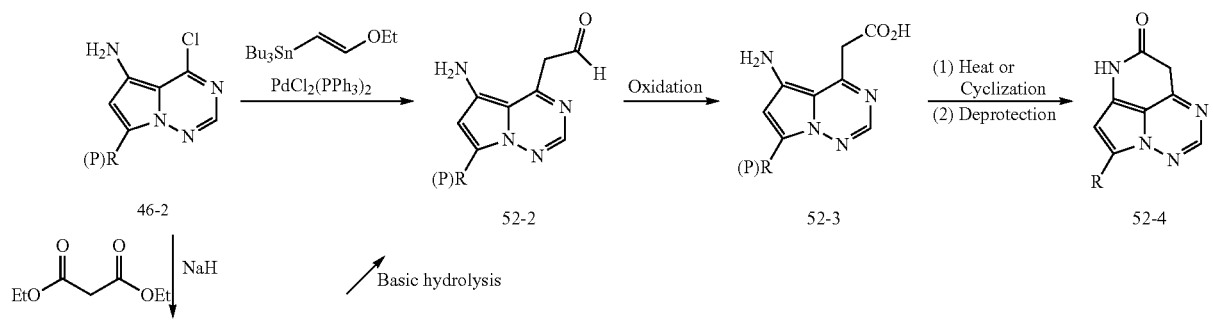

-continued
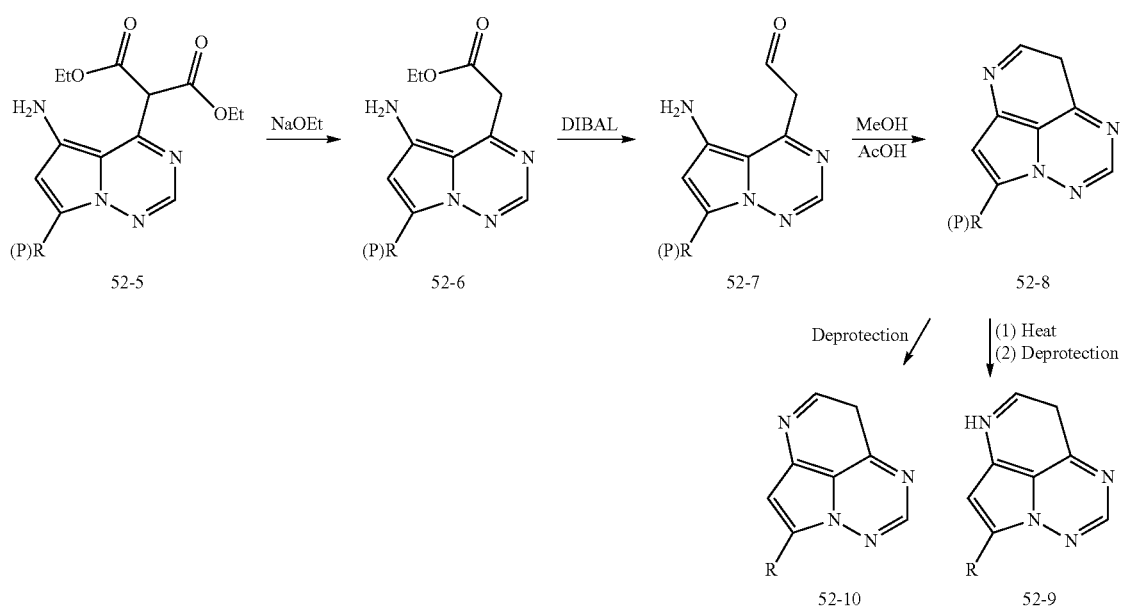
Scheme 53.
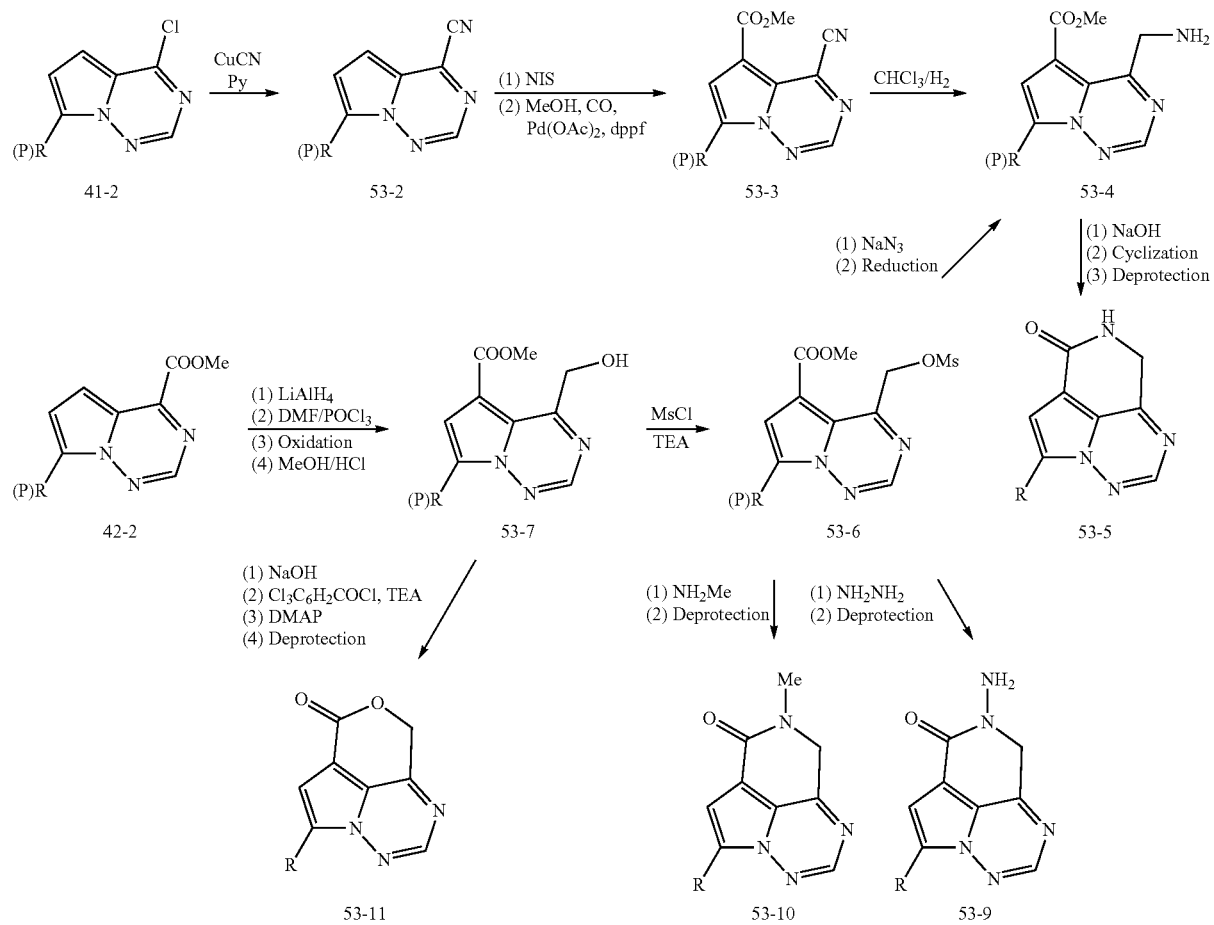

Scheme 54.
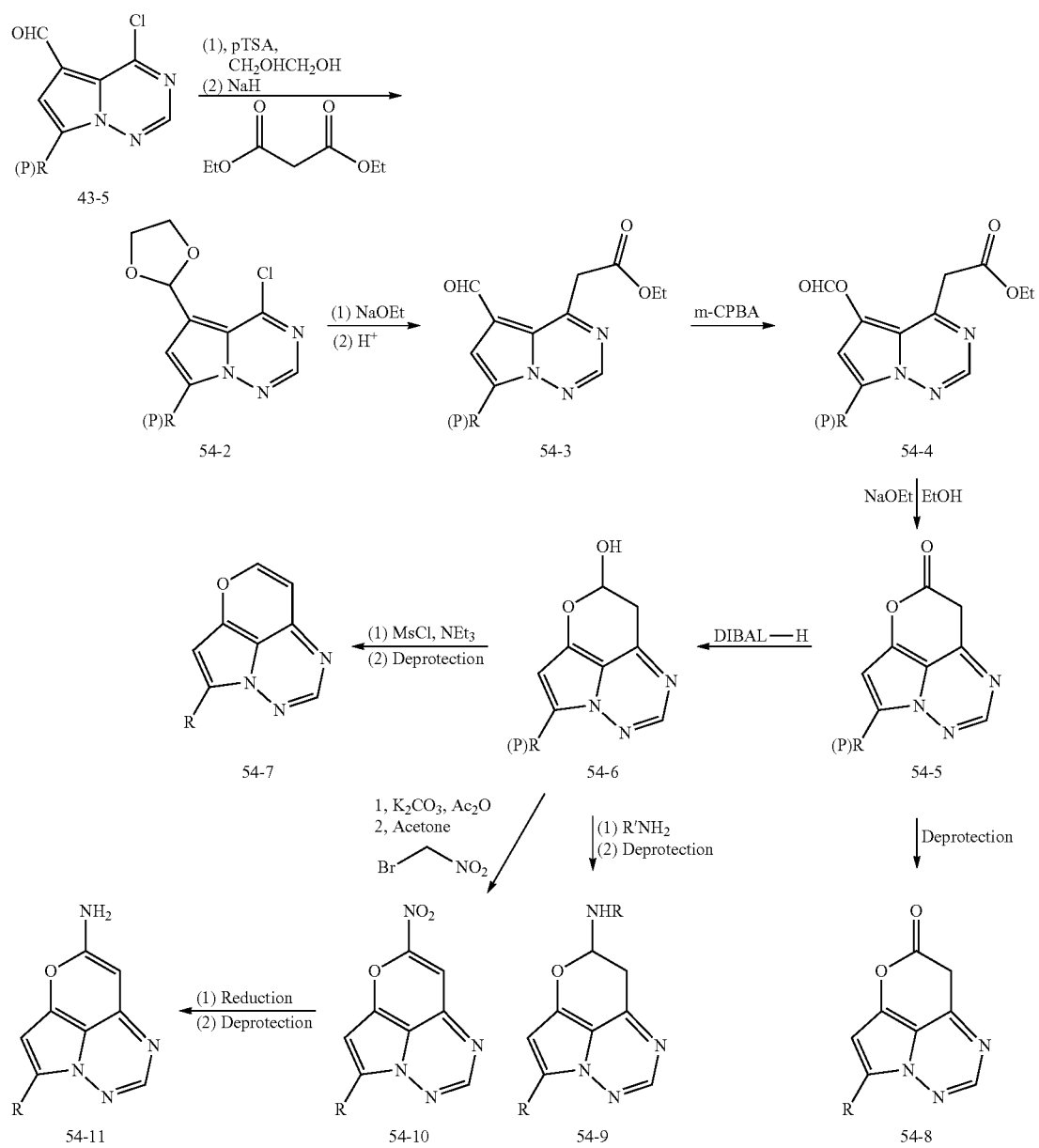
Scheme 55.
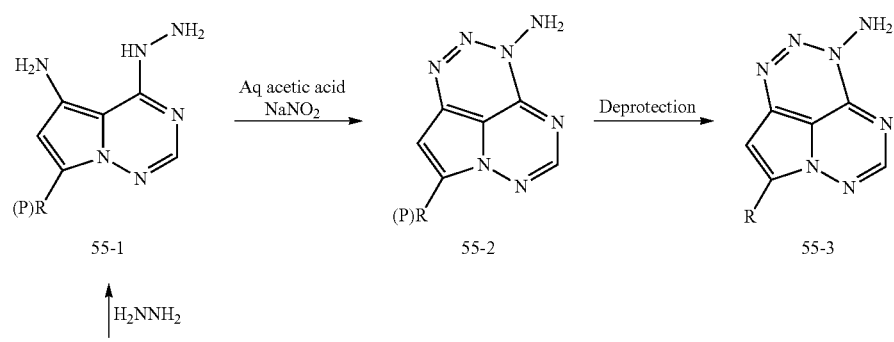

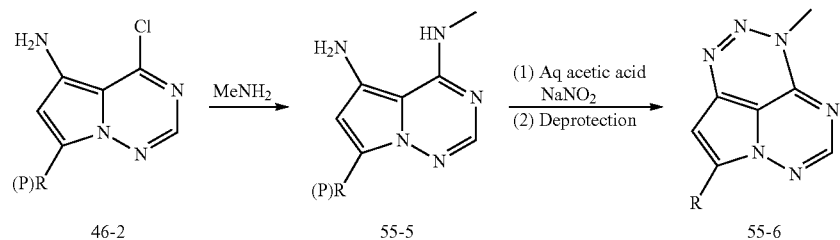
46-2, 55-5, 55-6
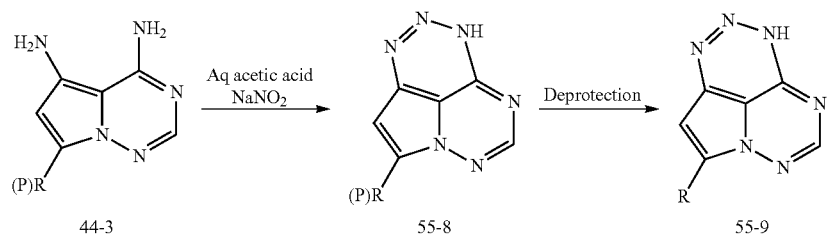
44-3, 55-8, 55-9
Scheme 56.
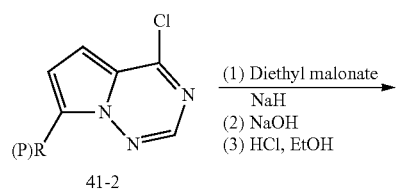
41-2
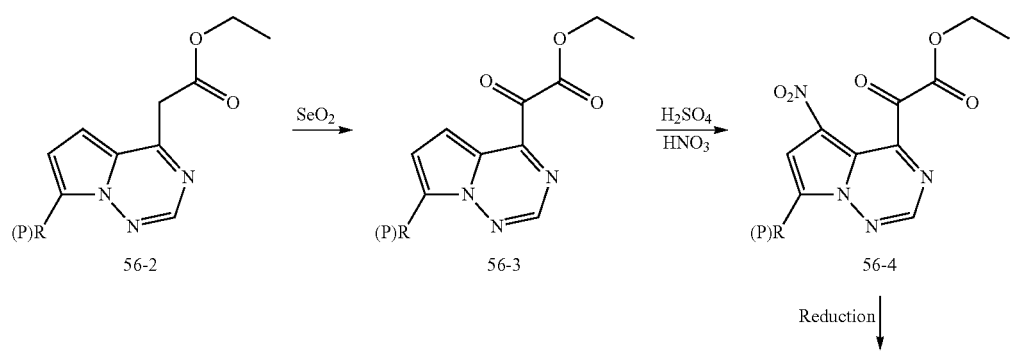
56-2, 56-3, 56-4
Reduction
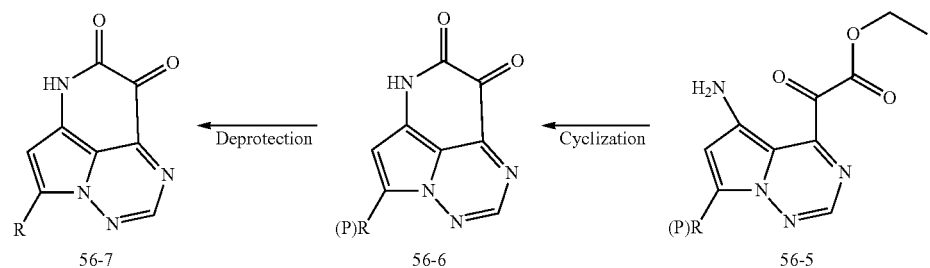
56-7, 56-6, 56-5

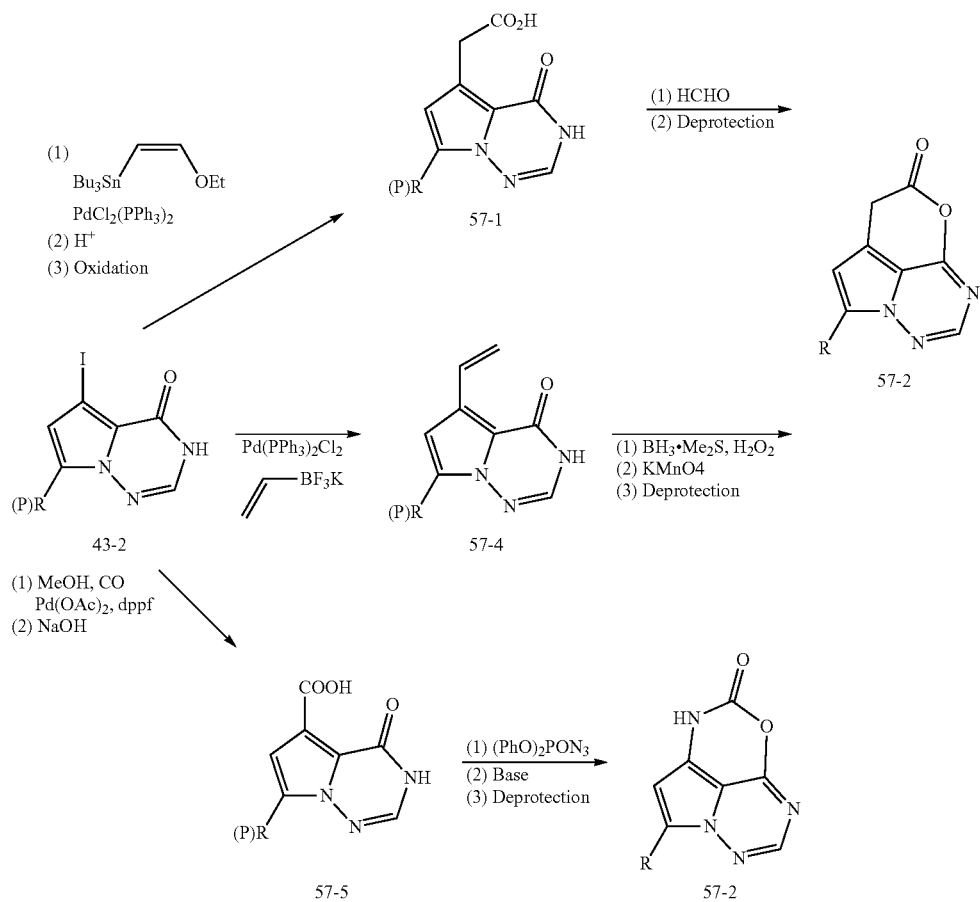
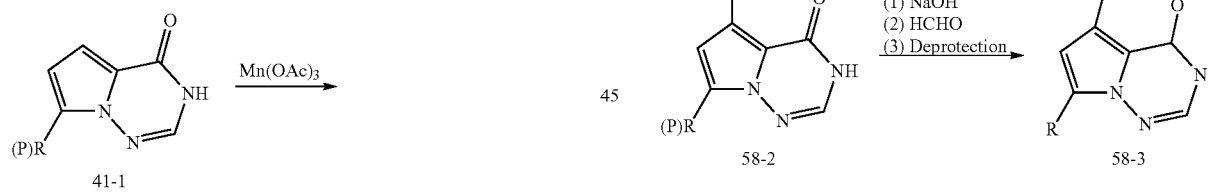
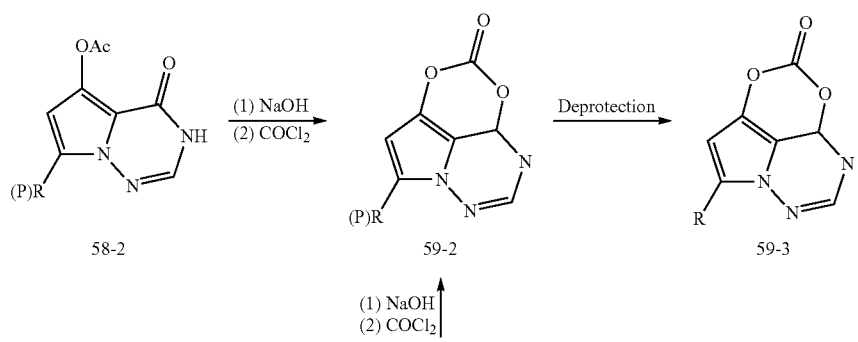

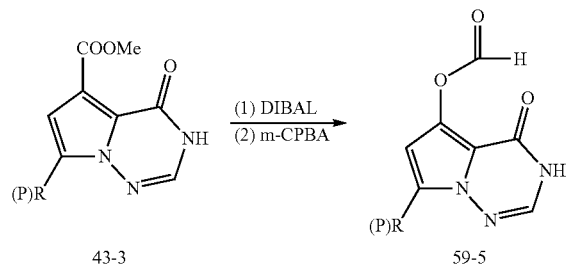
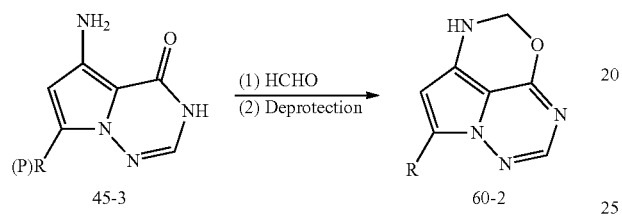
Scheme 61.
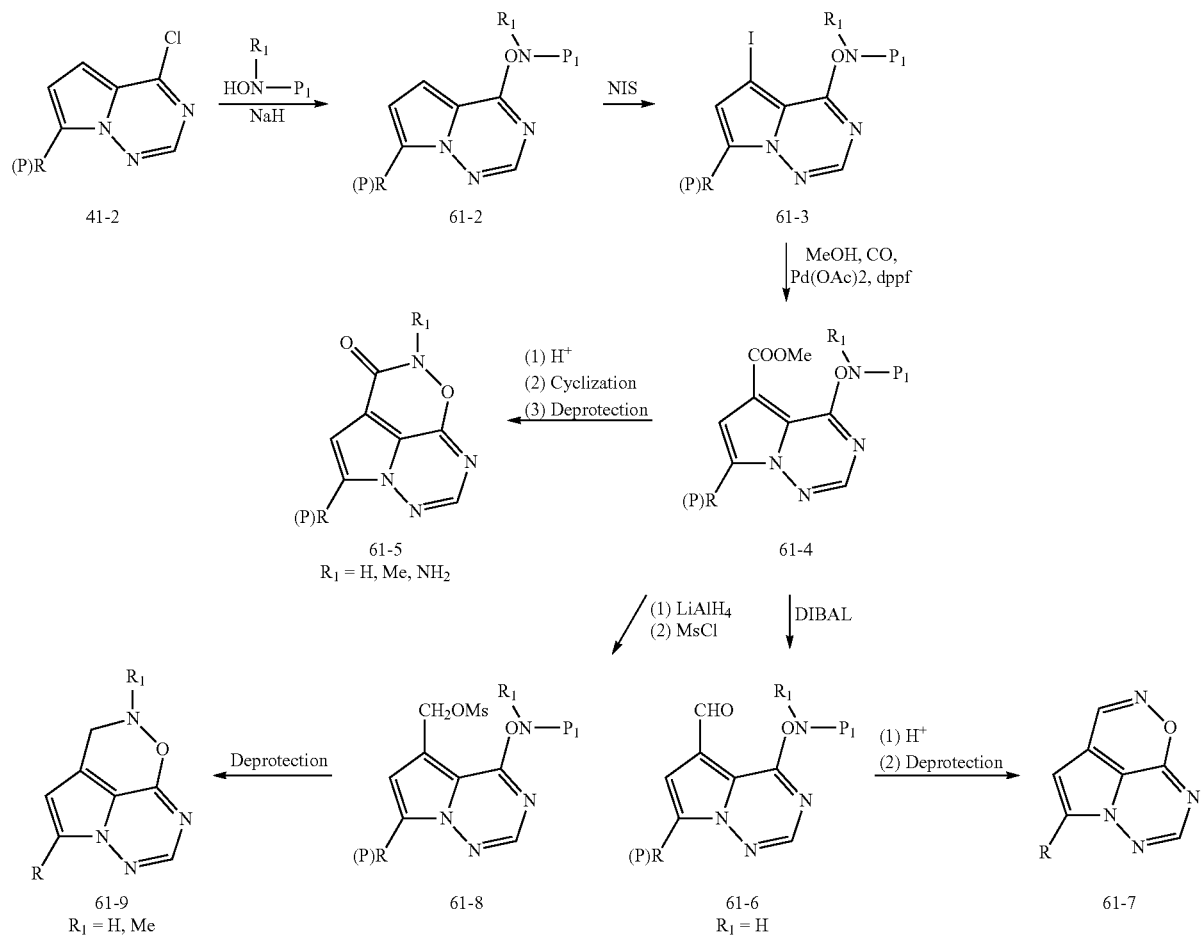

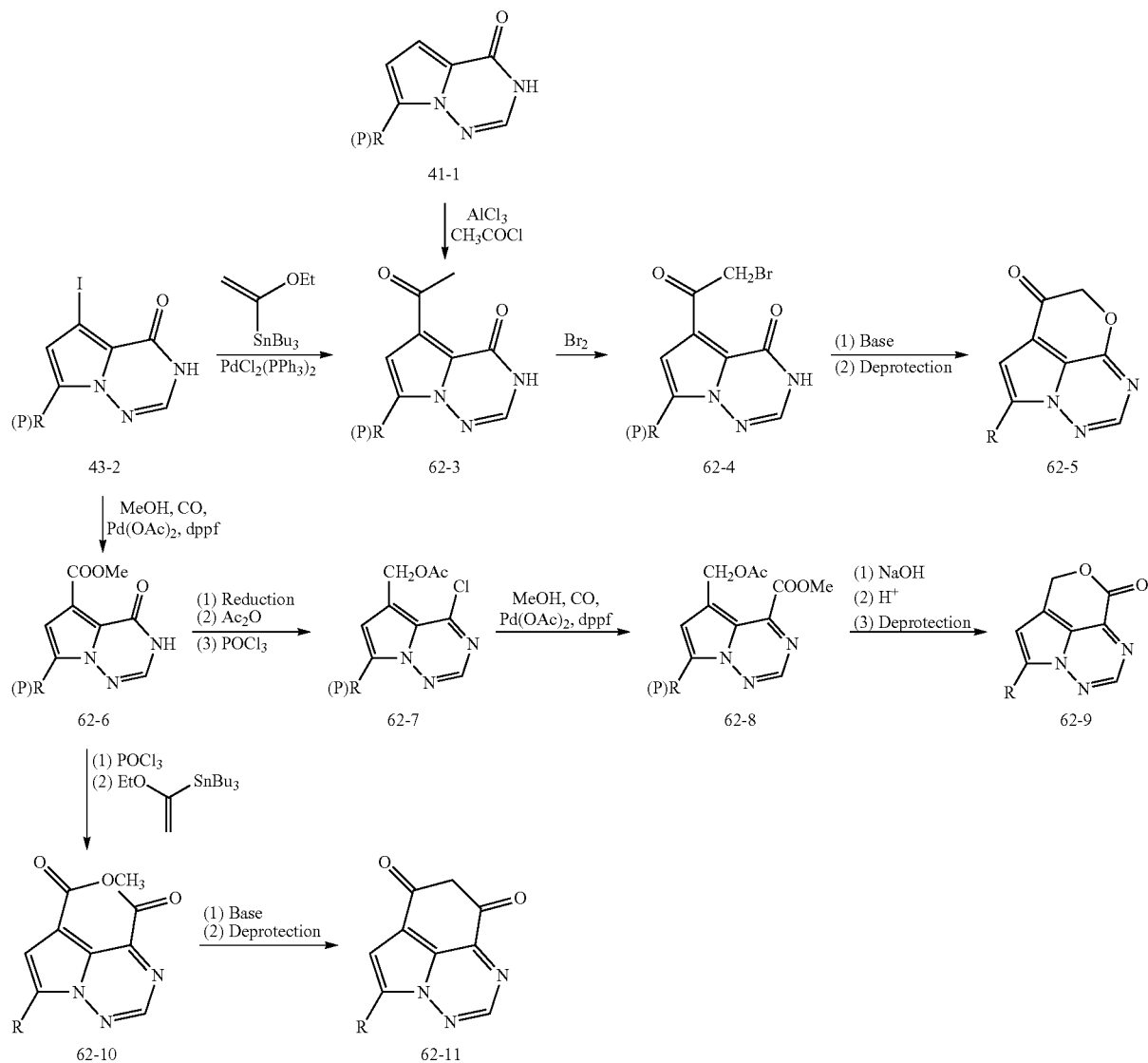
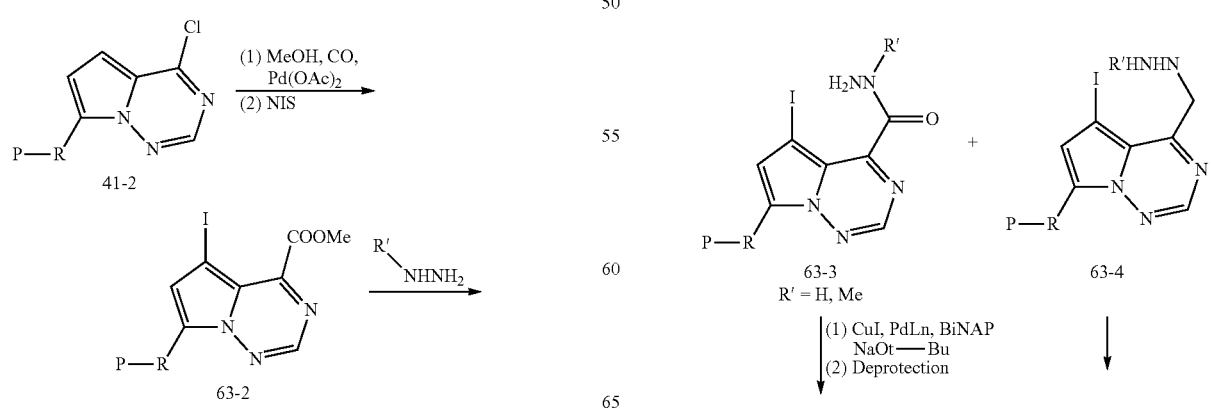

107
-continued
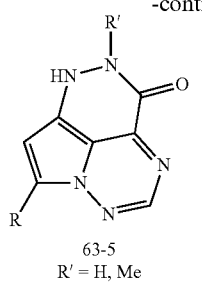
63-5
R' = H, Me
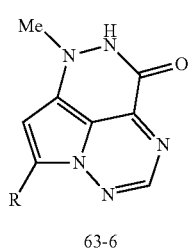
63-6
108
-continued
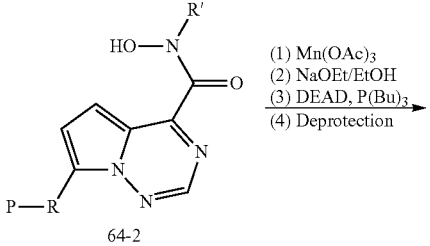
64-2
64-3
R' = H, Me, NH$_2$
Scheme 64.
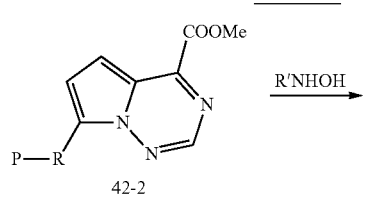
42-2
Scheme 65.
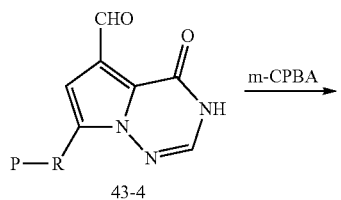
43-4
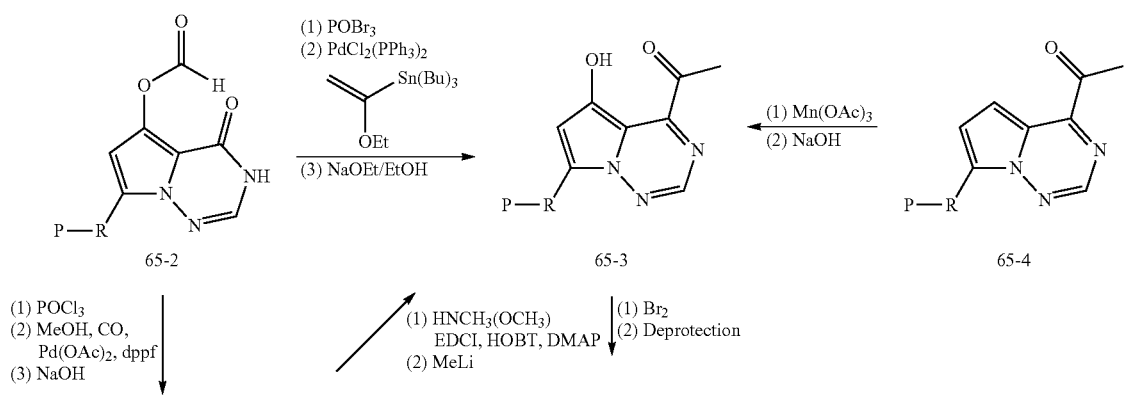
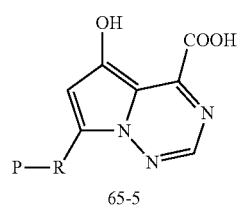
65-5
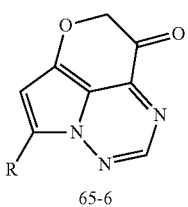
65-6

Scheme 66.
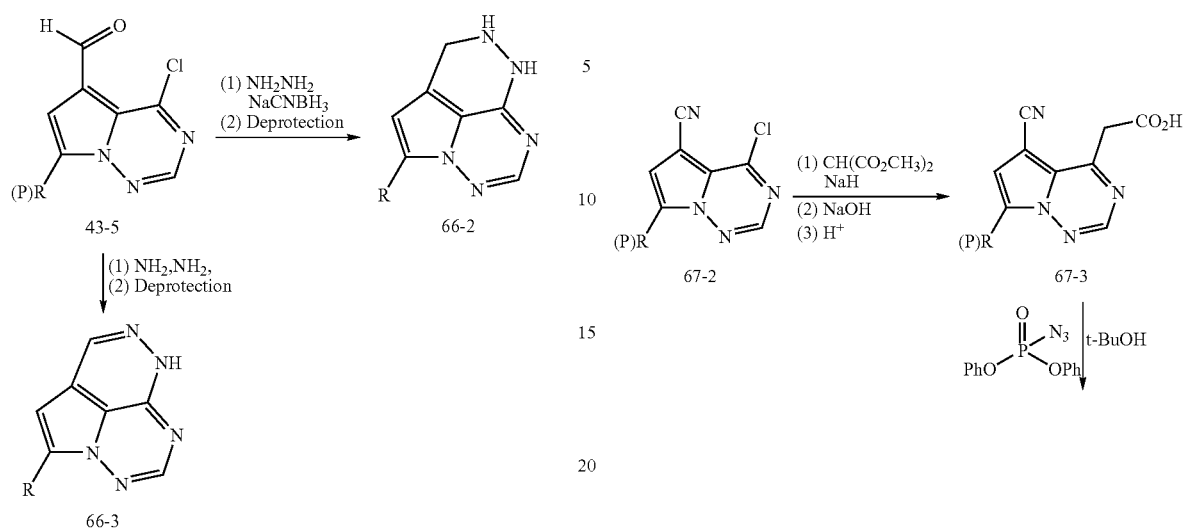
Scheme 67.
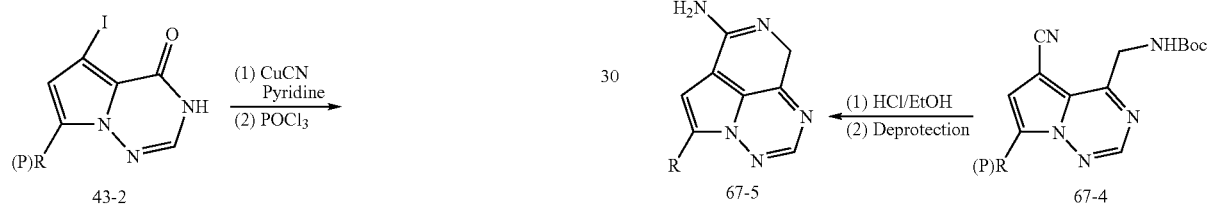
Scheme 68.
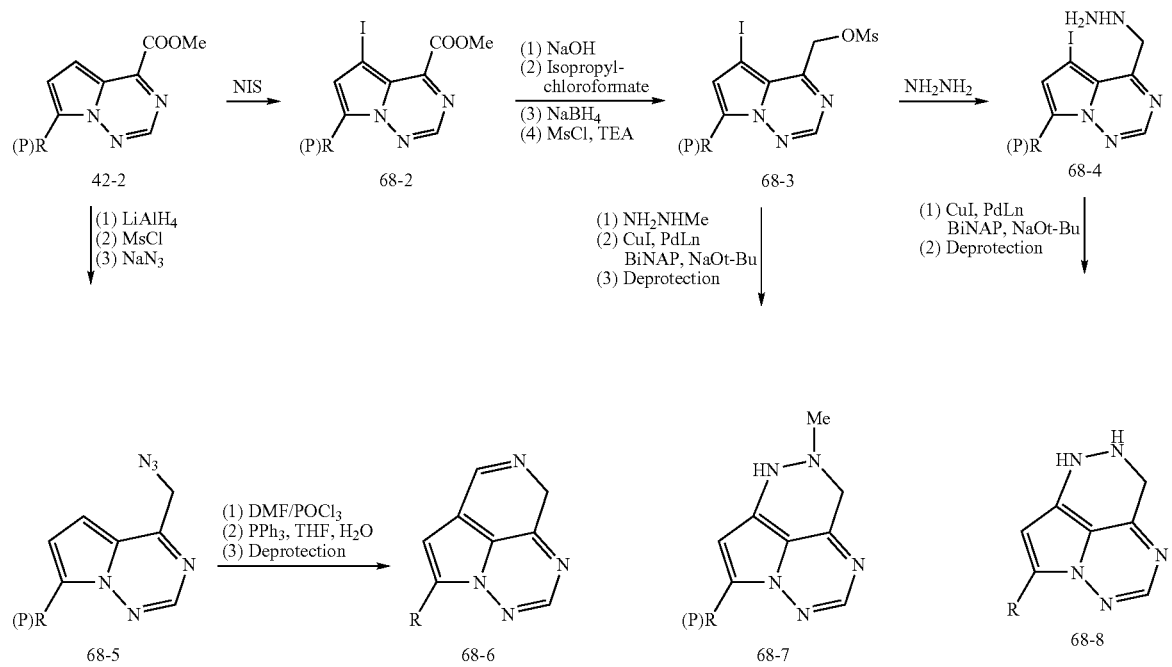

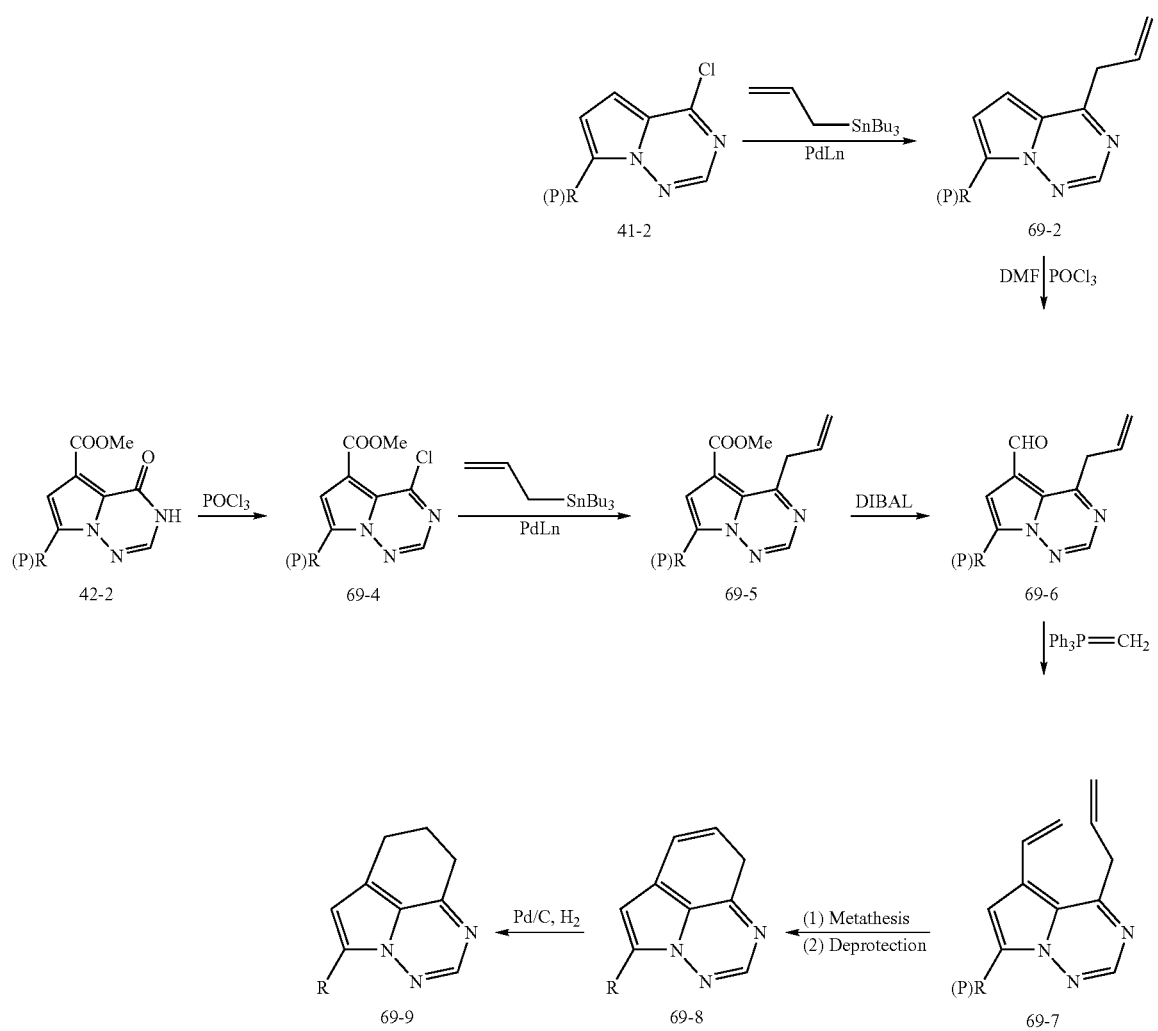
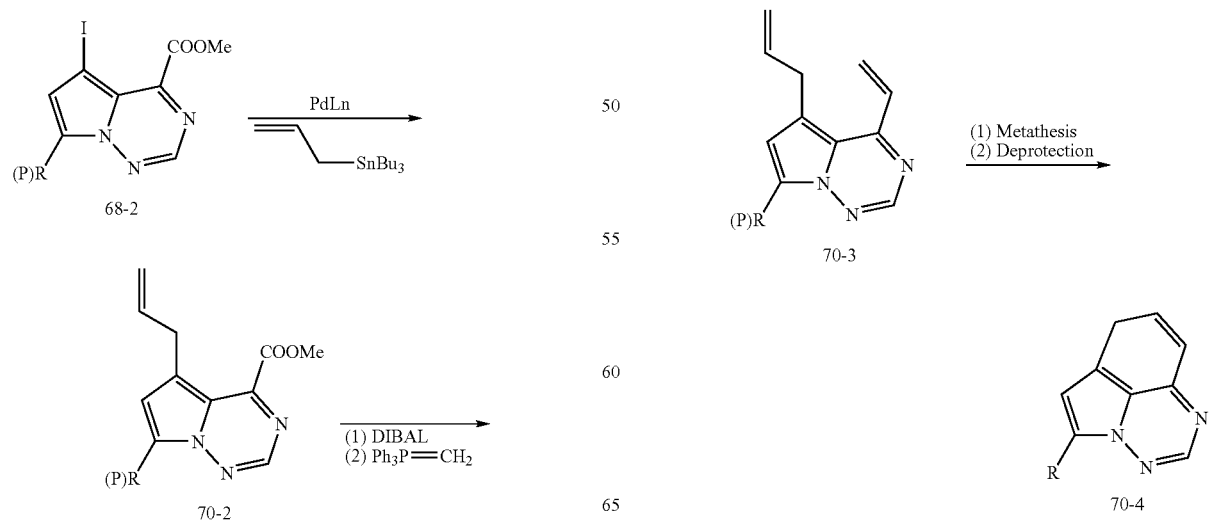

Scheme 71.
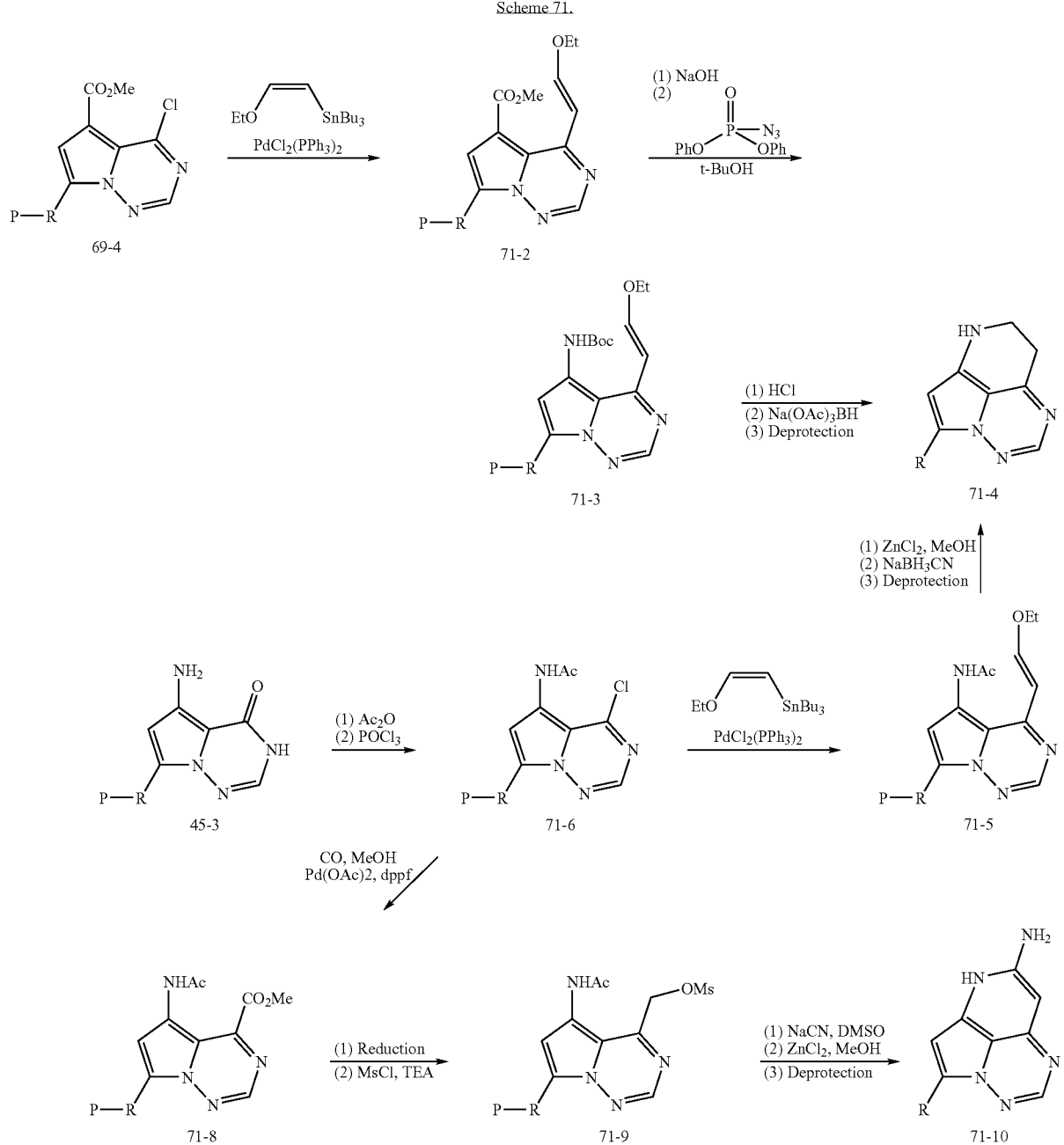
Scheme 72.
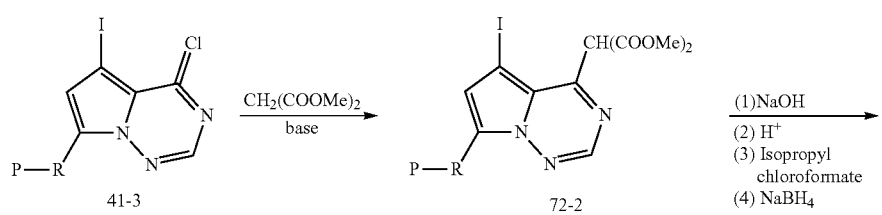

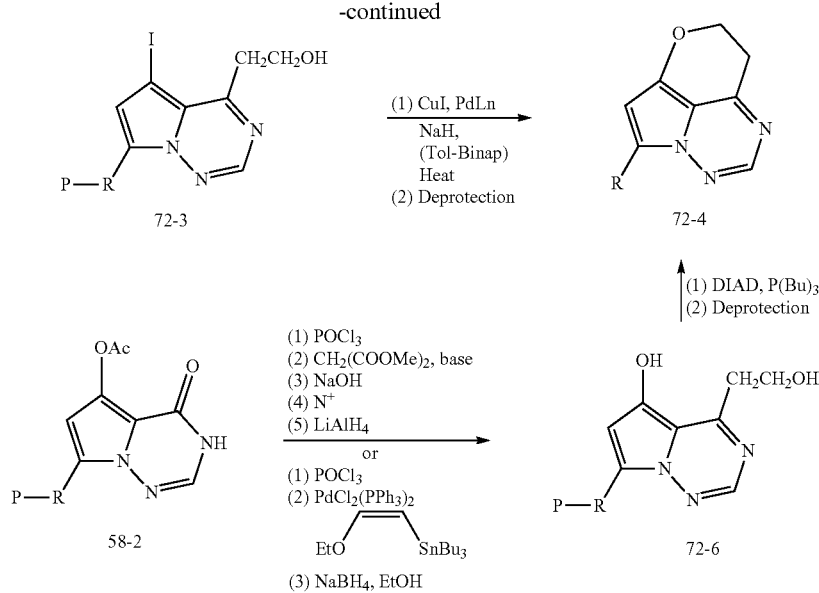
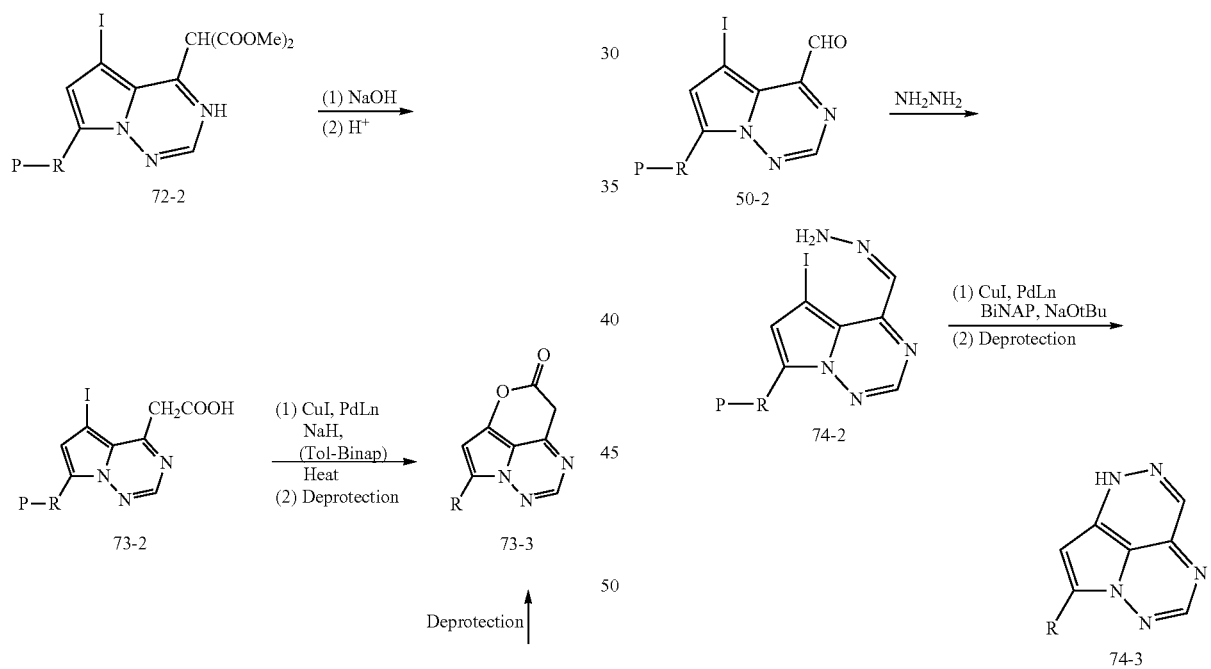
Scheme 73.
Scheme 74.
Scheme 75.
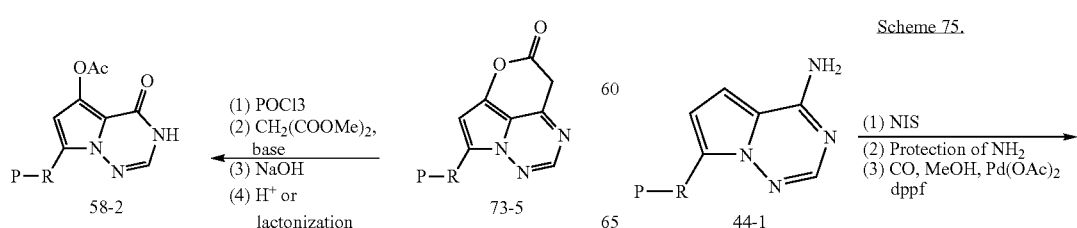

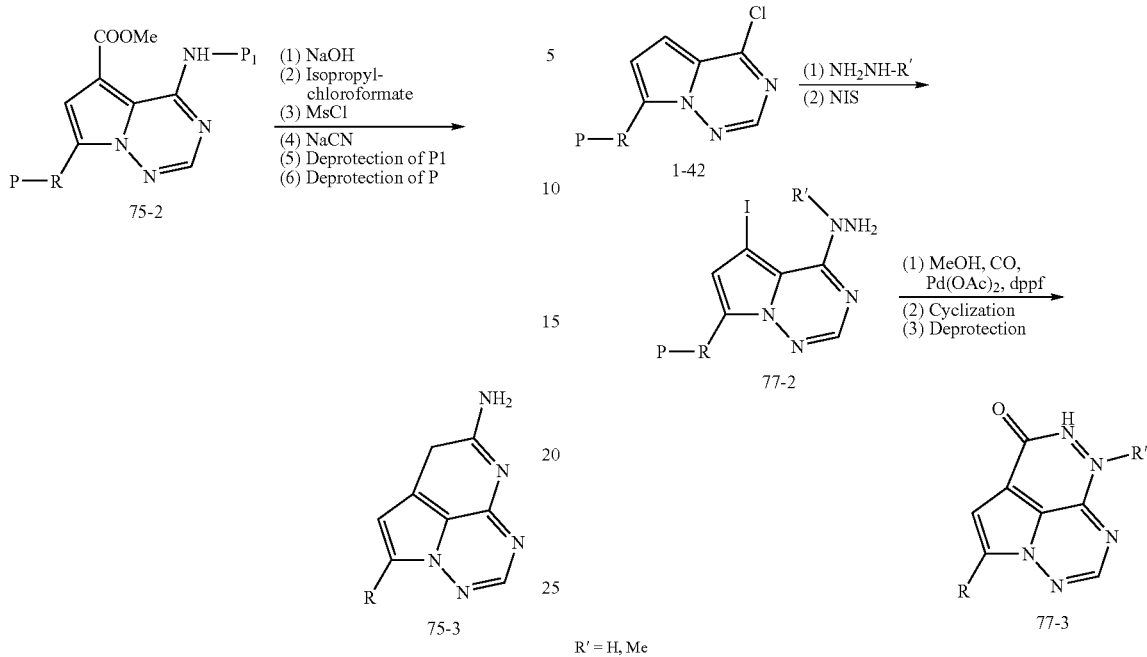
Scheme 77.
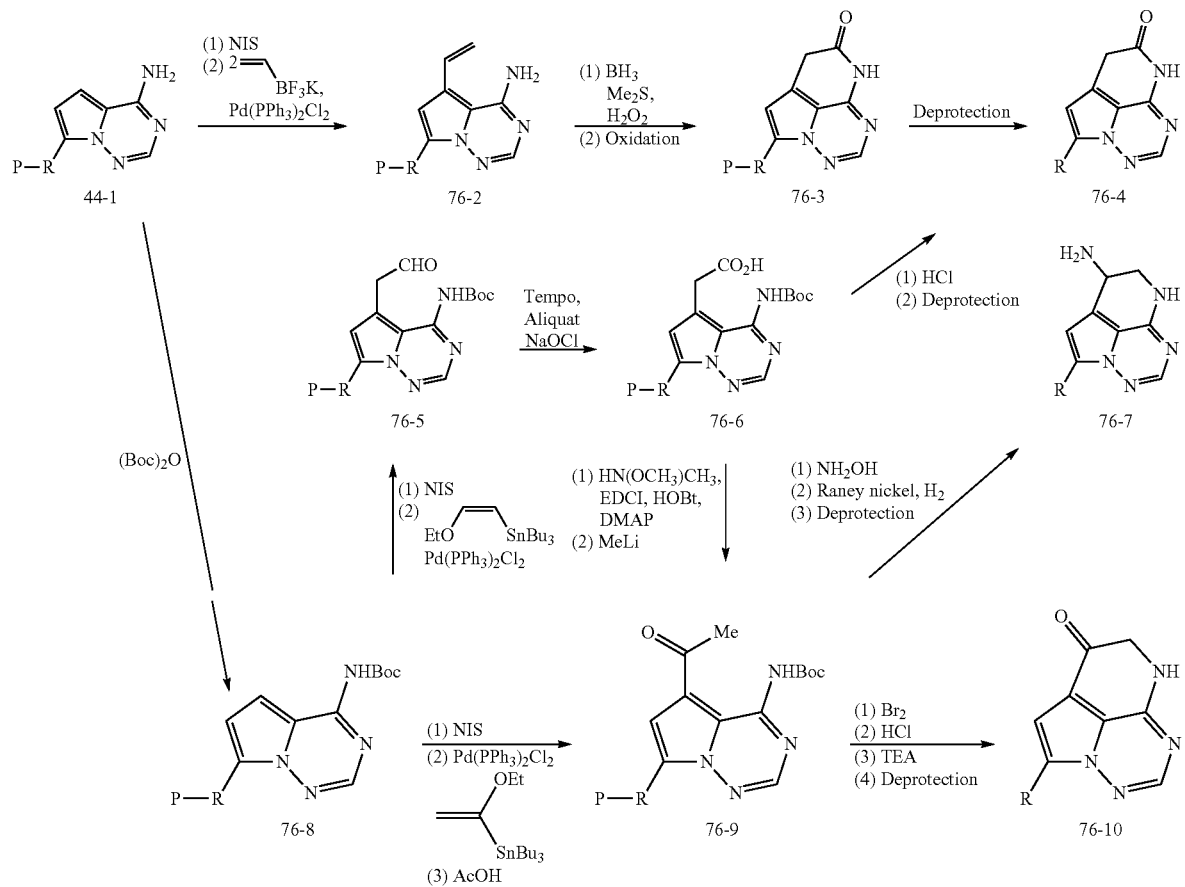
Scheme 76.

Scheme 78.
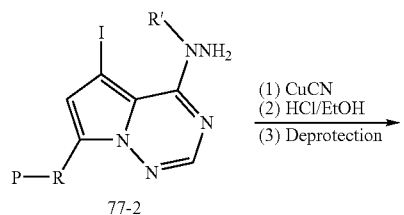
77-2
(1) CuCN
(2) HCl/EtOH
(3) Deprotection
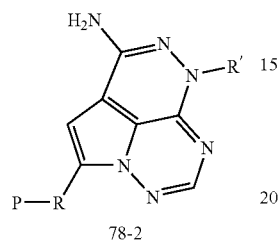
78-2
R' = H, Me
Scheme 79.
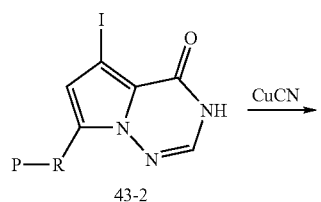
43-2
CuCN
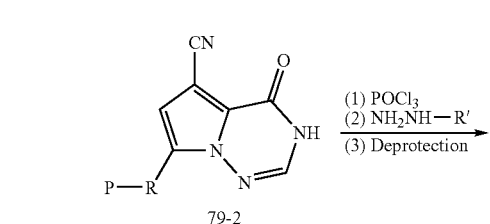
79-2
(1) POCl₃
(2) NH₂NH—R'
(3) Deprotection
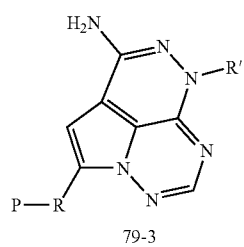
79-3
R' = H, Me
Scheme 80.
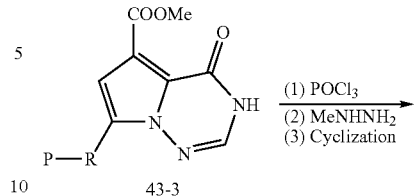
43-3
(1) POCl₃
(2) MeNHNH₂
(3) Cyclization
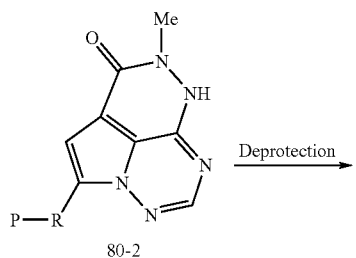
80-2
Deprotection
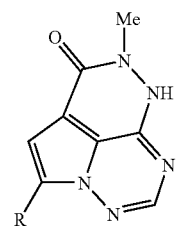
80-3
Scheme 81.
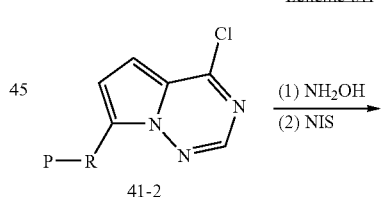
41-2
(1) NH₂OH
(2) NIS
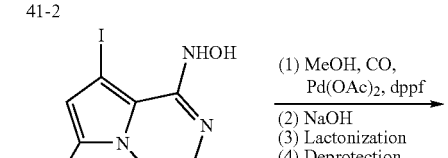
81-2
(1) MeOH, CO, Pd(OAc)₂, dppf
(2) NaOH
(3) Lactonization
(4) Deprotection
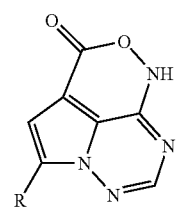
81-3

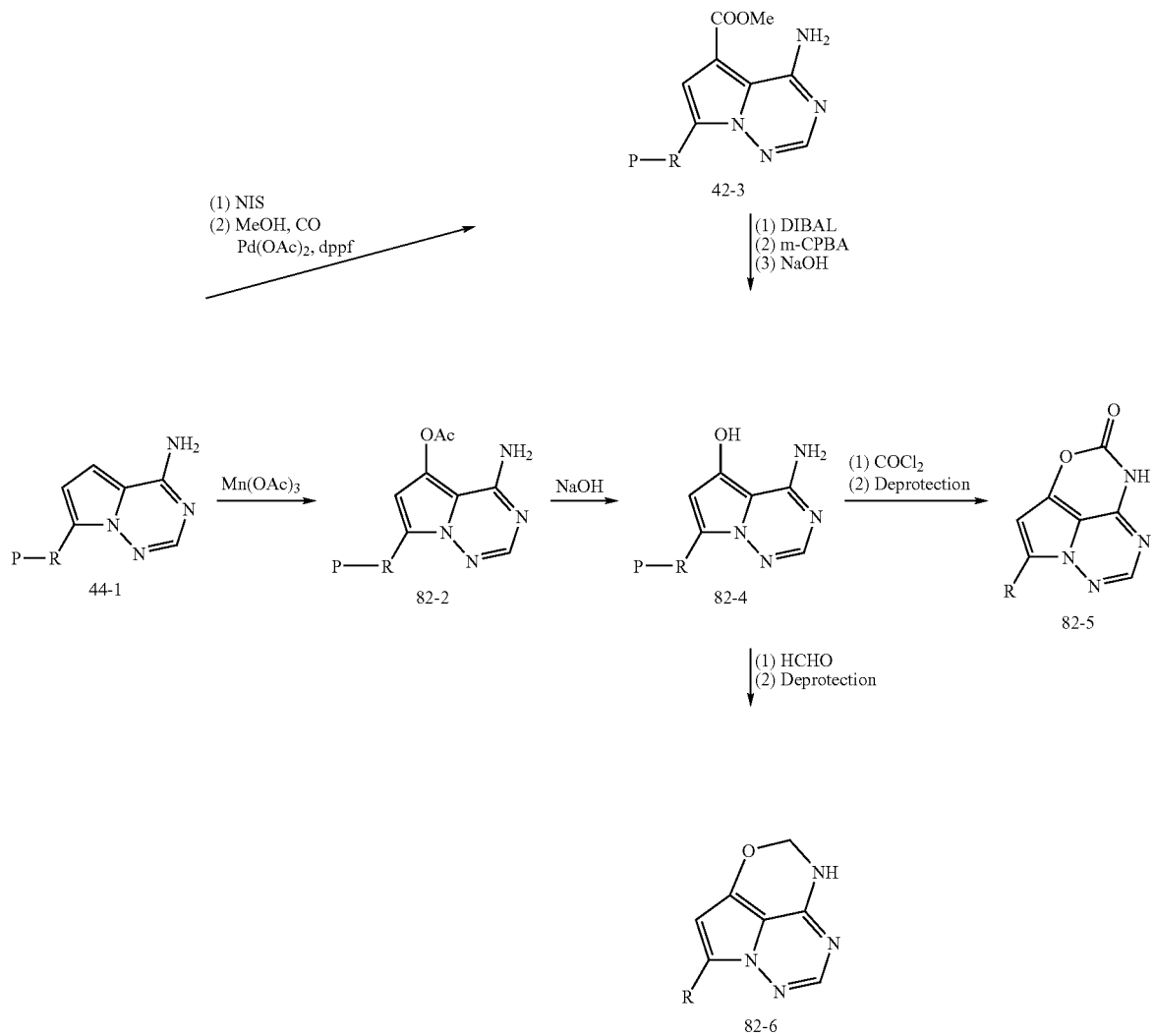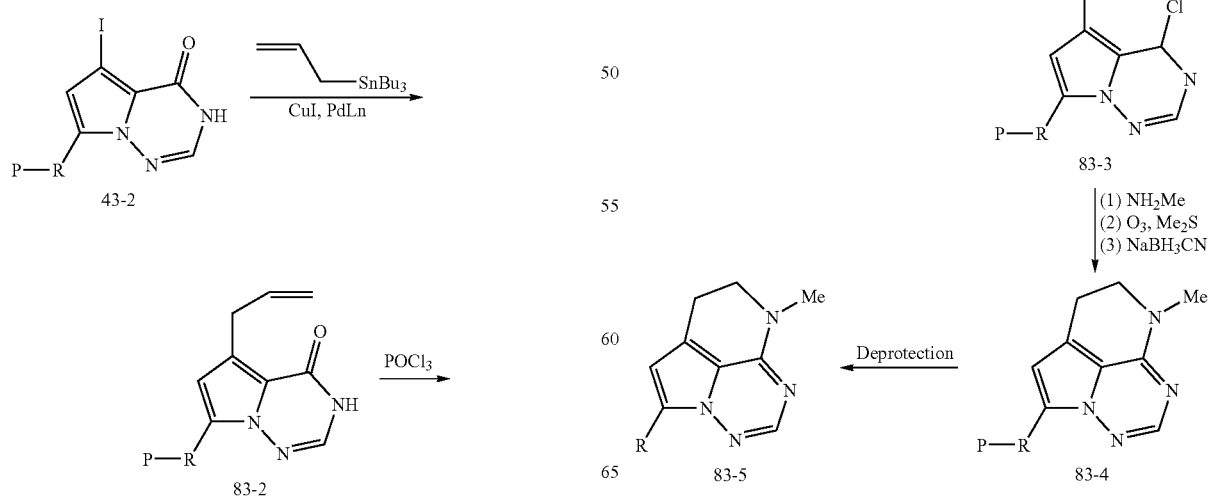

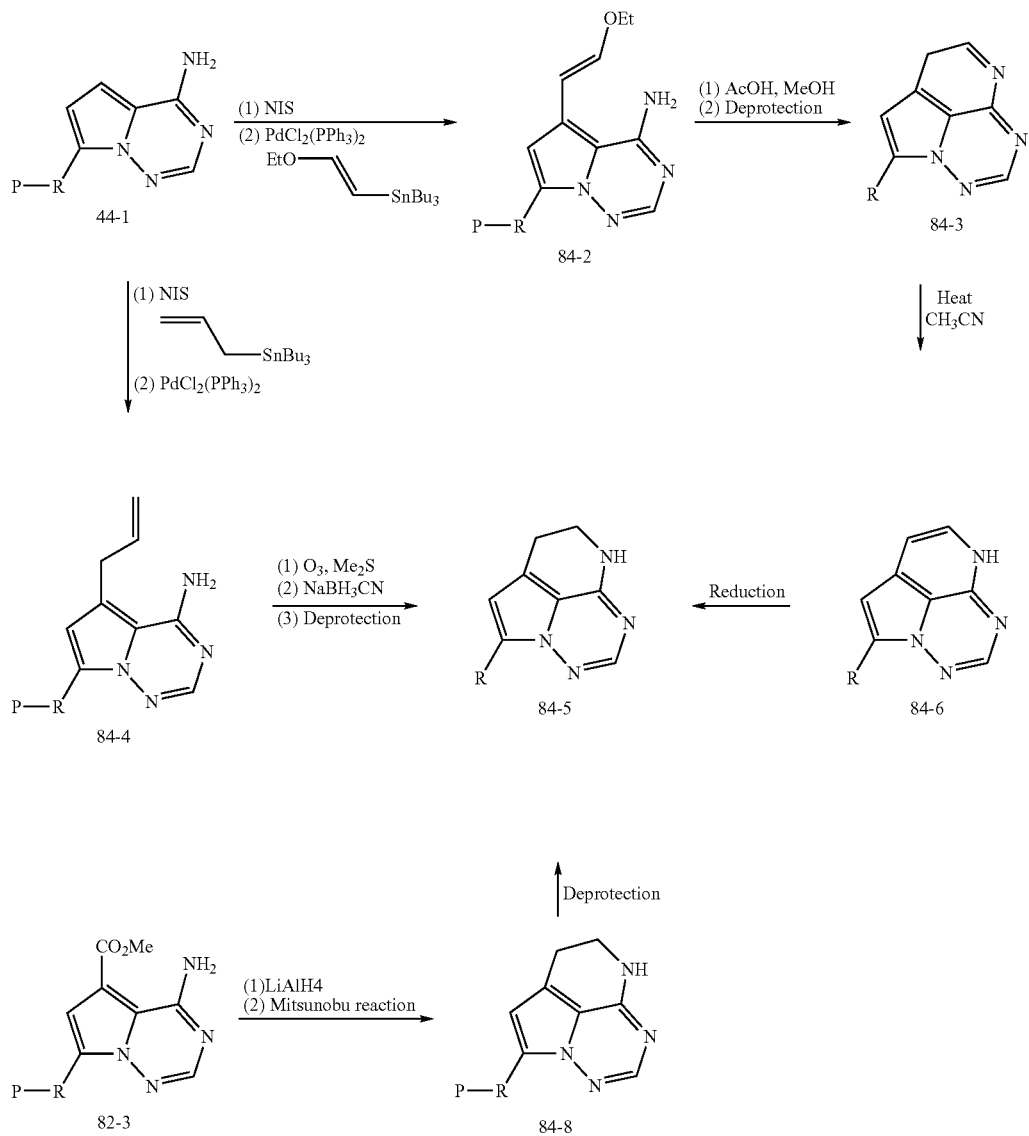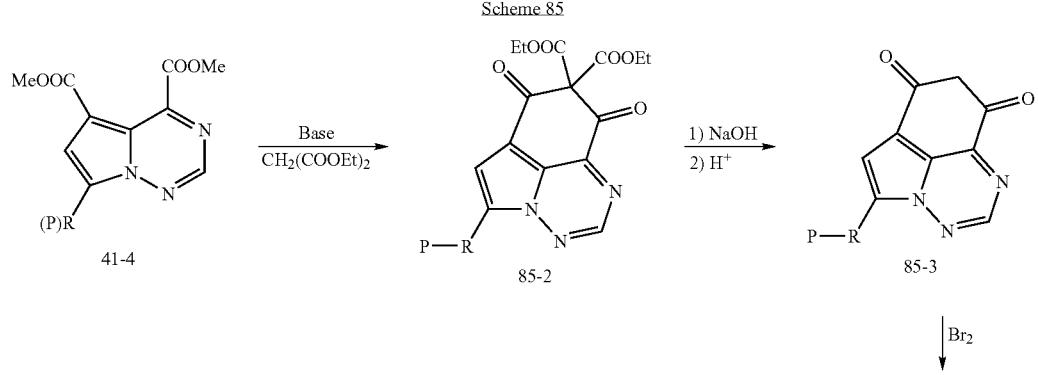

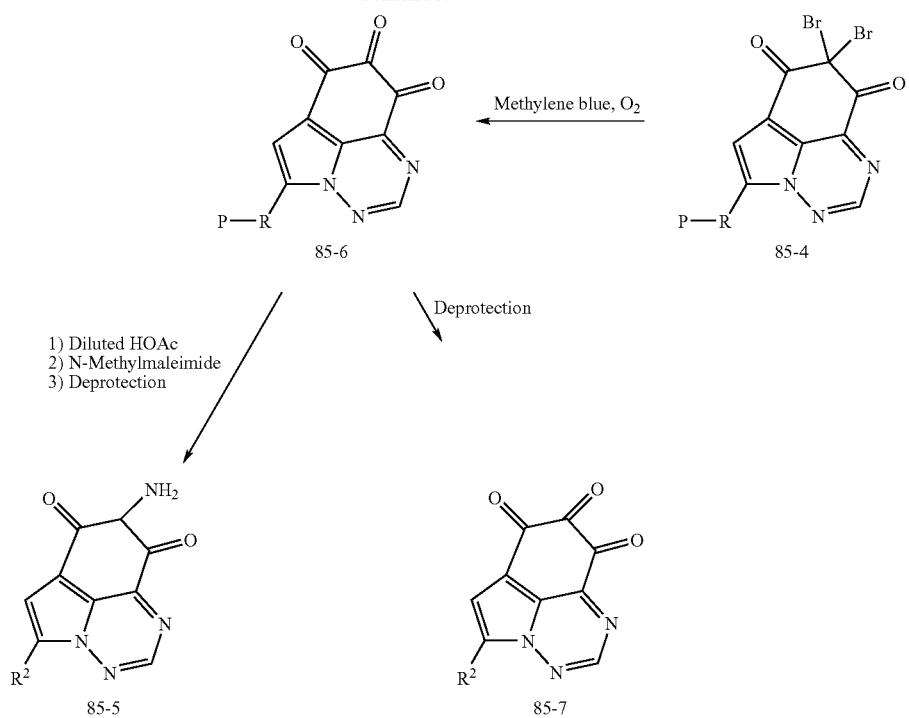
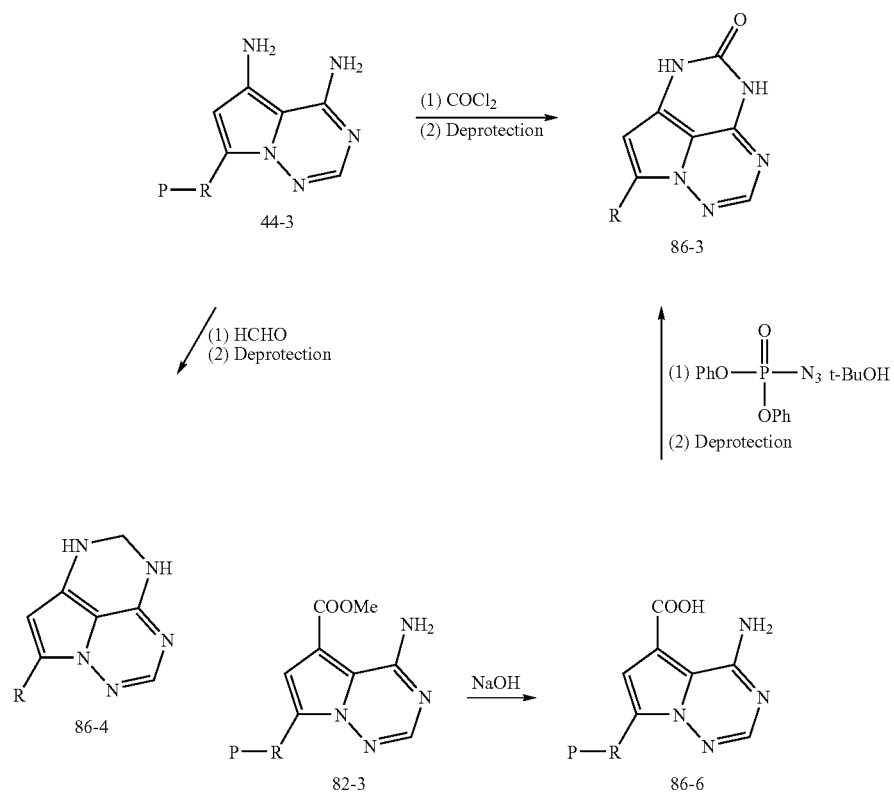
Scheme 86.

The invention will now be illustrated by the following non-limiting Examples.
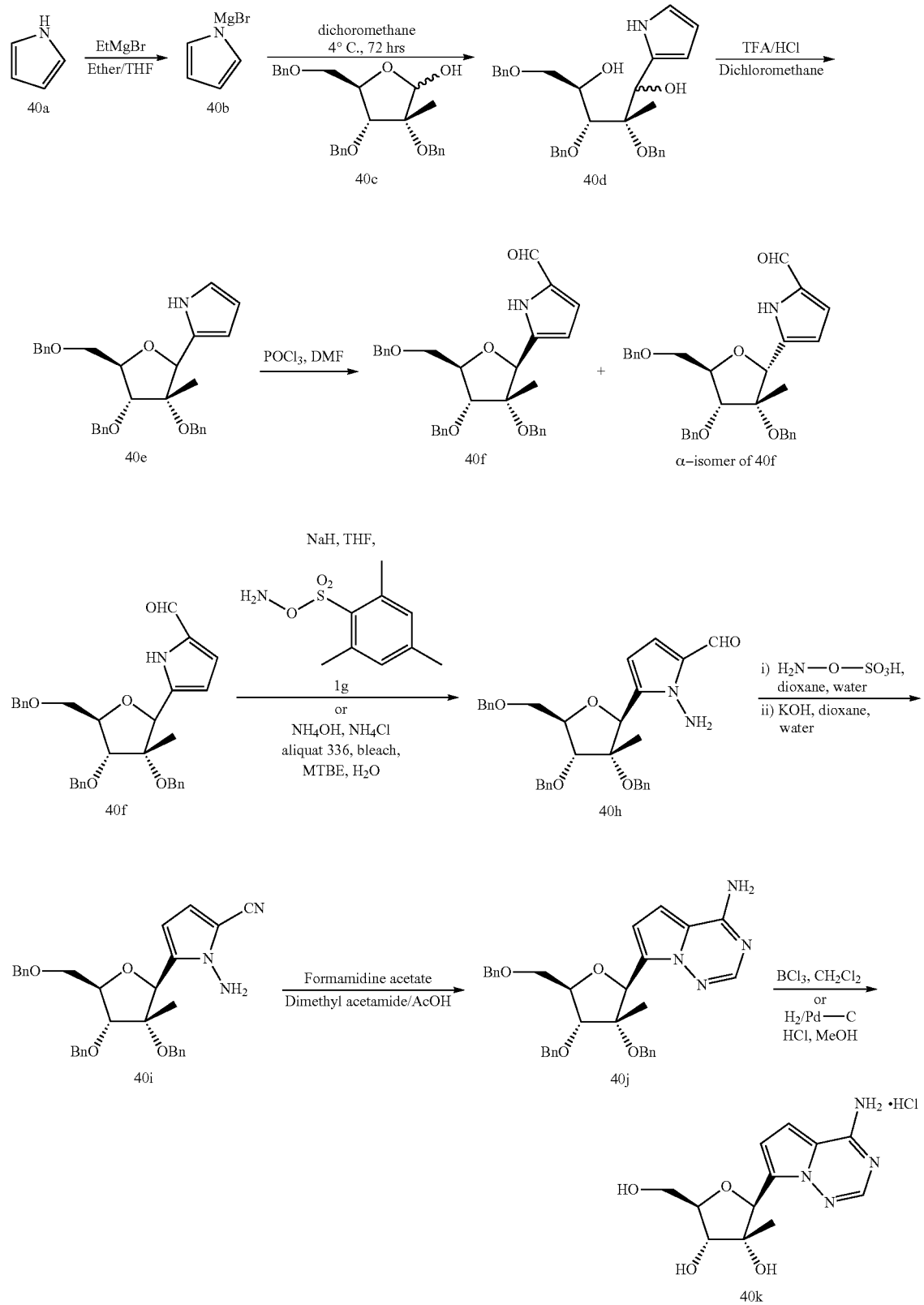
Scheme 40 for the Synthesis of Example 1

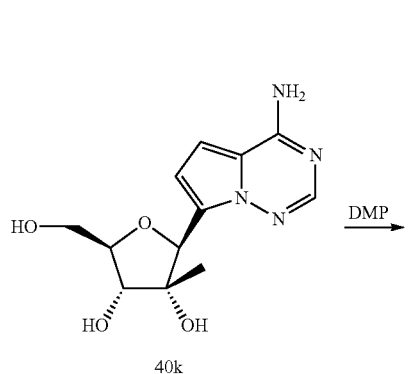
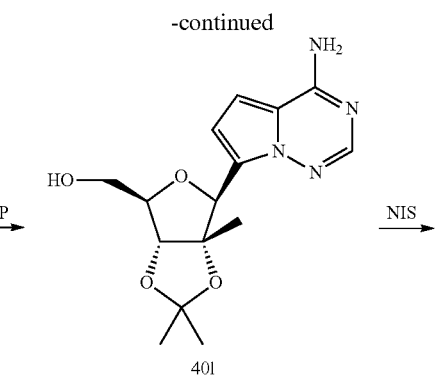
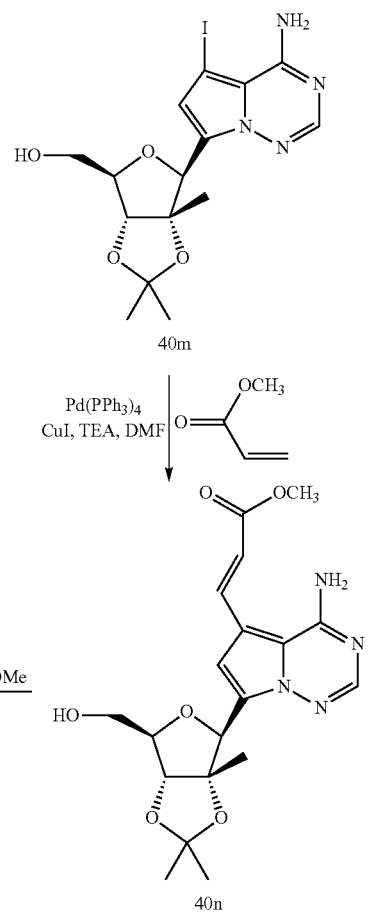

Example 1

Synthesis of 40p

To a solution of tricyclic product (40o, 0.1 g, 0.27 mmol) in methanol (2 mL) was added aqueous 1 N HCl (2 mL) and stirred at room temperature overnight. The reaction mixture was concentrated in vacuo to dryness. The residue obtained was triturated with methanol/ether and the solid obtained was collected by filtration washed with ether and dried in vacuo at acetone reflux temperature to furnish 40p (0.08 g, 90%) as a yellow solid; MP 240-242° C. $^1$H NMR (300 MHz, DMSO-$d_6$) δ 11.39-10.93 (m, 1H), 8.04 (s, 1H), 7.12 (d, J=11.9, 1H), 7.00 (s, 1H), 6.09 (s, 3H), 5.76 (d, J=11.9, 1H), 5.31 (s, 1H), 3.76 (d, J=10.6, 2H), 3.68 (s, 2H), 0.84 (s, 3H); MS (ES$^-$) 330.9.

The intermediate 40o was prepared as follows.

a. To a stirred solution of freshly distilled pyrrole (6.79 g, 100.89 mmol) in diethyl ether (100 mL) was added ethyl magnesium bromide (33.6 mL, 100.89 mmol, 3M solution in ether) slowly at 20° C. The reaction mixture was further stirred at 20° C. for 1 h and the solvent was removed under vacuum to give 40b. To 40b in dichloromethane (500 mL) at 0° C. was added a solution of 40c (WO 2006/050161, 10.96 g, 25.22 mmol) in dichloromethane (100 mL) and further stirred at 4° C. for 72 h. The reaction mixture was quenched by adding saturated solution of ammonium chloride (200 mL) and organic layer was separated. The aqueous layer was further extracted with dichloromethane (2×200 mL). The combined organic extracts were washed with water (2×50 mL) and brine (1×50 mL) and dried. After filtration, the filtrate containing 40d was treated with trifluoroacetic acid (4.14 g, 36.34 mmol) at 20° C. and stirred for 14 h. The reaction mixture was washed with water (2×100 mL) and brine (1×50 mL) and dried. After filtration, the filtrate was concentrated to give 12.5 g of crude 40e.

NOTE: THF was also used to make Grignard reagent instead of diethyl ether. THF was removed by distillation and the traces by azeotroping with toluene.

b. Phosphorusoxy chloride (19.33 g, 126.1 mmol) was added to N,N-dimethylformamide (100 mL) at 0° C. and stirred for 30 min. To this solution was added 40e (12.1 g, 25.22 mmol) in dichloromethane (50 mL) slowly over a period of 15 min. at 0° C. and stirring was continued for 1 h. The reaction mixture was quenched by adding saturated solution of sodium acetate (100 mL) and stirred for 30 min. The reaction mixture was concentrated to remove dichloromethane and the residue was diluted with ethyl acetate (200 mL). The organic layer was separated and washed with water (2×100 mL) and brine (1×50 mL) and dried. After filtration, the filtrate was concentrated and the residue was purified by flash chromatography using ethyl acetate in hexanes (0 to 12%) to give 2.92 g (22.6% from 40c) of 40f as dark brown syrup. MS (ES$^-$): 510.2.

NOTE: Only DMF was also used as solvent; there was no need of dichloromethane. For workup, 2N NaOH was used in place of sodium acetate.

c. To a stirred solution of above obtained 40f (2.5 g, 4.88 mmol) in tetrahydrofuran (50 mL) was added sodium hydride (0.39 g, 9.77 mmol, 60% dispersion in mineral oil) at 0° C. After stirring for 30 min at 0° C., O-(mesitylsulfonyl)hydroxylamine (40g, 1.15 g, 5.37 mmol, prepared by the method of Krause, J. G. *Synthesis*, 1972, 140) was added at 0° C. and further stirred for 2 h. The reaction mixture was quenched by adding water (20 mL) and extracted with ethyl acetate (2×50 mL). The combined organic extracts were washed with water (2×25 mL) and brine (1×25 mL) and dried. After filtration, the filtrate was concentrated to give 2.75 g of 1 h as dark syrup. MS (ES$^+$): 527.43.

The compound 40h can also be prepared as follows.

d. Aldehyde 40f (5.2 Kg, 10.16 moles) was dissolved in methyl tert-butyl ether (72.8 L) and charged into a clean SS reactor (600 L). Aliquot 336 (0.25 Kg, 0.61 mole) and ammonium chloride (6.53 Kg, 122.07 moles) were added to the reactor and reaction mixture was cooled to 0-5° C. Ammonium hydroxide (19.08 L, 137 moles, 28% solution in water) was added at 0-5° C. followed by addition of a cold (0-5° C.) sodium hydroxide solution (16.59 Kg in 66 L water, 414.75 moles) at the same temperature over a period of 3 h. Sodium hypochlorite (251 L, 222.58 moles, 6% solution) addition was started at 0° C. and during the addition the temperature was allowed to rise to 15° C. The reaction mixture was further stirred at room temperature for 2 h. TLC showed completion of the reaction. Ethyl acetate (104 L) was added to the reaction mixture and layers were separated. The aqueous layer was re-extracted with ethyl acetate (2×104 L). The combined organic layers were washed with water (52 L), sodium thiosulfate (2×156 L, 10% solution), water (52 L) and brine (70 L) and dried over sodium sulfate (10.4 Kg). After filtration, the filtrate was concentrated under vacuum below 40° C. to afford crude compound 40h (4.4 kg) as dark syrup.

e. To a stirred solution of 40h (2.56 g, 4.88 mmol) in dioxane (50 mL) was added water (15 mL) and cooled to 0° C. To this cooled solution at 0° C. was added hydroxylamine-O-sulfonic acid (1.93 g, 17.10 mmol). After stirring for 1 h, a cold solution of potassium hydroxide (2.19 g, 39.0 mmol) in water and dioxane (20 mL+20 mL) was added and further stirred at 0° C. for 1 h. The reaction mixture was diluted with ethyl acetate (100 mL), the organic layer was separated and washed with water (2×50 mL) and brine (1×50 mL) and dried. After filtration, the filtrate was concentrated to afford 2.6 g of 40i, which was used as such for the next step.

f. To a stirred solution of 40i (2.55 g, 4.88 mmol) in N,N-dimethylacetamide (70 mL) was added formamidine acetate (5.08 g, 48.88 mmol) and the reaction mixture was stirred at 140° C. for 3 h. Most of the N,N-dimethylacetamide was removed under vacuum and the residue was suspended in water (100 mL), which was extracted with ethyl acetate (2×250 mL). The combined organic extracts were washed with water (50 mL) and brine (50 mL) and dried. After filtration, the filtrate was concentrated and the residue was purified by flash chromatography using a mixture of ethyl acetate and methanol (9:1) in hexanes (0 to 30%) to provide impure compound (1.25 g). Further purification by chromatography on silica gel gave 0.48 g (17.8% from 40f) of 40j as a light brown solid. $^1$H NMR (CDCl$_3$): δ 7.87 (s, 1H), 7.43-7.21 (m, 15H), 6.88 (d, J=4.5 Hz, 1H), 6.50 (d, J=4.5 Hz, 1H), 5.87 (s, 1H), 5.36 (b, 2H, D$_2$O exchangeable), 4.83 (dd, J=31.8, 12.2 Hz, 2H), 4.68-4.52 (m, 4H), 4.40-4.35 (m, 1H), 4.04 (d, J=8.8 Hz, 1H), 3.88 (dd, J=10.9, 2.3 Hz, 1H), 3.69 (dd, J=11.1, 3.6 Hz, 1H), 1.00 (s, 3H). MS (ES$^+$): 551.40.

NOTE: Acetic acid and n-BuOH can also be used as solvent in place of dimethyl acetamide.

g. To a stirred solution of 40j (0.27 g, 0.484 mmol) in dichloromethane (25 mL) was added boron trichloride (4.84 mL, 4.84 mmol, 1M solution in dichloromethane) at −40° C. and the mixture was further stirred at −40° C. for 30 min and slowly brought to 0° C. in about 30 min and stirred at 0° C. for 20 min. The reaction was quenched by adding ethyl alcohol (50 mL) and concentrated under reduced pressure. Again, ethyl alcohol (50 mL) was added and concentrated. This operation was repeated 4 times. After concentration, the residue was dissolved in mixture of isopropyl alcohol and methanol (20 and 2 mL) and methanol was removed by concentration under vacuum. Solid separated out, which was collected by filtration and dried at 60° C. under vacuum to provide 39 mg (25%) of 40k as a colorless solid. $^1$H NMR (300 MHz, DMSO-d$_6$): δ 9.71 (bs, 1H, D$_2$O exchangeable), 8.99 (bs, 1H, D$_2$O exchangeable), 8.16 (s, 1H), 7.41 (d, J=4.5 Hz, 1H), 6.97 (d, J=4.7 Hz, 1H), 5.34 (s, 1H), 4.8-4.0 (m, 3H, D$_2$O exchangeable), 3.81-3.56 (m, 4H), 0.79 (s, 3H). MS (ES$^+$): 281.6.

Compound 40k can also be prepared as follows.

h. To a solution of compound 40j (128 g) in methanol (1.4 L), conc. HCl (130 mL) was added followed by 10% Pd/C (12 g) and the mixture was hydrogenated at 70 psi for 10 h. Since the compound precipitated out of the solution, water (500 mL) was added to the mixture and heated at 60° C. for about 1 h and filtered through a Celite pad. The Celite pad with palladium was re-suspended in a mixture of water (400 mL) and methanol (400 mL) and heated at 60° C. for about 1 h and again filtered through Celite. This operation was repeated until there was no compound left un-dissolved. The combined filtrates were concentrated under vacuum and recrystallized from water and ethanol (1:20) to afford 32.5 g of the desired product 40k as pale yellow crystals. The mother liquor was concentrated and recrystallized again to afford another crop of 5.6 g.

i. To a suspension of 40k (0.962 g, 3.4 mmol) in DMF (30 mL) and acetone (30 mL) was added 2,2-dimethoxypropane (4.2 mL, 98%, 34 mmol) and p-TsOH (650 mg, 98.5%, 3.4 mmol) and stirred at room temperature for 3 days. The reaction mixture was neutralized with 2N NaOH (aq.) and concentrated in vacuo to dryness. The residue was taken in water (90 mL) and extracted with ethyl acetate (3×30 mL). The organic layers were combined dried, filtered and concentrated in vacuo to dryness. The residue obtained was purified by flash column chromatography (silica gel, 40 g, eluting with 0-100% CMA 80 in chloroform) to give 40l (360 mg, 33%) as a yellow solid. $^1$H NMR (300 MHz, DMSO-d$_6$) δ 7.83 (s, 1H), 7.67 (s, 2H), 6.87 (d, J=4.5, 1H), 6.63 (d, J=4.4, 1H), 5.54 (s, 1H), 4.97 (t, J=5.7, 1H), 4.37 (d, J=2.4, 1H), 4.03-3.95 (m, 1H), 3.57 (dd, J=5.4, 9.7, 2H), 1.55 (s, 3H), 1.33 (s, 3H), 1.15 (s, 3H).

j. To a solution of 40l (375 mg, 1.2 mmol) in DMF (10 mL) was added iodosuccinimide (290 mg, 1.3 mmol) and stirred at room temperature overnight. The reaction mixture was diluted with water (30 mL) and extracted with ethyl acetate (3×25 mL). The organic layers were combined washed with water (25 mL), brine (25 mL), dried, filtered, and concentrated in vacuo. The residue obtained was purified by flash column chromatography (silica gel 12 g, eluting with 0-100% CMA 80 in chloroform) to give 40m (0.44 g, 83%) as an off white solid; MP 88-91° C. $^1$H NMR (300 MHz, DMSO-d$_6$) δ 7.88 (s, 1H), 6.91 (s, 1H), 5.50 (s, 1H), 4.98 (t, J=5.9, 1H), 4.38 (d, J=2.5, 1H), 4.02 (ddd, J=2.3, 4.7, 7.2, 1H), 3.63-3.52 (m, 2H), 1.54 (s, 3H), 1.33 (s, 3H), 1.10 (s, 3H); MS (ES$^-$) 444.83.

k. To a solution of 40m (2.6 g, 5.8 mmol) in DMF (70 mL) was added copper iodide (440 mg, 2.3 mmol), methyl acrylate (22.7 ml, 252 mmol), triethylamine (3.5 mL, 25.2 mmol) and tetrakis(triphenylphosphine)Palladium (1.85 g, 1.16 mmol) and heated with stirring at 70° C. for 3 days. The reaction was diluted with water (90 mL) and extracted with ethyl acetate (3×70 mL). The organic layers were combined washed with water (70 mL); brine (70 mL) dried, filtered, and concentrated in vacuo to dryness. The residue obtained was purified by flash column chromatography (silica gel 110 g, eluting with 0-100% 9:1 EtOAc:MeOH in hexane) to give 40n (0.43 g, 18%) as a yellow solid. $^1$H NMR (300 MHz, DMSO-$d_6$) δ 8.05 (d, J=15.4, 1H), 7.94 (s, 1H), 7.61 (s, 2H), 7.27 (s, 1H), 6.45 (d, J=15.3, 1H), 5.52 (s, 1H), 4.96 (t, J=6.0, 1H), 4.40 (d, J=2.4, 1H), 4.07-4.00 (m, 1H), 3.71 (s, 3H), 3.65-3.57 (m, 2H), 1.55 (s, 3H), 1.34 (s, 3H), 1.13 (s, 3H); MS (ES$^-$) 402.8.

l. To a freshly prepared solution of sodium methoxide (69 mg sodium in 30 ml methanol, 0.1 M) in methanol was added 40n (0.29 g, 0.72 mmol) and heated with stirring at reflux for 4 h and then at room temperature overnight. The reaction mixture neutralized with glacial acetic acid (0.18 mL) and the solid obtained was collected by filtration washed with methanol and dried in vacuo to furnish tricyclic product (40o, 0.126 g, 47%) as a yellow solid: $^1$H NMR (300 MHz, DMSO-$d_6$) δ 11.15 (s, 1H), 8.04 (s, 1H), 7.14 (d, J=11.9, 1H), 6.91 (s, 1H), 5.77 (d, J=11.9, 1H), 5.44 (s, 1H), 5.01 (t, J=5.5, 11H), 4.41 (d, J=2.3, 11H), 4.05 (td, J=2.3, 4.9, 1H), 3.58 (dt, J=5.6, 11.5, 2H), 1.55 (s, 3H), 1.34 (s, 3H), 1.12 (s, 3H); MS (ES$^-$) 370.9 (100%, M-1).

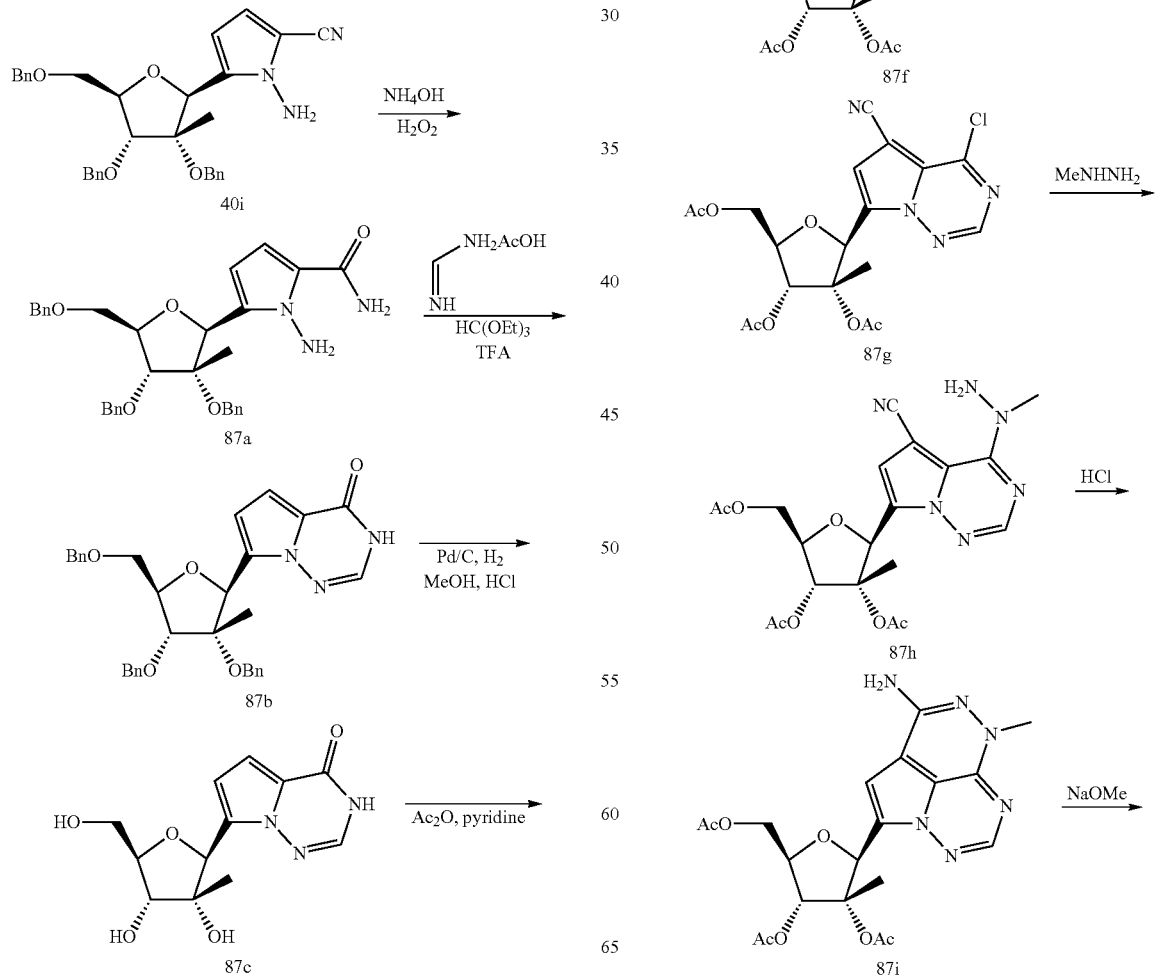

-continued

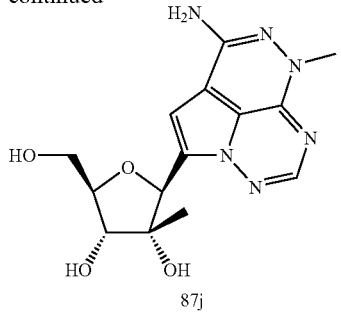

87j

Example 2

Synthesis of 87j

A solution of 87i (90 mg, 0.2 mmol) in methanol (1 mL) was added to a solution of freshly prepared NaOMe solution in methanol (0.17 M, 5 mL, 0.84 mmol) and stirred at room temperature overnight. The reaction mixture was neutralized by acetic acid (0.5 mL) and concentrated in vacuo. The residue obtained was purified by flash column chromatography (silica gel, 5 g, eluting with 0 to 100% CMA80 in chloroform) to yield 87j (27 mg, 48%) as a bright yellow solid; mp 212° C. $^1$H NMR (300 MHz, DMSO-$d_6$) 7.51 (s, 1H), 6.53 (s, 1H), 6.37 (s, 2H), 5.12 (s, 1H), 5.01 (d, J=6.9 Hz, 1H), 4.79 (s, 1H), 4.74 (t, J=5.4 Hz, 1H), 3.84-3.67 (m, 2H), 3.60 (dd, J=4.7, 10.4 Hz, 2H), 3.36 (s, 3H), 0.86 (s, 3H). MS (ES$^+$) 335.1.

The intermediate 87i was prepared as follows:

a. To a solution of 40i (11.1 g, 21.3 mmol) in EtOH (500 mL) was added conc. NH$_4$OH (28-30%, 200 mL) followed by dropwise addition of H$_2$O$_2$ (30% in H$_2$O, 7.2 mL). After the addition, the reaction mixture was stirred at room temperature overnight and concentrated in vacuo to dryness. The residue obtained was dissolved in chloroform (500 mL) washed with water, brine, dried, filtered and the filtrate was concentrated in vacuo to dryness. The residue obtained was purified by flash column chromatography (silica gel 300 g, eluting with 0-100%, ethyl acetate in hexane) to furnish 87a (3.45 g, 30%) as a brown oil. $^1$H NMR (300 MHz, DMSO-$d_6$/D$_2$O) δ 7.45-7.26 (m, 15H), 6.67 (d, J=4.3, 1H), 6.02 (d, J=4.3, 1H), 5.29 (s, 1H), 4.66-4.55 (m, 6H), 4.15 (s, 1H), 3.92 (d, J=6.6, 11H), 3.73 (m, 2H), 1.10 (s, 3H); MS (ES$^+$): 542.2.

b. To a solution of 87a (3 g, 5.5 mmol) in triethyl orthoformate (60 mL) was added TFA (0.43 mL, 5.5 mmol) and heated at 80° C. for 45 min. The reaction mixture was concentrated in vacuo to dryness and the residue obtained was purified by flash column chromatography (silica gel, eluting with hexanes/EtOAc, 1:0 to 1:1) to furnish 87b (1.783 g, 58.4%) as a light brown syrup. $^1$H NMR (300 MHz, DMSO-$d_6$): δ 11.70 (bs, 1H), 7.90 (d, J=3.1 Hz, 1H), 7.43-7.24 (m, 15H), 6.85 (d, J=4.4 Hz, 1H), 6.67 (d, J=4.4 Hz, 1H), 5.57 (s, 1H), 4.80-4.56 (m, 6H), 4.27-4.13 (m, 1H), 4.01-3.96 (m, 1H), 3.82 (dd, J=2.6, 11.0 Hz, 1H), 3.70 (dd, J=4.3, 11.0 Hz, 1H), 1.07 (s, 3H); MS (ES$^-$): 550.0.

c. To a solution of 87b (3.8 g, 6.9 mmol) in methanol (100 mL) was added Pd on carbon (10%, 580 mg) and conc. HCl (3 mL). The reaction mixture was hydrogenated at 50 psi for 4 h. The reaction mixture was filtered through a pad of Celite and the filtrate was concentrated in vacuo to dryness to furnish 87c (2.18 g, 100%) as brown syrup which was pure enough to be used as such for next step. MS (ES+): 282.1; (ES−): 280.4.

d. To a solution of 87c (2.18 g, 7.75 mmol) in pyridine (30 mL) was added acetic anhydride (6.5 mL, 69 mmol), DMAP (10 mg) and stirred at 70° C. overnight. The reaction mixture was cooled to room temperature, diluted with water (50 mL) and ethyl acetate (50 mL). The aqueous layer was separated and extracted with ethyl acetate (50 mL). The organic layers were combined, washed with water (50 mL), brine (50 mL), dried and concentrated in vacuo to dryness. The residue obtained was purified by flash column chromatography (silica gel 80 g, eluting with methanol in chloroform 0-20%) to afford 87d (1.88 g, 70%) as off white solid, MP 147-154° C. $^1$H NMR (300 MHz, DMSO-$d_6$): δ 11.78 (s, 1H), 8.32 (s, 1H), 7.93 (s, 1H), 6.93 (d, J=4.4 Hz, 1H), 6.62 (d, J=4.4 Hz, 1H), 5.60 (s, 1H), 5.20 (d, J=4.1 Hz, 1H), 4.47-4.32 (m, 1H), 4.21 (dd, J=7.8, 19.6 Hz, 1H), 2.70 (s, 6H), 2.01 (s, 3H), 1.87 (s, 3H); MS (ES$^+$): 430.0 (M+Na).

e. To a solution of 87d (1.08 g, 2.66 mmol) in dichloromethane (75 mL) at 0° C. was added N-iodosuccinimide (719.2 mg, 3.2 mmol). The reaction was allowed to warm to room temperature overnight and concentrated in vacuo. The residue obtained was purified by flash column chromatography (silica gel 40 g, eluting with 0 to 100% ethyl acetate in hexane) to afford 87e (1.09 g, 77%) as an orange solid; mp 212° C. $^1$H NMR (300 MHz, DMSO-$d_6$) δ 11.83 (s, 1H), 7.94 (s, 1H), 6.81 (s, 1H), 5.56 (s, 1H), 5.17 (d, J=4.2 Hz, 1H), 4.35 (s, 1H), 4.20 (d, J=11.7 Hz, 2H), 2.07 (d, J=2.2 Hz, 6H), 2.00 (s, 3H), 1.39 (s, 3H).

f. To hot refluxing pyridine (14 mL) was added a solution of 87e (1.09 g, 2.04 mmol) in pyridine (2 mL) and copper cyanide (2.15 g, 24 mmol). The reaction mixture was heated at reflux overnight, cooled to room temperature and diluted with water (50 mL) and ethyl acetate (50 mL). The insoluble inorganic impurities were removed by filtration; the aqueous layer was separated and extracted with ethyl acetate (2×100 mL). The organic layers were combined washed with brine (100 mL), dried, filtered, and concentrated in vacuo. The residue obtained was purified by flash column chromatography (silica gel, 20 g, eluting with 10 to 90% [9:1] of ethyl acetate:methanol in hexane) to yield 87f (270 mg, 31%) as a colorless oil. $^1$H NMR (300 MHz, DMSO-$d_6$) δ 12.48 (s, 1H), 8.16 (s, 1H), 7.21 (s, 1H), 5.56 (s, 1H), 5.17 (s, 1H), 4.35 (s, 1H), 4.17 (s, 2H), 2.07 (s, 6H), 1.99 (s, 3H), 1.38 (s, 3H).

g. A solution of 87f (460 mg, 1.06 mmol) in phosphorous oxychloride (10 mL) was heated at reflux temperature for 2 h. The reaction was cooled with ice water, quenched with ice water and stirred vigorously until all phosphorous oxychloride was destroyed. This aqueous layer was extracted with ethyl acetate (3×100 mL). The organic layers were combined washed with brine (100 mL), dried, filtered, and concentrated in vacuo to yield 87g (653 mg).

h. To a solution of crude 87g in chloroform (15 mL) and ethanol (30 mL) was added methyl hydrazine (0.1 mL, 1.74 mmol) and stirred at room temperature overnight. The reaction mixture was concentrated in vacuo and the residue purified by flash column chromatography (silica gel, 12 g, eluting with 0 to 100% [9:1] of ethyl acetate:methanol in hexane) to yield 87h (140 mg, 28%) as an yellow solid. $^1$H NMR (300 MHz, DMSO-$d_6$) δ 8.07 (s, 1H), 7.27 (s, 1H), 5.75 (s, 1H), 5.48 (s, 2H), 5.21 (d, J=4.2 Hz, 1H), 4.37 (s, 1H), 4.22 (d, J=11.6 Hz, 2H), 3.36 (d, J=11.0 Hz, 3H), 2.08 (s, 6H), 1.99 (s, 3H), 1.40 (s, 3H).

i. To a solution of 87h (140 mg, 0.29 mmol) in ethanol (20 mL) was added concentrated hydrochloric acid (2 drops) and heated at reflux temperature for 2 h. The reaction mixture was concentrated in vacuo to give 87i (90 mg, 64.3%).

Scheme 88 for the Synthesis of Example 3

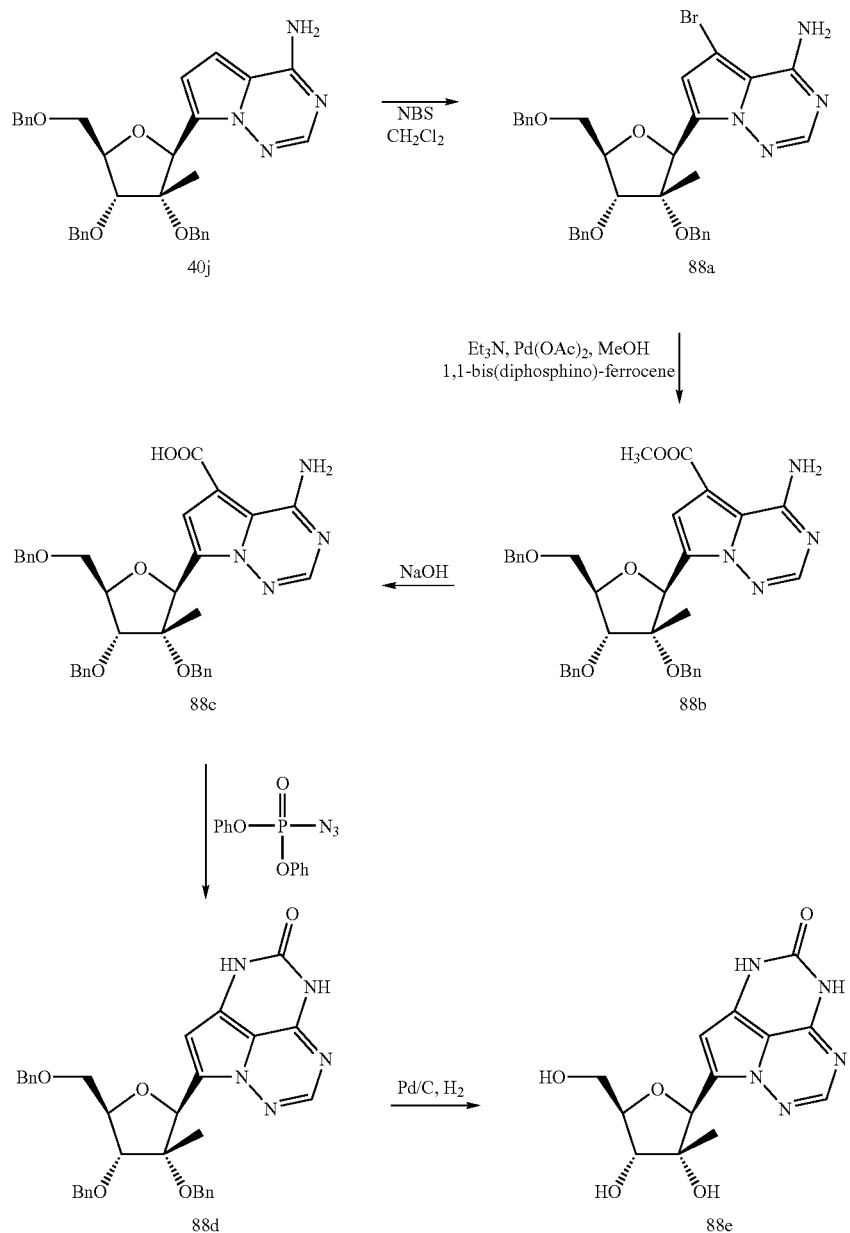

Example 3

Synthesis of 88e

To a solution of 88d (1.31 g, 2.21 mmol) in MeOH (110 mL) and EtOAc (60 mL) was added 1N HCl (9.5 mL), Pd/C (10%, 200 mg) and hydrogenated at 60 psi for 24 h. The reaction mixture was filtered through Celite, and the filtrate was concentrated in vacuo. The residue obtained was purified by flash column chromatography (silica gel, eluting with CMA80/CMA50 1:0 to 1:1) to give 88e (489 mg) as a yellow solid. The product obtained was triturated with water, collected by filtration and dried in vacuo to furnish 88e (251 mg, 35%) as an off-white solid; mp 210° C. $^1$H NMR (300 MHz, DMSO-$d_6$): 11.07 (bs, 1H), 10.53 (bs, 1H), 7.70 (s, 1H), 6.18 (s, 1H), 5.16 (s, 1H), 4.95 (d, J=6.1 Hz, 1H), 4.84 (t, J=5.2 Hz, 1H), 4.80 (s, 1H), 3.80-3.65 (m, 3H), 3.61-3.50 (m, 1H), 0.84 (s, 3H); MS (ES$^+$): 322.1.

The intermediate 88d was prepared as follows:

a. To a solution of 40j (100 mg, 0.18 mmol) in CH$_2$Cl$_2$ (9 mL) cold (ice water bath) was added NBS (32 mg, 0.18 mmol) and stirred at room temperature for 1 h. The reaction mixture was concentrated in vacuo and the residue obtained was purified by flash column chromatography (silica gel, eluting with chloroform/methanol, 1:0 to 20:1) to furnish 88a (102 mg, 90%) as a yellow solid. $^1$H NMR (300 MHz, DMSO-$d_6$): δ 7.89 (s, 1H), 7.42-7.25 (m, 15H), 6.91 (s, 1H), 5.64 (s, 1H), 4.74 (s, 2H), 4.66-4.52 (m, 4H), 4.22-4.16 (m, 1H), 4.03 (d, J=8.7 Hz, 1H), 3.90-3.68 (m, 2H), 1.05 (s, 3H); MS (ES$^+$): 631.3.

b. A solution of 88a (35 g, 55.6 mmol) in methanol (350 mL) in a 2-L stainless steel bomb was added triethylamine (7.7 mL, 55.6 mmol), Pd(OAc)$_2$ (3.5 g) and 1,1-bis(diphosphino)-ferrocene (3.5 g). The bomb was vacuum flushed and charged with CO to 150 psi. The reactor was heated with stirring at 150° C. overnight and cooled to room temperature. The catalyst was filtered through a pad of Celite and concentrated in vacuo to obtain crude product. The crude was purified by flash column chromatography (silica gel 1.2 kg, eluting with ethyl acetate in Hexane (0-50%, 2 L each) to give 10.7 g of 88b as yellow semisolid. $^1$H NMR (300 MHz, DMSO-d$_6$): δ 9.05 (s, 1H, exchangeable), 8.41 (s, 1H, exchangeable), 8.07 (s, 1H), 7.49-7.20 (m, 16H), 5.66 (s, 1H), 4.76 (s, 2H), 4.72-4.45 (m, 4H), 4.19 (s, 1H), 4.09-3.98 (m, 1H), 3.86 (d, J=8.9, 1H), 3.76 (s, 3H), 3.75-3.68 (m, 1H), 1.09 (s, 3H); MS (ES$^+$): 609.1.

c. To a solution of 88b (8.5 g, 14 mmol) in methanol (140 mL) was added THF (140 mL) and 1 N NaOH (140 mL). The reaction was heated with stirring at 40° C. for 1.5 h. The reaction mixture was concentrated in vacuo to remove methanol and THF. The pH was adjusted to 6 using 2.5N HCl and the aqueous layer was extracted twice with ethyl acetate (500 mL and 200 mL). The organic layers were combined, dried and concentrated in vacuo to furnish crude product. The crude was purified by flash column chromatography (silica gel 200 g, eluting with 0-50% CMA 80 in chloroform) to furnish 88c (9.5 g, 100%) as a light yellow solid; MP 164° C. $^1$H NMR (300 MHz, DMSO-d$_6$) δ 13.37-12.95 (bs, 1H), 9.42 (s, 1H), 8.32 (s, 1H), 8.04 (s, 1H), 7.35 (dd, J=13.6, 23.4 Hz, 15H), 5.66 (s, 1H), 4.68 (d, J=42.2 Hz, 6H), 4.18 (s, 1H), 4.01 (d, J=8.4 Hz, 1H), 3.83 (s, 2H), 3.33 (s, 1H), 1.07 (s, 3H); MS (ES$^+$): 595.0.

d. To a solution of 88c (2 g, 3.36 mmol) in benzene (30 mL) was added triethylamine (0.54 mL, 3.87 mmol) and diphenyl phosphoryl azide (0.82 mL, 97%, 3.68 mmol) and heated at reflux for 14 h. The reaction mixture was cooled to room temperature and quenched with 1M NaHCO$_3$ (100 mL). The reaction mixture was extracted with EtOAc (2×200 mL). The combined organic extracts were washed with brine (150 mL), dried, filtered and concentrated in vacuo. The residue obtained was purified by flash column chromatography (silica gel, chloroform/methanol, 1:0 to 20:1) to give 88d (1.42 g, 71%) as a brown solid. $^1$H NMR (300 MHz, DMSO-d$_6$): 11.17 (s, 1H), 10.55 (s, 1H), 7.72 (s, 1H), 7.40-7.20 (m, 15H), 6.11 (s, 1H), 5.41 (s, 1H), 4.70-4.52 (m, 6H), 4.18-4.10 (m, 1H), 3.96 (d, J=7.7 Hz, 1H), 3.77-3.60 (m, 2H), 1.12 (s, 3H); MS (ES$^+$): 592.1.

Scheme 89 for the Synthesis of Example 4

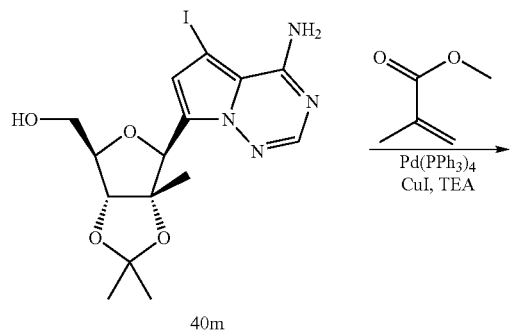

40m

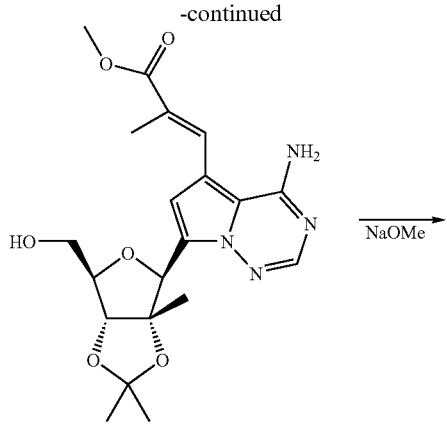

89a

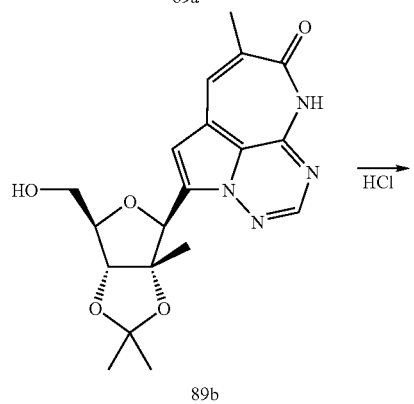

89b

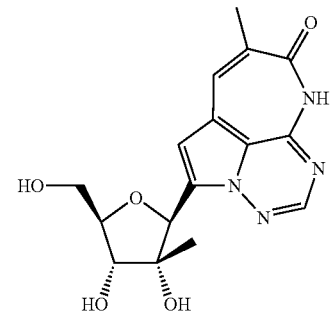

89c

Example 4

Synthesis of 89c

To a solution of tricyclic product 89b (0.165 g, 0.43 mmol) in methanol (5 mL) was added aqueous 1 N HCl (5 mL) and stirred at room temperature overnight. The reaction mixture was concentrated in vacuo to dryness. The residue obtained was purified by flash column chromatography (silica gel 12 g, eluting with 0-100% CMA 80 in chloroform) to give 89c (0.014 g, 9%) as a yellow solid; mp 169° C. $^1$H NMR (300 MHz, DMSO-d$_6$) δ 8.00-7.91 (m, 1H), 7.23-7.15 (m, 1H), 6.91-6.85 (m, 1H), 5.32-5.27 (m, 1H), 5.03-4.93 (m, 1H), 4.86-4.79 (m, 2H), 3.89-3.70 (m, 3H), 3.65-3.55 (m, 2H), 2.00-1.93 (m, 3H), 0.87-0.79 (m, 3H); MS (ES$^-$) 344.8.

The intermediate 89b was prepared as follows:

a. To a solution of 40m, (2 g, 4.5 mmol) in DMF (20 mL) was added copper iodide (17 mg, 0.9 mmol), methyl methacrylate (9.5 ml, 90 mmol), triethylamine (1.25 mL, 9 mmol) and tetrakis(triphenylphosphine)Palladium (0.5 g, 0.45 mmol) and heated with stirring at 70° C. for 68 h. The reaction was diluted with water (60 mL) and extracted with ethyl acetate (3×25 mL). The organic layers were combined washed with water (25 mL), brine (25 mL), dried, filtered, and concentrated in vacuo to dryness. The residue obtained was purified by flash column chromatography (silica gel 40 g, eluting with 0-100% [9:1] of EtOAc:MeOH in hexane) to give 89a (0.615 g, 33%) as a brown solid. $^1$H NMR (300 MHz, DMSO-$d_6$) δ 7.93 (s, 1H), 7.84 (s, 1H), 7.35 (s, 2H), 6.86 (s, 1H), 5.56 (s, 1H), 5.00 (t, J=5.8 Hz, 1H), 4.39 (d, J=2.4 Hz, 1H), 4.10-4.00 (m, 1H), 3.73 (d, J=4.6 Hz, 3H), 3.59 (t, J=5.4 Hz, 2H), 2.07 (d, J=1.2 Hz, 3H), 1.56 (s, 3H), 1.34 (s, 3H), 1.14 (s, 3H).

b. To a freshly prepared solution of sodium methoxide (1.57 mL, 0.1 M) in methanol (14 mL) was added 89a (0.657 g, 1.57 mmol) and heated with stirring at reflux temperature overnight. The reaction mixture was neutralized with glacial acetic acid (0.3 mL) and concentrated in vacuo to dryness. The residue obtained was purified by flash column chromatography (silica gel 12 g, eluting with 0-100% [9:1] of EtOAc:MeOH in hexane) to give 89b (0.165 g, 27%) as a yellow solid.

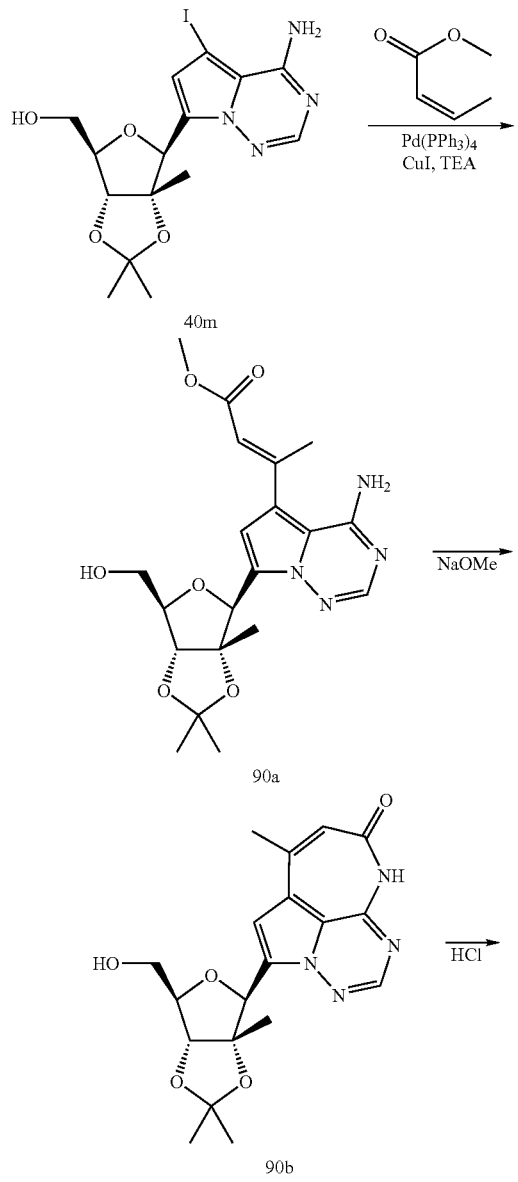

Scheme 90 for the Synthesis of Example 5

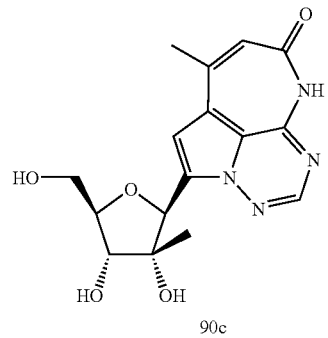

90c

Example 5

Synthesis of 90c

To a solution of 90b (0.050 g, 0.13 mmol) in methanol (0.5 mL) was added aqueous 1 N HCl (0.5 mL) and stirred at room temperature for 48 h. The reaction mixture was concentrated in vacuo to dryness. The solid obtained was triturated with ether, collected by filtration, washed with ether and dried in vacuo at acetone reflux temperature to furnish 90c (0.008 g, 18%) as an off white solid; mp 234° C. $^1$H NMR (300 MHz, DMSO-$d_6$) δ 11.33-10.90 (m, 1H), 8.05 (s, 1H), 7.13 (s, 1H), 5.80 (d, J=1.2 Hz, 1H), 5.34 (s, 1H), 4.99 (s, 3H), 3.83-3.70 (m, 3H), 3.61 (dd, J=4.2, 12.5 Hz, 1H), 2.20 (d, J=1.1 Hz, 3H), 0.84 (s, 3H); MS (ES$^-$) 344.9.

Intermediate 90b was prepared as follows:

a. To a solution of 40m (1.3 g, 3 mmol) in DMF (25 mL) was added copper iodide (110 mg, 0.6 mmol), methyl crotonate (6.36 ml, 60 mmol), triethylamine (0.84 mL, 6 mmol) and tetrakis(triphenylphosphine) palladium (0.350 g, 0.3 mmol) and heated at 70° C. for 48 h. The reaction was diluted with water (75 mL) and extracted with ethyl acetate (2×25 mL). The organic layers were combined, washed with water (2×25 mL), brine (25 mL), dried, filtered, and concentrated in vacuo to dryness. The residue obtained was purified by flash column chromatography (silica gel 40 g, eluting with 0-100% [9:1] of EtOAc:MeOH in hexane) to give 90a (0.565 g, 46%). $^1$H NMR (300 MHz, DMSO-$d_6$) δ 7.95 (d, J=2.8 Hz, 2H), 6.87 (s, 1H), 5.78 (d, J=1.3 Hz, 1H), 5.56 (s, 1H), 4.98 (t, J=5.8 Hz, 1H), 4.39 (d, J=2.5 Hz, 1H), 4.07-3.98 (m, 1H), 3.65 (s, 3H), 3.59 (t, J=5.4 Hz, 2H), 3.33 (s, 1H), 2.55 (d, J=1.1 Hz, 3H), 1.56 (s, 3H), 1.34 (s, 3H), 1.15 (s, 3H).

b. To a freshly prepared solution of sodium methoxide (0.67 mL, 0.1 M) in methanol (6 mL) was added 90a (0.280 g, 0.67 mmol) and heated with stirring at reflux overnight. The reaction mixture was concentrated in vacuo and the residue obtained was purified by flash column chromatography (silica gel 4 g, eluting with 0-100% CMA 80 in chloroform) to give 90b (0.100 g, 39%) as a yellow solid; mp 152° C. $^1$H NMR (300 MHz, DMSO-$d_6$) δ 11.14 (s, 1H), 8.06 (s, 1H), 6.97 (s, 1H), 5.82 (s, 1H), 5.47 (s, 1H), 5.01 (t, J=5.9 Hz, 1H), 4.41 (d, J=2.5 Hz, 1H), 4.11-4.01 (m, 1H), 3.62 (t, J=5.3 Hz, 2H), 2.22 (d, J=1.1 Hz, 3H), 1.56 (s, 3H), 1.34 (s, 3H), 1.12 (s, 3H); MS (ES$^-$) 384.9.

Scheme 91 for the Synthesis of Example 6

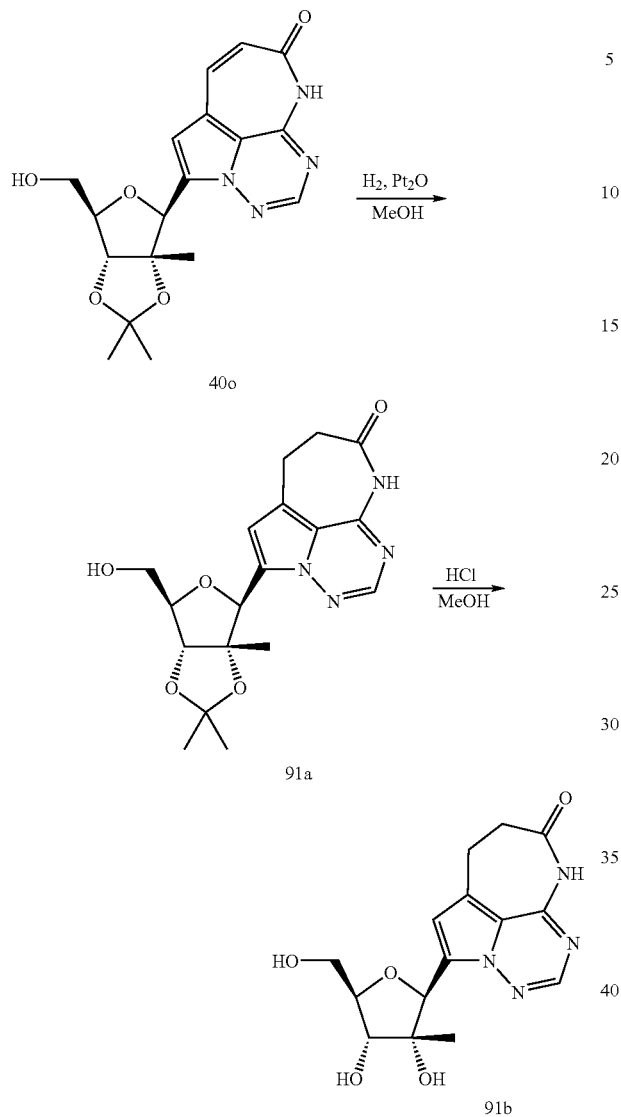

Example 6

Synthesis of 91b

To a solution of tricyclic product 91a (20 mg, 0.05 mmol) in methanol (0.5 mL) was added aqueous 1 N HCl (0.5 mL) and stirred at room temperature overnight. The reaction mixture was concentrated in vacuo to dryness to furnish 91b (19 mg, 100%) as a white solid; mp 59-64° C. $^1$H NMR (300 MHz, DMSO-$d_6$) δ 8.73-8.30 (m, 2H), 8.02 (s, 1H), 6.79 (s, 1H), 5.32 (s, 1H), 4.06-3.84 (m, 3H), 3.75 (d, J=11.7 Hz, 3H), 3.63 (d, J=8.8 Hz, 2H), 3.14 (d, J=7.3 Hz, 2H), 0.77 (s, 3H); MS (ES$^-$) 332.9.

Intermediate 91a was prepared as follows.

To a solution of tricyclic product 40o (100 mg, 0.27 mmol) in methanol (100 mL) was added platinum oxide (50 mg) and hydrogenated at 50 psi for 3 days. The catalyst was removed by filtration through a pad of Celite and the filtrate concentrated in vacuo to give crude product. The crude residue was purified by flash column chromatography (silica gel 4 g, eluting with CHCl$_3$/CMA-80, 0-100%) to furnish crude 91a (64 mgs). The crude material was recrystallized from methanol (2 mL) to furnish pure 91a (25 mg, 25%) as a white solid. $^1$H NMR (300 MHz, DMSO-$d_6$) δ 11.02 (s, 1H), 8.17 (s, 1H), 6.78 (s, 1H), 5.58 (s, 1H), 5.00 (s, 1H), 4.40 (s, 1H), 4.05 (s, 1H), 3.58 (s, 2H), 3.02 (s, 2H), 2.91 (s, 2H), 1.56 (s, 3H), 1.34 (s, 3H), 1.14 (s, 3H); MS (ES$^+$) 375.0, (ES$^-$) 373.3.

Scheme 92 for the synthesis Example 7

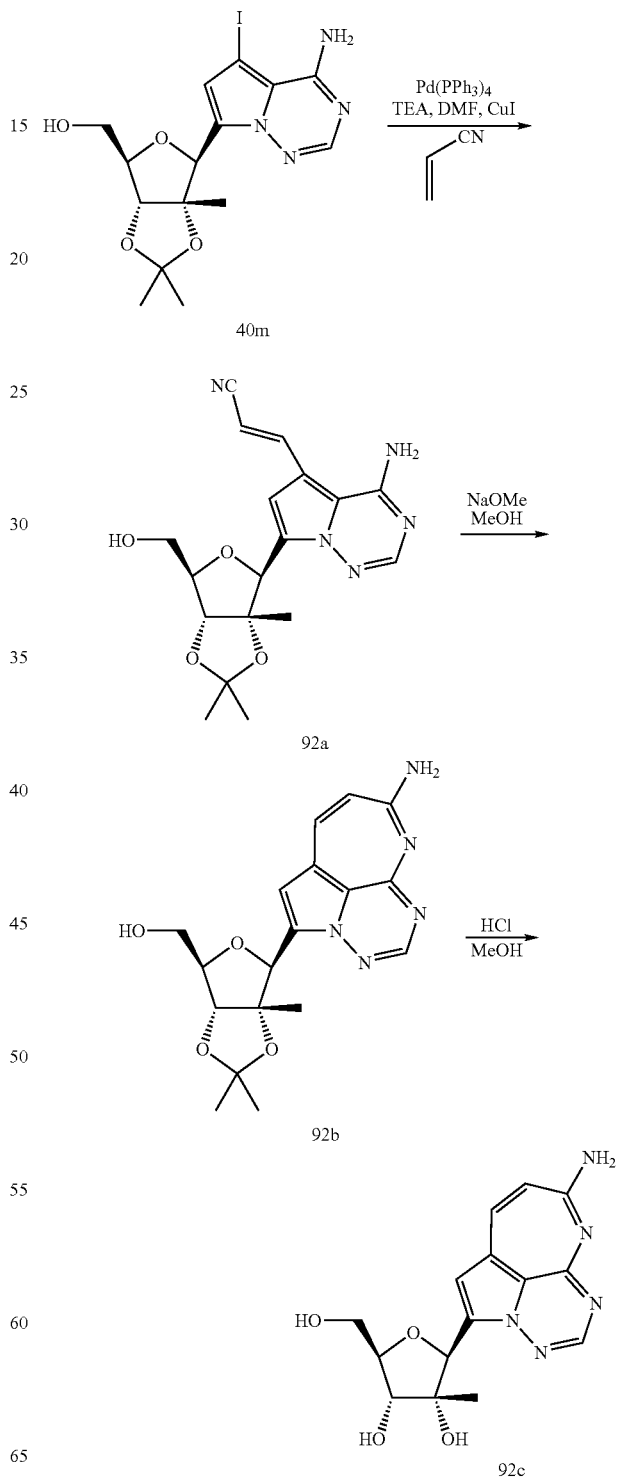

Example 7

Synthesis of 92c

To a solution of tricyclic product 92b (220 mg, 0.59 mmol) in methanol (4 mL) was added aqueous 1 N HCl (4 mL) and stirred at room temperature overnight. The reaction mixture was concentrated in vacuo to dryness. The residue obtained was triturated with ether and the solid obtained was collected by filtration, washed with ether and dried in vacuo at acetone reflux temperature to furnish 92c (145 mg, 74%) as a mustard solid; mp 152-159° C. $^1$H NMR (300 MHz, DMSO-$d_6$) δ 12.60 (s, 1H), 9.76 (s, 1H), 9.27 (s, 1H), 8.02 (s, 1H), 7.55 (d, J=11.6 Hz, 1H), 7.13 (s, 1H), 6.39 (d, J=11.6 Hz, 1H), 5.23 (s, 1H), 4.99-4.20 (m, 3H), 3.77 (d, J=10.1 Hz, 2H), 3.70-3.57 (m, 2H), 0.87 (s, 3H); MS (ES$^+$) 332.0, (ES$^-$) 329.9.

Intermediate 92b was prepared as follows.

a. To a solution of 40m (2.23 g, 4.99 mmol) in DMF (70 mL) was added copper iodide (380 mg, 1.99 mmol), triethylamine (3 mL, 21.8 mmol) and tetrakis(triphenylphosphine) palladium (1.15 g, 1 mmol). To the suspension was added acrylonitrile (14.3 ml, 217 mmol) in 4 portions over a period of 3 h and heated with stirring at 70° C. for 3 days. The reaction was diluted with water (210 mL) and extracted with ethyl acetate (3×70 mL). The organic layers were combined, washed with water (70 mL), brine (70 mL) dried, filtered, and concentrated in vacuo to dryness. The residue obtained was purified by flash column chromatography (silica gel, 110 g, eluting with 0-100% [9:1] of EtOAc:MeOH in hexane) to give 92a (619 mg, 33%) as a mustard-colored solid; mp 238° C. $^1$H NMR (300 MHz, DMSO-$d_6$) δ 8.15 (d, J=15.9 Hz, 1H), 7.74 (s, 2H), 7.42 (s, 1H), 7.20 (s, 1H), 6.19 (d, J=15.7 Hz, 1H), 5.51 (s, 1H), 4.96 (t, J=5.8 Hz, 1H), 4.39 (d, J=2.4 Hz, 1H), 4.03 (d, J=2.4 Hz, 1H), 3.66-3.55 (m, 2H), 1.55 (s, 3H), 1.33 (s, 3H), 1.12 (s, 3H); IR (KBr) 2209 cm$^{-1}$; MS (ES$^-$) 370.1.8.

To a freshly prepared solution of sodium methoxide (36 mg sodium in 1.6 ml methanol, 0.1 M) was added 92a (0.58 g, 1.56 mmol) and heated with stirring at reflux for 4 h and then at room temperature overnight. The reaction mixture was neutralized with glacial acetic acid (0.094 mL) and concentrated in vacuo to dryness. The residue obtained was purified by flash column chromatography (silica gel 12 g, eluting with CHCl$_3$/CMA-80, 0-100%) to furnish 92b (265 mg, 44%) as a rust solid; mp 112-114° C. $^1$H NMR (300 MHz, DMSO-$d_6$) δ 8.05 (s, 1H), 7.96 (s, 1H), 7.68 (s, 1H), 6.99 (d, J=11.4 Hz, 1H), 6.60 (s, 1H), 5.73 (d, J=11.5 Hz, 1H), 5.34 (s, 1H), 4.98 (t, J=5.7 Hz, 1H), 4.37 (d, J=2.4 Hz, 1H), 4.03-3.98 (m, 1H), 3.64-3.48 (m, 2H), 1.52 (s, 3H), 1.33 (s, 3H), 1.12 (s, 3H); MS (ES$^+$) 372.1, (ES$^-$) 369.9.

Scheme 93 for the Synthesis of Example 8

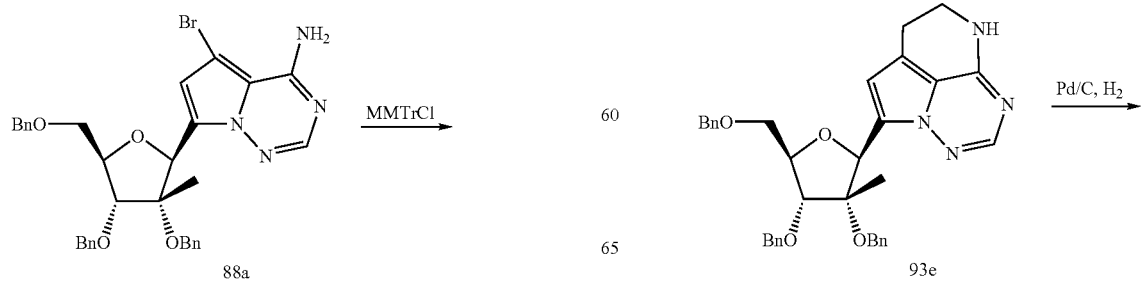

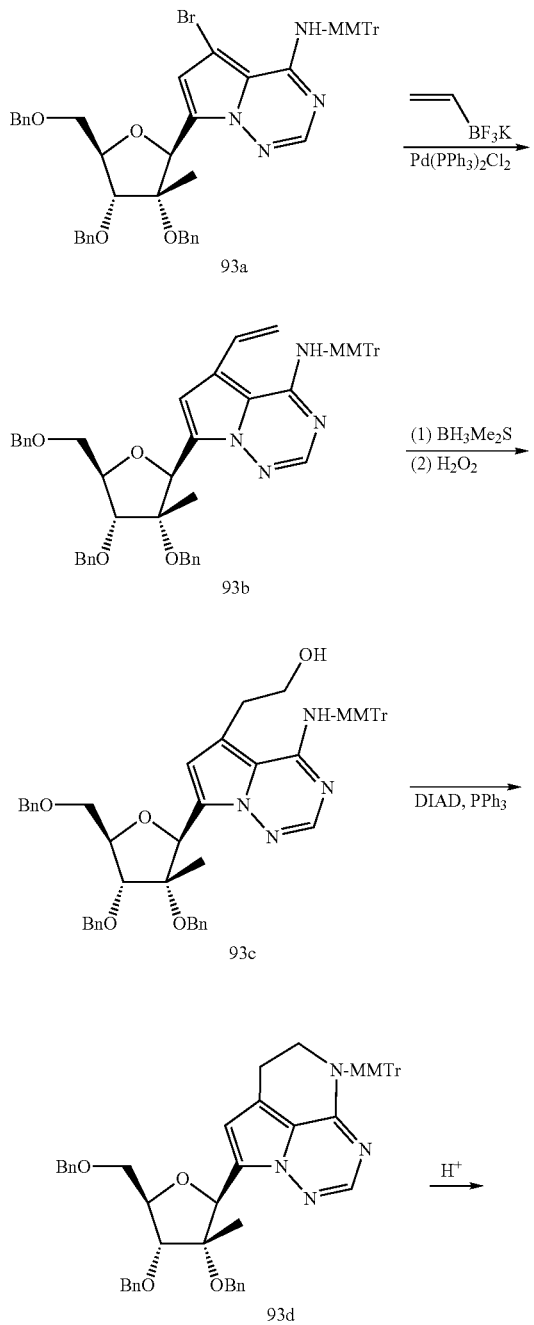

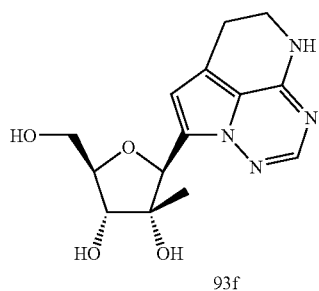

93f

Example 8

Synthesis of 93f

To a suspension of 93e (310 mg, 0.54 mmol) in MeOH was added 1N aqueous HCl (1.8 mL) Pd/C (10%, 100 mg) and hydrogenated at 60 psi for 25 h. The reaction mixture was filtered and the filtrate was concentrated in vacuo. The residue obtained was purified by flash column chromatography (silica gel, 30 g, eluting with chloroform/CMA80, 1:0 to 1:1) to furnish 93f (137 mg, 83%) as a white solid; mp: 254.2° C. $^1$H NMR (300 MHz, DMSO-d$_6$) δ 7.96 (s, 1H), 7.78 (s, 1H), 6.50 (s, 1H), 5.28 (s, 1H), 4.92 (d, J=6.7 Hz, 1H), 4.76 (t, J=5.4 Hz, 1H), 4.71 (s, 1H), 3.80-3.67 (m, 3H), 3.65-3.50 (m, 3H), 2.95-2.85 (m, 2H), 0.83 (s, 3H); MS (ES$^+$): 307.1.

Intermediate 93e was prepared as follows.

a. To a solution of 42a (27.85 g, 44.23 mmol) in pyridine (400 mL) was added 4-methoxytriphenylmethyl chloride (56.74 g, 178.24 mmol) and heated with stirring at 70° C. for 16 h. The reaction mixture was diluted with EtOAc (1.5 L), washed with water (2×700 mL) and brine (500 mL), dried, filtered, and concentrated. The residue was purified by flash column chromatography (silica gel eluting with hexanes/EtOAc, 1:0 to 4:1) to give 93a (28.38 g, 71%,) as a light yellow solid; mp 78.6° C. $^1$H NMR (300 MHz, DMSO-d$_6$): δ 7.91 (s, 1H), 7.63 (s, 1H), 7.45-7.12 (m, 27H), 6.96 (s, 1H), 6.87 (d, J=8.9 Hz, 2H), 5.56 (s, 1H), 4.74-4.50 (m, 6H), 4.20-4.12 (m, 1H), 4.02 (d, J=8.5 Hz, 1H), 3.87-3.64 (m, 2H), 3.71 (s, 3H), 1.05 (s, 3H).

b. To a solution of 93a, (26.1 g, 28.94 mmol) in DME (500 mL) was added potassium vinyltrifluoroborate (7.2 g, 53.75 mmol), NaHCO$_3$ (7.2 g, 85.70 mmol), Pd(PPh$_3$)$_2$Cl$_2$ (1.4 g, 98%, 1.99 mmol), H$_2$O (65 mL) and refluxed for 6 h. The reaction mixture was diluted with water (500 mL) and extracted with EtOAc (1.8 L and 0.5 L). The organic layers were combined and washed with brine (500 mL), dried, filtered, and concentrated in vacuo. The residue was purified by flash column chromatography (silica gel eluting with hexanes/EtOAc, 1:0 to 6:1) to furnish 93b (18.3 g, 74%) as a light yellow solid; mp 79.7° C. $^1$H NMR (300 MHz, DMSO-d$_6$) δ 7.56 (s, 1H), 7.44-7.12 (m, 28H), 7.01 (dd, J=17.2, 11.0 Hz, 1H), 6.93 (s, 1H), 6.84 (d, J=8.8 Hz, 2H), 5.57 (s, 1H), 5.31 (d, J=17.2 Hz, 1H), 5.16 (d, J=11.0 Hz, 1H), 4.76-4.52 (m, 6H), 4.22-4.13 (m, 1H), 4.04 (d, J=8.4 Hz, 1H), 3.88-3.70 (m, 2H), 3.71 (s, 3H), 1.05 (s, 3H); MS (ES$^-$): 847.6.

c. To a cold (ice water bath) solution of 93b (20.5 g, 24.15 mmol) in THF (90 mL) was added dropwise borane dimethyl sulfide solution (2M in THF, 9.5 mL) and stirred at room temperature for 4 h. The reaction mixture was quenched with ethanol (19 mL), aqueous 3N NaOH (6.0 mL), and cooled with ice/water. To the cold reaction mixture was added hydrogen peroxide (30% in water, 6 mL) and heated at reflux for 1 h. The reaction mixture was cooled to room temperature, diluted with ethyl acetate (1 L), washed with water (2×500 mL), brine (300 ml), dried and concentrated in vacuo. The residue obtained was purified by flash column chromatography (silica gel, eluting with ethyl acetate in hexane 1:0 to 2:1) to give 93c (11.17 g, 53%) as a yellow solid. $^1$H NMR (300 MHz, DMSO-d$_6$) δ 8.95 (s, 1H), 7.45 (s, 1H), 7.42-7.22 (m, 27H), 6.81 (d, J=9.0 Hz, 2H), 6.62 (s, 1H), 5.57 (s, 1H), 5.51 (t, J=3.7 Hz, 1H), 4.76-4.48 (m, 6H), 4.20-4.10 (m, 1H), 4.04 (d, J=8.4 Hz, 1H), 3.91-3.66 (m, 2H), 3.71 (s, 3H), 3.58-3.46 (m, 2H), 2.97-2.86 (s, 2H), 1.03 (s, 3H).

d. To a solution of 93c (1.0 g, 1.15 mmol) and triphenylphosphine (610 mg, 2.30 mmol) in 1,4-dioxane (15 mL) was added dropwise a solution of DIAD (0.5 mL, 95%, 2.41 mmol) in 1,4-dioxane (2.5 mL) and stirred at room temperature for 16 h. The reaction mixture was concentrated in vacuo and the residue obtained was purified by flash column chromatography (silica gel 50 g, eluting with ethyl acetate in hexane 1:0 to 4:1) to give 93d (730 mg, 75%) as a white solid. $^1$H NMR (300 MHz, DMSO-d$_6$): δ 7.68 (s, 1H), 7.49-7.15 (m, 27H), 6.86 (d, J=9.0 Hz, 2H), 6.59 (s, 1H), 5.53 (s, 1H), 4.80-4.45 (m, 6H), 4.22-4.10 (m, 1H), 4.02 (d, J=7.9 Hz, 1H), 3.86-3.64 (m, 2H), 3.72 (s, 3H), 3.60-3.34 (m, 2H), 3.18-2.92 (m, 2H), 1.08 (s, 3H); MS (ES$^+$): 671.1 (M+Na).

e. To a solution of 93d (618 mg, 0.73 mmol) in acetonitrile (35 mL) was added aqueous 1N HCl (3.5 mL) and stirred at room temperature for 17 h. The reaction mixture was neutralized with aqueous 0.5 N NaOH, diluted with water (50 mL), and concentrated in vacuo to remove acetonitrile. The aqueous layer was extracted with CHCl$_3$/MeOH (5:1, 100 mL and 50 mL). The combined organic extracts were dried, filtered and concentrated in vacuo. The residue obtained was purified by flash column chromatography (silica gel 30 g, eluting with hexane/ethyl acetate/methanol, 1:1:0 to 1:1:0.1) to give 93e (362 mg, 86%) as a white solid. $^1$H NMR (300 MHz, DMSO-d$_6$) δ 8.01 (s, 1H), 7.81 (s, 1H), 7.41-7.27 (m, 15H), 6.53 (s, 1H), 5.55 (s, 1H), 4.77-4.49 (m, 6H), 4.26-4.12 (m, 1H), 4.04 (d, J=8.1 Hz, 1H), 3.85-3.65 (m, 2H), 3.60-3.48 (m, 2H), 2.83 (t, J=6.5 Hz, 2H), 1.10 (s, 3H); MS (ES$^+$): 577.1.

Scheme 94 for the Synthesis of Example 9

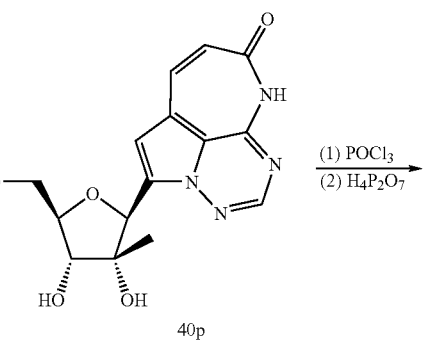

40p

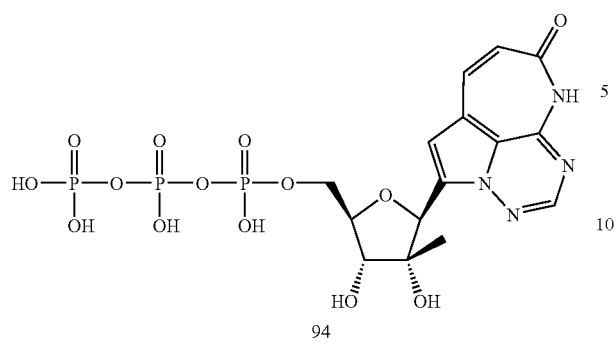

94

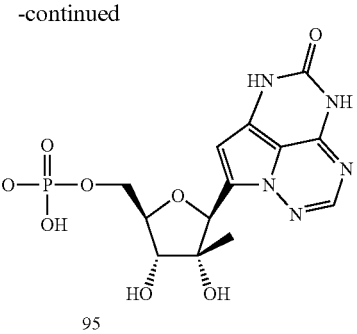

95

Example 9

Synthesis of 94

To a suspension of 40p (33 mg, 0.1 mmol) in trimethylphosphate (1 mL) at 0° C. was added phosphorus oxychloride (19 µL, 0.21 mmol) and stirred at 0° C. for 1 h. The reaction mixture was treated with n-tributylamine (70 µL, 0.29 mmol), acetonitrile (100 µL), tributylammonium pyrophosphate (H$_4$P$_2$O$_7$.1.6 n-Bu$_3$N, 190 mg, 0.40 mmol) and stirred at room temperature for 0.5 h. The reaction mixture was quenched with 1M TEAB buffer (5 mL, pre-cooled with ice/water, pH=8.0), diluted with water (20 mL), and washed with dichloromethane (2×15 mL). The aqueous solution was concentrated in vacuo to remove traces of CH$_2$Cl$_2$ and purified by DEAE ion exchange column chromatography with a linear gradient of TEAB buffer (1M TEAB buffer, pH=8.0/H$_2$O, 0:1 to 1:0, total volume: 500 mL). The fractions containing the desired triphosphate were combined and concentrated. The residue was re-dissolved in H$_2$O and purified by HPLC(CH$_3$CN/0.1 M TEAB buffer, pH=8.0, 0-30 min; 0-35% CH$_3$CN; monitoring at 238 nM) to give 94 (t$_R$=18.7 min). Fractions containing 94 were concentrated and re-dissolved in 2 mL of H$_2$O and the concentration of 94 was measured to be 0.34 mM (yield: 0.7%) by UV (240 nm, ε=58,000 M$^{-1}$cm$^{-1}$). $^1$H NMR (300 MHz, D$_2$O) δ 7.79 (s, 1H), 7.19 (d, J=12.0 Hz, 1H), 7.02 (s, 1H), 5.78 (d, J=12.0 Hz, 1H), 5.46 (s, 1H), 4.04 (s, 2H), 4.50-3.50 (m, 2H), 0.91 (s, 3H). $^{31}$P NMR (121 MHz, D$_2$O): δ −8.8 (1P), −11.0 (1P), −22.3 (1P). MS (ES$^-$): 570.9 (M-1).

Scheme 95 for the Synthesis of Example 10

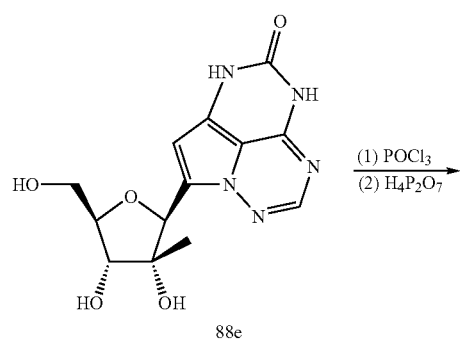

88e

Example 10

Synthesis of 95

To a suspension of 95e (64 mg, 0.2 mmol) in trimethylphosphate (2 mL) at 0° C. was added phosphorus oxychloride (37 µL, 0.4 mmol) and stirred at 0° C. for 1 h. The reaction mixture was treated with n-tributylamine (150 µL, 0.62 mmol), acetonitrile (200 µL), tributylammonium pyrophosphate (H$_4$P$_2$O$_7$.1.6 n-Bu$_3$N, 380 mg, 0.8 mmol) and stirred at room temperature for 0.5 h. The reaction mixture was quenched with 1M TEAB buffer (10 mL, pre-cooled with ice water, pH=8.0), diluted with water (20 mL), and washed with dichloromethane (2×15 mL). The aqueous phase was concentrated in vacuo to remove the trace of CH$_2$Cl$_2$ and purified by DEAE ion exchange column chromatography with a linear gradient of TEAB buffer (1M TEAB buffer, pH=8.0/H$_2$O, 0:1 to 1:0, total: 500 mL). The fractions containing the desired triphosphate were combined and concentrated. The residue was re-dissolved in H$_2$O and purified by HPLC(CH$_3$CN/0.1 M TEAB buffer, pH=8.0, 0-40 min, 0-35% CH$_3$CN; monitoring at 244 nm) to give 95 (t$_R$=17.2 min). Fractions containing 95 were concentrated and re-dissolved in 2 mL of H$_2$O and the concentration of 95 was measured to be 9.8 mM (yield: 10%) by UV (280 nm, ε=6,400 M$^{-1}$cm$^{-1}$). $^1$H NMR (300 MHz, D$_2$O) δ 7.53 (s, 1H), 6.40 (s, 1H), 5.31 (s, 1H), 4.32-4.00 (m, 4H), 0.93 (s, 3H); $^{31}$P NMR (D$_2$O) 6-10.69 (d, J=19.4 Hz, IP), −11.26 (d, J=20.6 Hz, IP), −23.24 (t, J=19.4 Hz, IP). MS (ES$^-$): 560.1 (M-1).

Example 11

The following illustrate representative pharmaceutical dosage forms, containing a compound of Formula I, or a pharmaceutically acceptable salt or prodrug thereof ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |

-continued

| | |
|---|---|
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. A compound of formula I:

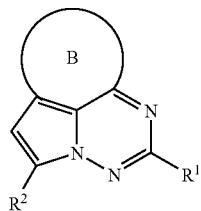

I wherein;
B represents a 5, 6, 7 or 8 membered carbocyclic or heterocyclic ring comprising one or more double bonds, wherein B is optionally substituted with one or more oxo, thioxo, $NR_cR_d$, F, Cl, Br, I, $OR_z$, $SR_z$, alkyl, C≡N, C≡C—R, $N_3$ or $SO_2R'$;

wherein:
R is H, alkyl or aryl;
R' is OH, $NH_2$ or alkyl;
$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;
$R^2$ is a nucleoside sugar group;
$W^3$ is absent, alkyl, or H;
$R_a$ and $R_b$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl, amino, substituted amino, and NO; or $R_a$ and $R_b$ together with the nitrogen to which they are attached form a pyrrolidino, piperidino, piperazino, azetidino, morpholino, or thiomorpholino ring;
$R_c$ and $R_d$ are independently selected from the group consisting of H, alkyl, substituted alkyl, alkenyl, substituted alkenyl, alkynyl, substituted alkynyl, cycloalkyl, acyl, substituted acyl and $SO_2$-alkyl; or $R_c$ and $R_d$ together with the nitrogen to which they are attached form a pyrrolidino, piperidino, piperazino, azetidino, morpholino, or thiomorpholino ring; and
each $R_z$ is independently selected from the group consisting of H, alkyl, substituted alkyl, alkenyl, substituted alkenyl, alkynyl, substituted alkynyl, cycloalkyl, acyl and substituted acyl;
or a pharmaceutically acceptable salt or prodrug thereof.

2. The compound of claim 1 wherein the compound of formula I is a compound of formula II:

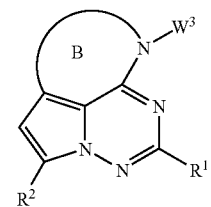

II wherein;
B represents a 5, 6, 7 or 8 membered ring comprising one or more heteroatoms and one or more double bonds, wherein B is optionally substituted with one or more oxo, thioxo, $NR_cR_d$, F, Cl, Br, I, $OR_z$, $SR_z$, alkyl, C≡N, C≡C—R, $N_3$ or $SO_2R'$;

wherein:
R is H, alkyl or aryl;
R' is OH, $NH_2$ or alkyl;
$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;
$R^2$ is a nucleoside sugar group;
$W^3$ is absent, alkyl, or H;
$R_a$ and $R_b$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl, amino, substituted amino, and NO; or $R_a$ and $R_b$ together with the nitrogen to which they are attached form a pyrrolidino, piperidino, piperazino, azetidino, morpholino, or thiomorpholino ring;
$R_c$ and $R_d$ are independently selected from the group consisting of H, alkyl, substituted alkyl, alkenyl, substituted alkenyl, alkynyl, substituted alkynyl, cycloalkyl, acyl, substituted acyl and SO$_2$-alkyl; or R$_c$ and R$_d$ together with the nitrogen to which they are attached form a pyrrolidino, piperidino, piperazino, azetidino, morpholino, or thiomorpholino ring; and each R$_z$ is independently selected from the group consisting of H, alkyl, substituted alkyl, alkenyl, substituted alkenyl, alkynyl, substituted alkynyl, cycloalkyl, acyl and substituted acyl;

or a pharmaceutically acceptable salt or prodrug thereof.

3. The compound of claim 2 wherein W$^3$ is absent or H.

4. A compound of claim 1 which is a compound of formula III:

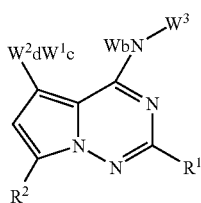

(III)

wherein:
each b, c and d is independently selected from a single and double bond provided that when b is a double bond, c is single bond, when c is a double bond, b and d are single bonds and when d is a double bond c is a single bond; or d is absent when W$^2$ is absent; and W$^2$ and d are not absent, when bNW$^3$ is absent;

W is C=R$_e$, CH$_2$, CR$_g$ or O, provided that when W is C=R$_e$, CH$_2$ or O, b and c are single bonds, or c is a single bond and bNW$^3$ is absent; and provided when W is CR$_g$, one of b or c is a double bond, or bNW$^3$ is absent and c is a double bond;

R$_e$ is O or S;

R$_g$ is H, NR$_c$R$_d$, OR$_z$ or SR$_z$;

W$^1$ is C=R$_h$, CR$_i$R$_{i'}$, N, NR$_n$, CR$_j$ or O provided that when W$^1$ is C=R$_h$, CR$_i$R$_{i'}$, NR$_n$ or O, c and d are single bonds or c is a single bond and W$^2$d is absent; and provided when W$^1$ is CR$_j$ or N one of c or d is a double bond or W2d is absent and c is a double bond;

R$_h$ is O or S;

R$_i$ and R$_{i'}$ are H, CH$_3$, NH$_2$ or Br;

R$_j$ is CH$_3$, NH$_2$, or H;

W is C=R$_k$, (CR$_l$R$_{l'}$)$_{p'}$, CR$_m$, O, NR$_s$, absent or N provided that when W$^2$ is C=R$_k$, CR$_l$R$_{l'}$, O, or NR$_s$d is a single bond; when W$^2$ is N or CR$_m$d is a double bond; and provided when W$^2$ is absent, d is absent;

R$_k$ is O or S;

R$_l$ and R$_{l'}$ are H, CH$_3$, OCH$_3$, NH$_2$ or SCH$_3$;

p' is 1 or 2;

R$_m$ is H, NR$_c$R$_d$, F, Cl, Br, I, OR$_z$, SR$_z$, alkyl, C≡N, C≡C—R, N$_3$ or SO$_2$R';

R$_n$ is H, alkyl, or NR$_q$R$_r$ wherein each R$_q$ and R$_r$ is H or alkyl;

R$_s$ is H, CH$_3$, or NH$_2$; and

W$^3$ is absent, H or alkyl; provided that when W$^3$ is absent b is a double bond;

or a pharmaceutically acceptable salt or prodrug thereof.

5. A compound of claim 1 which is a compound of formula IV:

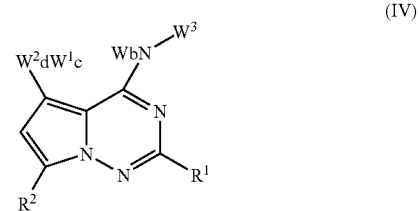

(IV)

wherein:
each b, c and d is independently selected from a single or double bond provided that when b is a double bond, c is single bond, when c is a double bond, b and d are single bonds and when d is a double bond c is a single bond; or d is absent when W$^2$ is absent;

W is C=R$_e$, CR$_f$R$_f$, CR$_g$ or O, provided that when W is C=R$_e$, CR$_f$R$_f$ or O, b and c are single bonds and when W is CR$_g$, one of b or c is a double bond;

R$_e$ is O or S;

R$_f$ is H;

R$_g$ is H, NR$_c$R$_d$, OR$_z$ or SR$_z$;

W$^1$ is C=R$_h$, CR$_i$R$_{i'}$, NH, CR$_j$ or O provided that when W$^1$ is C=R$_h$, CR$_i$R$_{i'}$, or O, c and d are single bonds; when W$^1$ is CR$_j$, one of c or d is a double bond; and when W$^1$ is NH, W is not O and W$^2$ is not O, NH, or N;

R$_h$ is O or S;

R$_i$ and R$_{i'}$ are H, CH$_3$ or Br;

R$_j$ is CH$_3$ or H;

W$^2$ is C=R$_k$, (CR$_l$R$_{l'}$)$_{p'}$, CR$_m$, O, NH, absent, or N provided that when W$^2$ is C=R$_k$, CR$_l$R$_{l'}$, CR$_m$, O, or NHd is a single bond; when W$^2$ is N or CR$_m$d is a double bond; or when W$^2$ is absent, d is absent;

R$_k$ is O or S;

R$_l$ and R$_{l'}$ are H, CH$_3$, OCH$_3$ or SCH$_3$;

p' is 1 or 2;

R$_m$ is H, NR$_c$R$_d$, F, Cl, Br, I, OR$_z$, SR$_z$, alkyl, C≡N, C≡C—R, N$_3$ or SO$_2$R'; and W$^3$ is absent, H or alkyl; provided that when W$^3$ is absent b is a double bond;

or a pharmaceutically acceptable salt or prodrug thereof.

6. The compound of formula IV as described in claim 5 wherein:

each b, c and d is independently selected from a single or double bond provided that when b is a double bond, c is single bond, when c is a double bond, b and d are single bonds and when d is a double bond c is a single bond;

W is C=R$_e$, CR$_f$R$_f$, CR$_g$ or O, provided that when W is C=R$_e$, CR$_f$R$_f$ or O, b and c are single bonds and when W is CR$_g$, one of b or c is a double bond;

R$_e$ is O or S;

R$_f$ is H;

R$_g$ is H, NR$_c$R$_d$, OR$_z$ or SR$_z$;

W$^1$ is C=R$_h$, CR$_i$R$_{i'}$, CR$_j$ or O provided that when W$^1$ is C=R$_h$, CR$_i$R$_{i'}$, or O, c and d are single bonds and when W$^1$ is CR$_j$, one of c or d is a double bond;

R$_h$ is O or S;

R$_i$ and R$_{i'}$ are H, CH$_3$ or Br;

R$_j$ is CH$_3$ or H;

W$^2$ is C=R$_k$, (CR$_l$R$_{l'}$)$_{p'}$, CR$_m$, O, NH or N provided that when W$^2$ is C=R$_k$, CR$_l$R$_{l'}$, CR$_m$, O, or NHd is a single bond and when W$^2$ is N or CR$_m$d is a double bond;

R$_k$ is O or S;

$R_l$ and $R_{l'}$ are H, $CH_3$, $OCH_3$ or $SCH_3$;

p' is 1 or 2;

$R_m$ is H, $NR_cR_d$, F, Cl, Br, I, $OR_z$, $SR_z$, alkyl, C≡N, C≡C—R, $N_3$ or $SO_2R'$; and $W^3$ is absent or H, provided that when $W^3$ is absent b is a double bond;

or a pharmaceutically acceptable salt or prodrug thereof.

7. The compound of claim 1 wherein the compound of formula I is a compound of formula V:

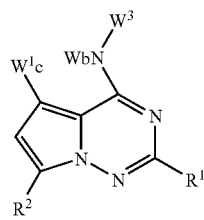

(V)

wherein:

each of b and c is independently selected from a single or double bond provided that when b is a double bond, c is single bond and when c is a double bond b is a single bond;

W is $C=R_e$, $CR_fR_f$, $CR_g$ or O, provided that when W is $C=R_e$, $CR_fR_f$ or O, b and c are single bonds and when W is $CR_g$, one of b or c is a double bond;

$R_e$ is O or S;

$R_f$ is H;

$R_g$ is H, $NR_cR_d$, $OR_z$, or $SR_z$;

$W^1$ is $C=R_h$, $CR_iR_i$, NH, $CR_j$ or O provided that when $W^1$ is $C=R_h$, $CR_iR_i$, or O, c is a single bond; when $W^1$ is $CR_j$, c is a double bond; and when $W^1$ is NH, W is not O;

$R_h$ is O or S;

$R_i$ and $R_{i'}$ are each independently H, $CH_3$ or Br;

$R_j$ is $CH_3$ or H; and $W^3$ is absent, H, or alkyl, provided that when $W^3$ is absent b is a double bond;

or a pharmaceutically acceptable salt or prodrug thereof.

8. A compound of claim 1 which is a compound of formula 1-9:

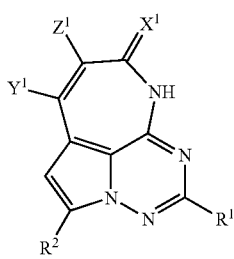

1

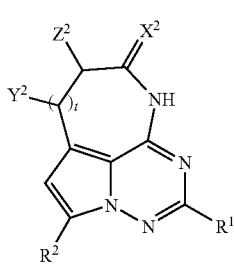

2

-continued

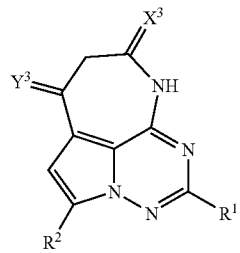

3

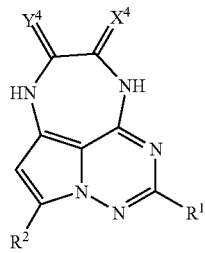

4

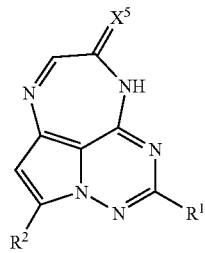

5

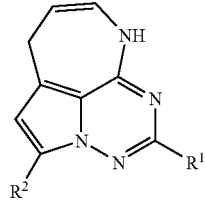

6

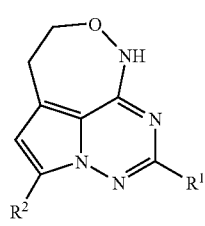

7

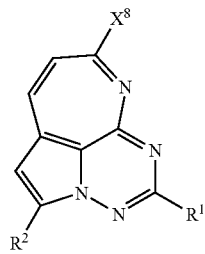

8

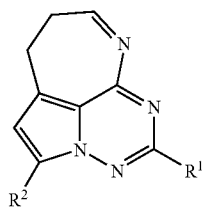

wherein:
X¹ is O, S, or two hydrogens;
X² is O, S, or two hydrogens;
X³ is O or S;
X⁴ is O, S, or two hydrogens;
X⁵ is O, S, or two hydrogens;
X⁸ is H, NH$_2$, OCH$_3$ or SCH$_3$;
Y¹ is H, OH, NH$_2$, NHCH$_3$, N(CH$_3$)$_2$, F, Cl, Br, I, alkoxy, alkyl SCH$_3$, C≡N, C≡C—R, N$_3$ or SO$_2$R';
Y² is H, CH$_3$, OCH$_3$ or SCH$_3$;
Y³ is O or S;
Y⁴ is O, S, or two hydrogens;
Z¹ is H or CH$_3$;
Z² is H, CH$_3$ or Br; and
t is 1 or 2;
or a pharmaceutically acceptable salt or prodrug thereof.

9. The compound of claim 1 wherein R¹ is H or NR$_a$R$_b$.

10. The compound of claim 1 which is selected from,

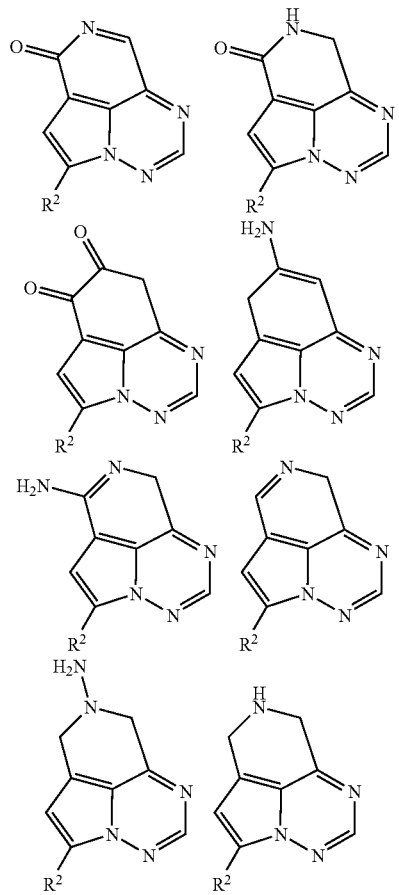

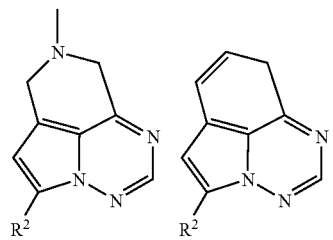

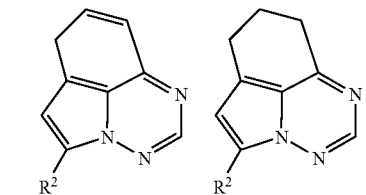

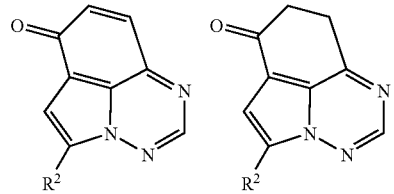

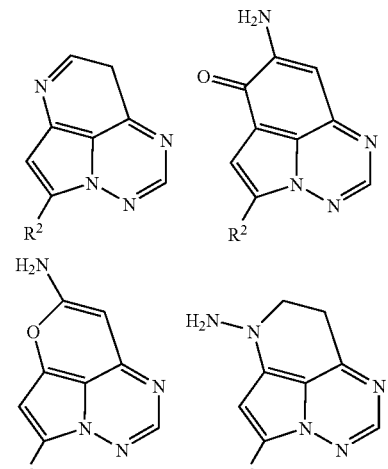

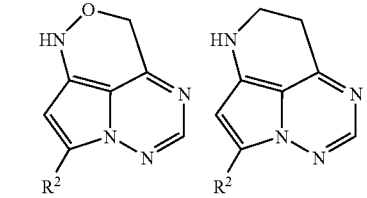

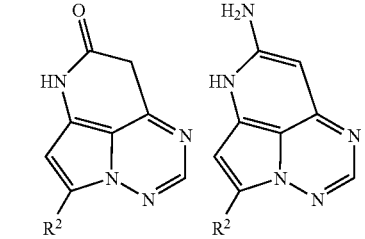

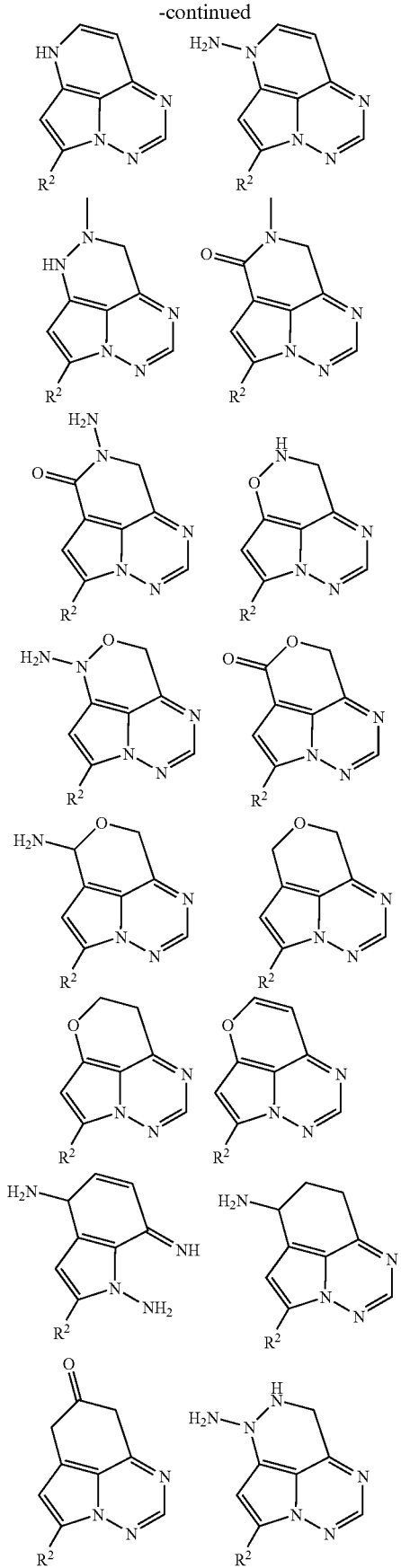
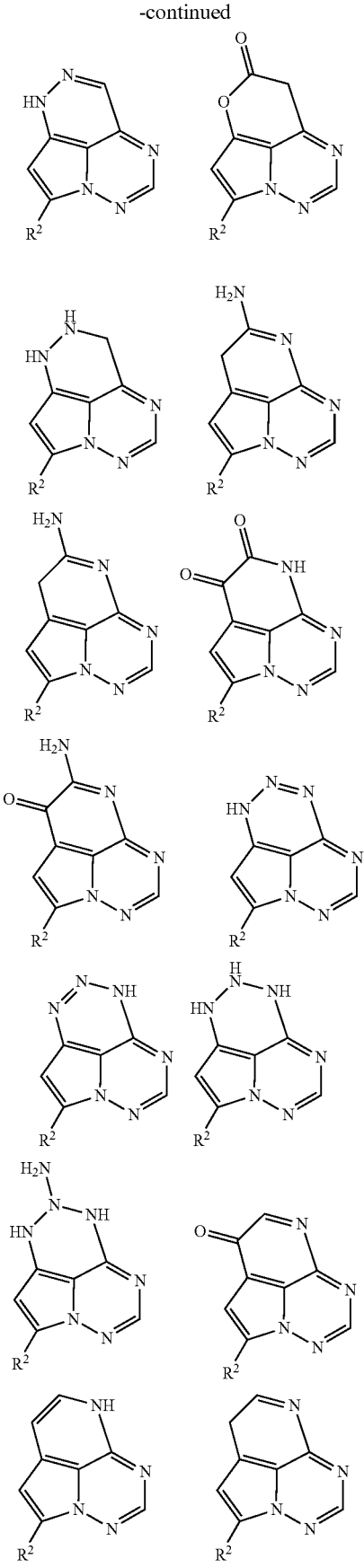

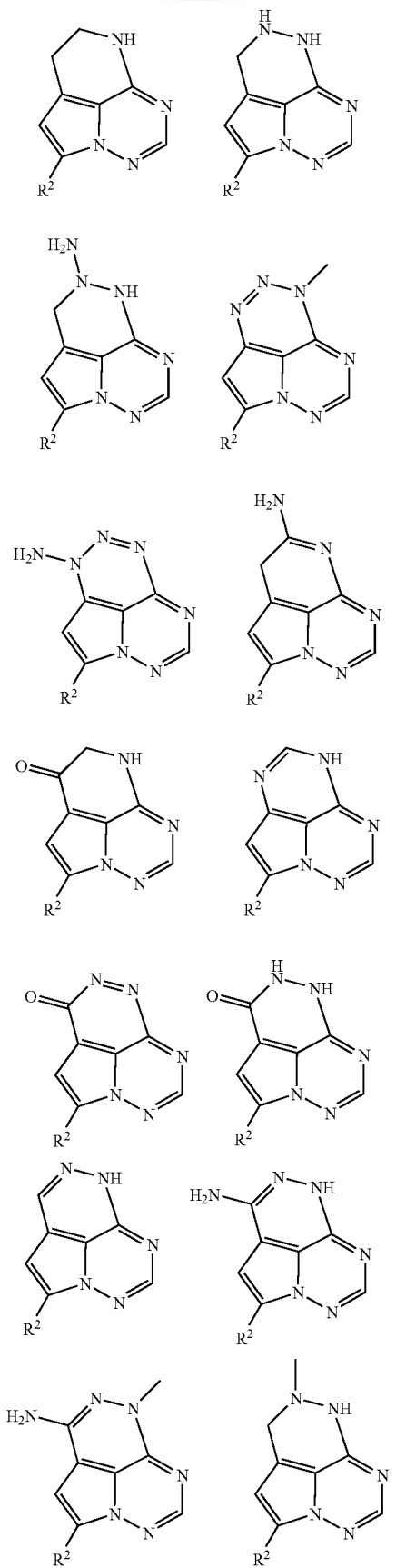
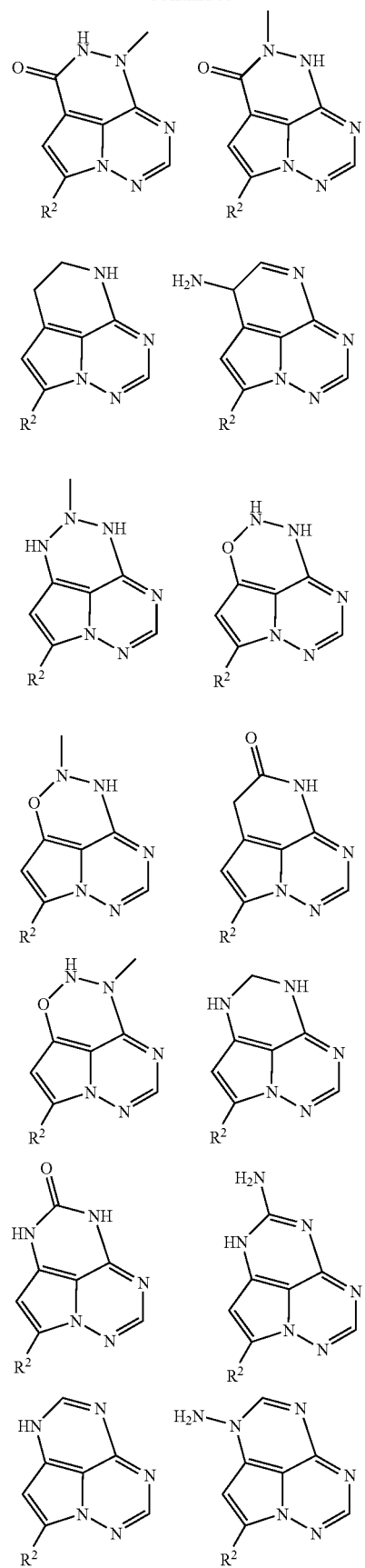

163
-continued
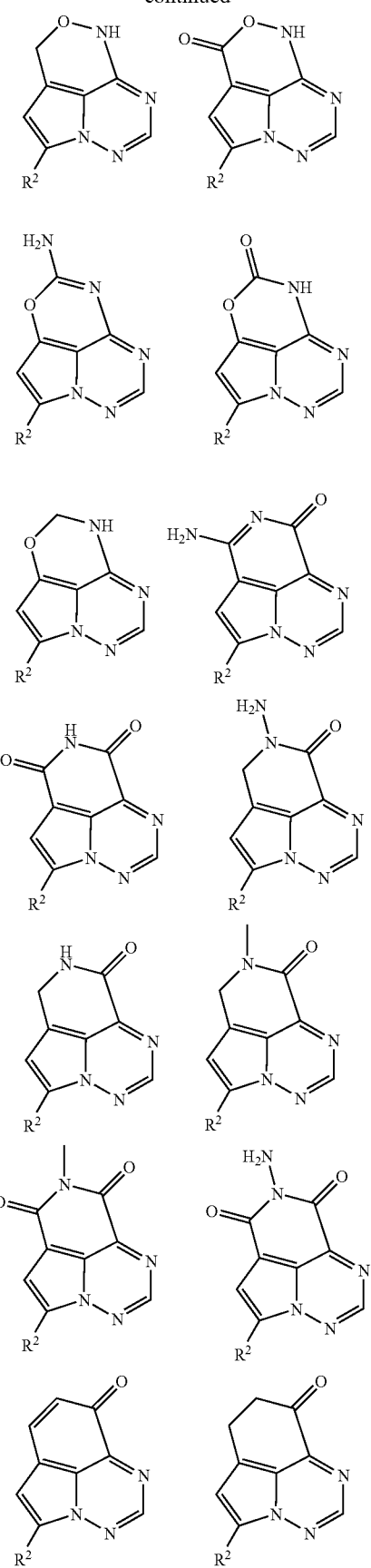
164
-continued
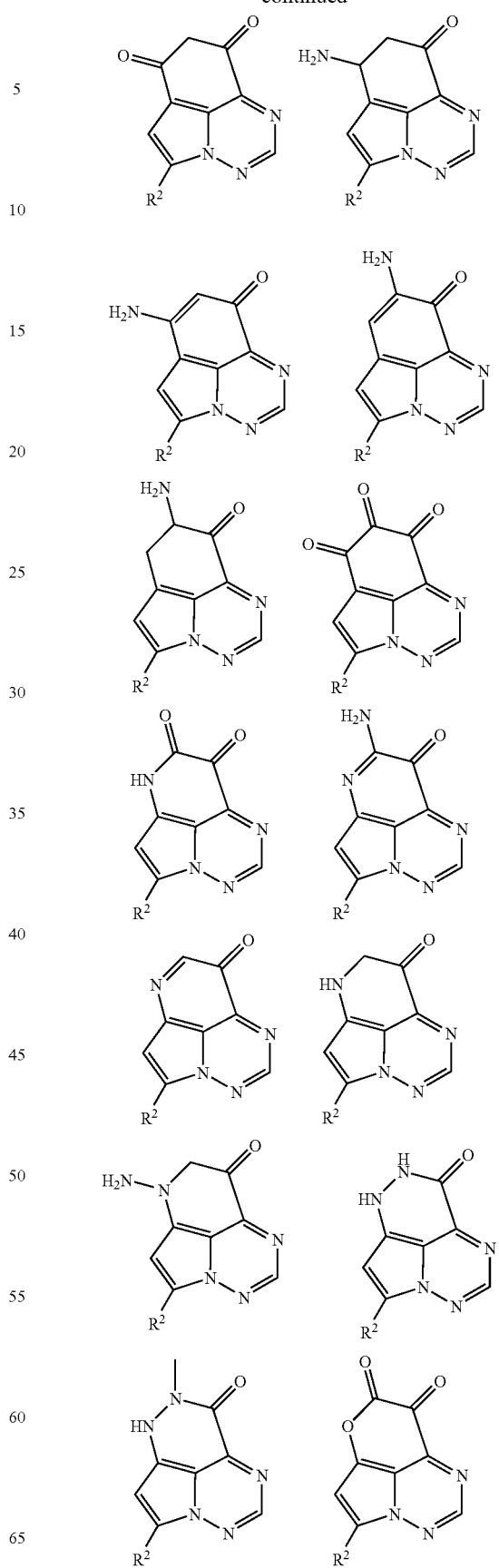

165
-continued
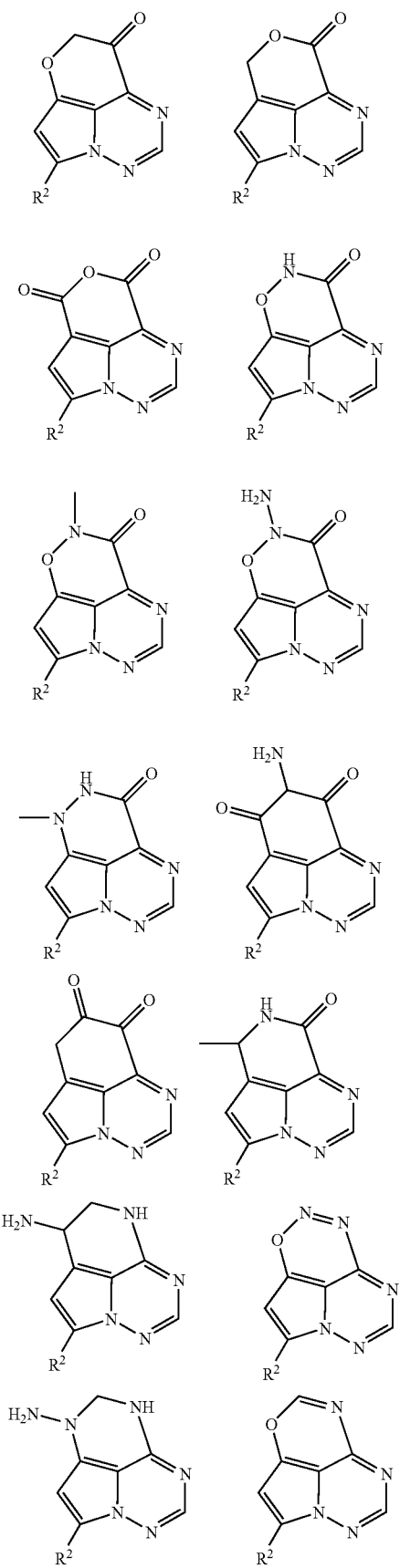
166
-continued
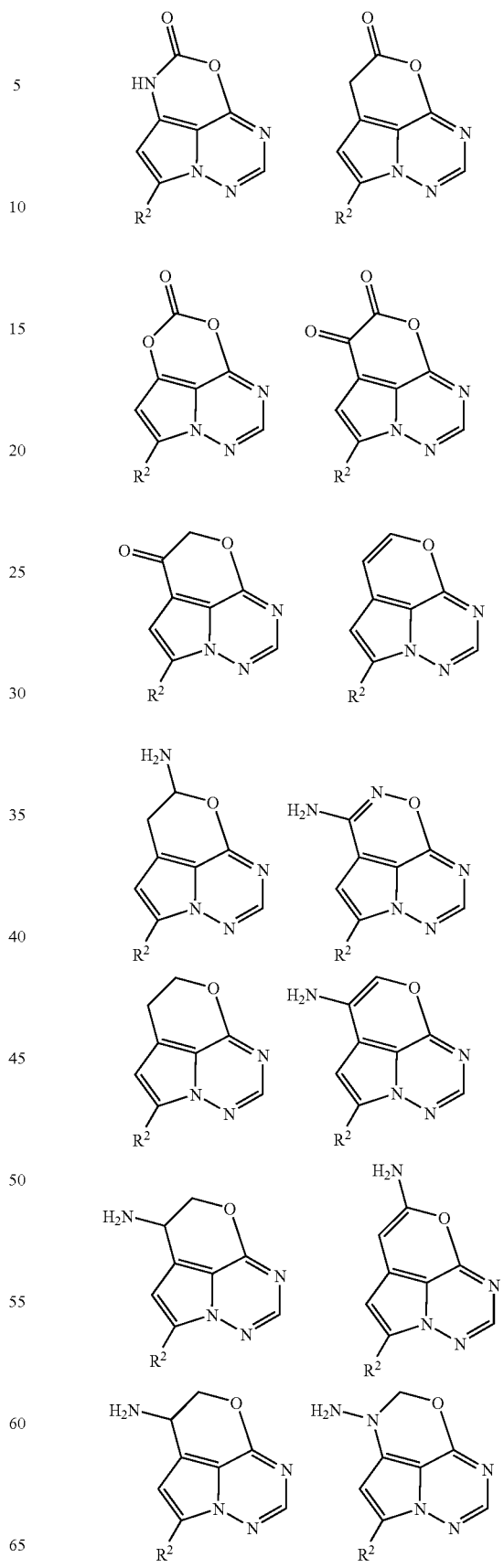

-continued

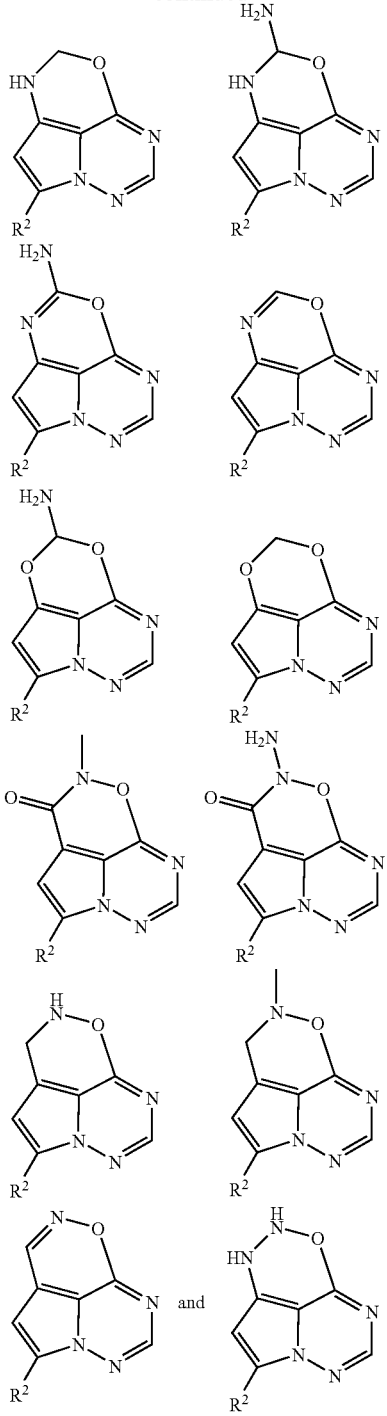

or a pharmaceutically acceptable salt or prodrug thereof.

11. The compound of claim 1 wherein $R^2$ is ribose, 2-methylribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose; or a pharmaceutically acceptable salt or prodrug thereof.

12. The compound of claim 1 wherein $R^2$ is thioribose, 2-deoxythioribose; 2-deoxy-2-fluorothioribose; thioarabinose; 2-deoxy-2-fluorothioarabinose; 2,3-dideoxythioribose; 2,3-dideoxy-2-fluorothioarabinose; 2,3-dideoxy-3-fluorothioribose; 2,3-dideoxy-2,3-didehydrothioribose; or 2,3-dideoxy-3-azidothioribose; or a pharmaceutically acceptable salt or prodrug thereof.

13. The compound of claim 1 wherein $R^2$ is 4-hydroxymethyl-cyclopent-2-ene; 2,3-dihydroxy-4-hydroxymethylcyclopent-4-ene; 3-hydroxy-4-hydroxymethylcyclopentane; 2-hydroxy-4-hydroxymethylcyclopentene; 2-fluoro-3-hydroxy-4-hydroxymethylcyclopentane; 2,3-dihydroxy-4-hydroxymethyl-5-methylenecyclopentane; 4-hydroxymethylcyclopentane, 2,3-dihydroxy-4-hydroxymethylcyclopentane; or 2,3-dihydroxymethylcyclobutane; or a pharmaceutically acceptable salt or prodrug thereof.

14. The compound of claim 1 wherein $R^2$ is 4-hydroxymethyl-pyrrolidine; 2,3-dihydroxy-4-hydroxymethylpyrrolidine; 2/3-hydroxy-4-hydroxymethylpyrrolidine; 2-fluoro-3-hydroxy-4-hydroxymethylpyrrolidine; or 3-fluoro-2-hydroxy-4-hydroxymethyl-pyrrolidine; or a pharmaceutically acceptable salt or prodrug thereof.

15. The compound of claim 1 which is:

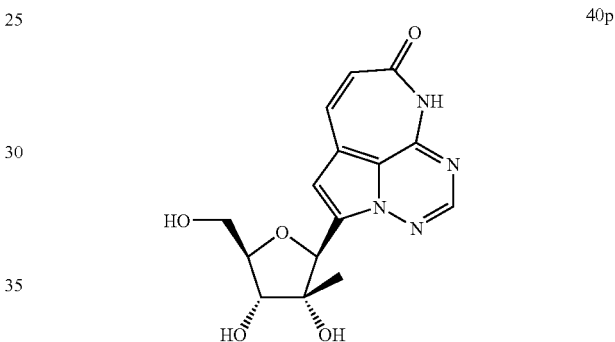

or a pharmaceutically acceptable salt or prodrug thereof.

16. The compound of claim 1 which is:

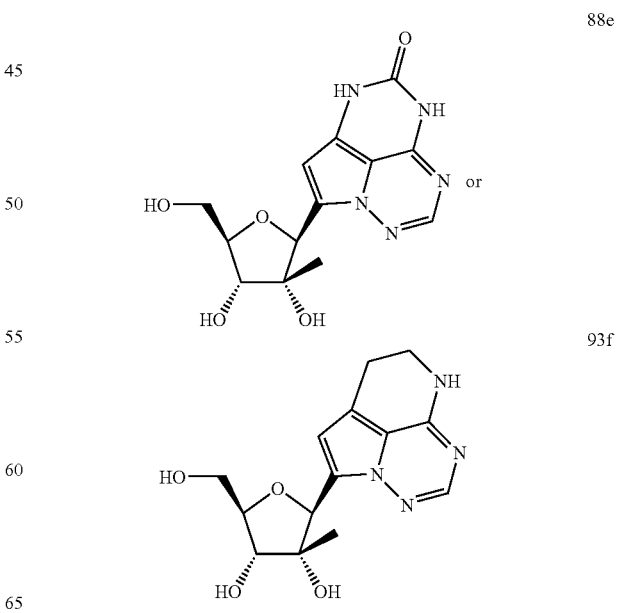

or a pharmaceutically acceptable salt or prodrug thereof.

17. The compound of claim 1 which is:

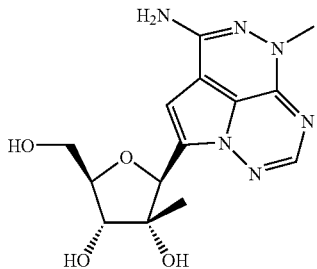

87j or a pharmaceutically acceptable salt or prodrug thereof.

18. The compound of claim 1 which is:

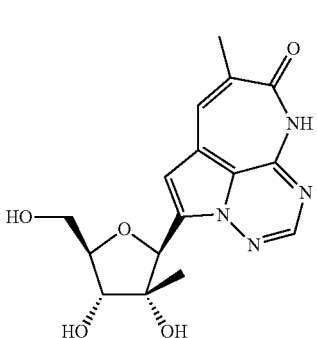

89c

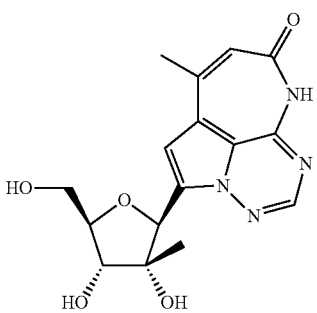

90c

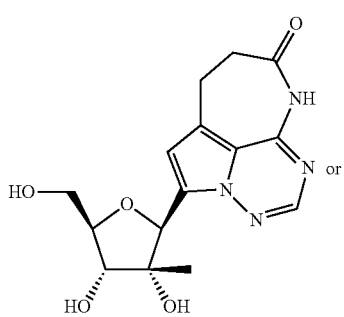

91b

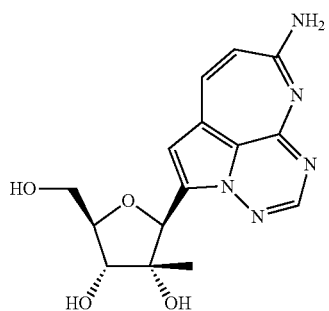

92c or a pharmaceutically acceptable salt or prodrug thereof.

19. The compound of claim 1 which is:

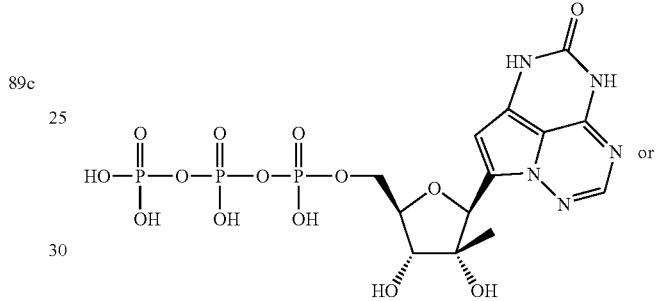

95

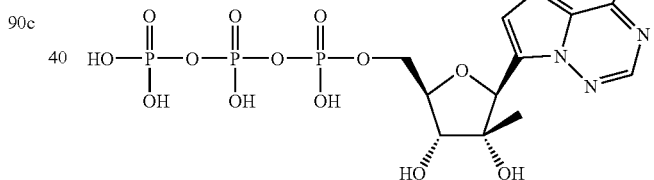

94 or a pharmaceutically acceptable salt or prodrug thereof.

20. The compound of claim 1 which is a prodrug.

21. A pharmaceutical composition comprising a compound as described in claim 1 and a pharmaceutically acceptable carrier.

22. A method for treating a viral infection in an animal comprising administering to the animal an effective amount of a compound as described in claim 1, or a composition as described in claim 21.

23. A method for treating cancer in an animal comprising administering to the animal an effective amount of a compound as described in claim 1, or a composition as described in claim 21.

24. A method for inhibiting a viral RNA or DNA polymerase comprising contacting the polymerase in vitro or in vivo with an effective inhibitory amount of a compound as described in claim 1, or a composition as described in claim 21.

* * * * *